United States Patent
Zhang et al.

(10) Patent No.: US 11,555,042 B2
(45) Date of Patent: Jan. 17, 2023

(54) MACROCYCLIC COMPOUNDS AS TRK KINASES INHIBITORS

(71) Applicant: FOCHON BIOSCIENCES, LTD., Chongqing (CN)

(72) Inventors: Huajie Zhang, Chongqing (CN); Qihong Liu, Chongqing (CN); Chengxi He, Chongqing (CN); Weipeng Zhang, Chongqing (CN); Rui Tan, Chongqing (CN); Bin Liu, Chongqing (CN); Hong Fu, Chongqing (CN); Haohan Tan, Chongqing (CN); Lijun Yang, Chongqing (CN); Hongbin Liu, Chongqing (CN); Yunling Wang, Chongqing (CN); Yuwei Gao, Chongqing (CN); Zongyao Zou, Chongqing (CN); Yanxin Liu, Chongqing (CN); Shu Lin, San Leandro, CA (US); Tongshuang Li, San Leandro, CA (US); Xingdong Zhao, Chongqing (CN); Weibo Wang, Moraga, CA (US)

(73) Assignee: Fochon Biosciences, Ltd., Chongqing (CN)

( * ) Notice: Subject to any disclaimer, the term of this patent is extended or adjusted under 35 U.S.C. 154(b) by 162 days.

(21) Appl. No.: 17/042,385

(22) PCT Filed: Mar. 27, 2019

(86) PCT No.: PCT/CN2019/079909
§ 371 (c)(1),
(2) Date: Sep. 28, 2020

(87) PCT Pub. No.: WO2019/184955
PCT Pub. Date: Oct. 3, 2019

(65) Prior Publication Data
US 2021/0139506 A1 May 13, 2021

Related U.S. Application Data

(60) Provisional application No. 62/800,496, filed on Feb. 2, 2019, provisional application No. 62/684,535, filed on Jun. 13, 2018, provisional application No. 62/674,755, filed on May 22, 2018, provisional application No. 62/648,999, filed on Mar. 28, 2018.

(51) Int. Cl.
| | |
|---|---|
| C07D 498/12 | (2006.01) |
| C07D 519/00 | (2006.01) |
| A61K 31/519 | (2006.01) |
| A61P 29/00 | (2006.01) |
| A61P 35/00 | (2006.01) |
| C07D 498/22 | (2006.01) |
| C07D 487/22 | (2006.01) |
| C07D 498/20 | (2006.01) |

(52) U.S. Cl.
CPC ............ *C07D 498/22* (2013.01); *A61P 35/00* (2018.01); *C07D 487/22* (2013.01); *C07D 498/20* (2013.01); *C07B 2200/05* (2013.01)

(58) Field of Classification Search
CPC ................ C07D 487/04; C07D 498/22; C07D 519/00; A61K 31/519; A61P 29/00; A61P 35/00

See application file for complete search history.

(56) References Cited

FOREIGN PATENT DOCUMENTS

| WO | 2011146336 A1 | 11/2011 |
|---|---|---|
| WO | 201511286 A1 | 7/2015 |
| WO | 2017004342 A1 | 1/2017 |
| WO | 2017015367 A1 | 1/2017 |
| WO | 2017075107 A1 | 5/2017 |
| WO | 2018022911 A1 | 2/2018 |

OTHER PUBLICATIONS

International Search Report dated Jun. 27, 2019 in PCT/CN2019/079909.
Written Opinion dated Jun. 27, 2019 in PCT/CN2019/079909.
Russian Office Action dated Sep. 29, 2021 in corresponding Russian Application No. 2020133631/04.
European Search Report dated Nov. 12, 2021 in corresponding European Application No. 19778044.8.
Australian Examination Report dated Nov. 25, 2021 in corresponding Australian Application No. 2019241260.

*Primary Examiner* — Bruck Kifle
(74) *Attorney, Agent, or Firm* — Ice Miller LLP

(57) ABSTRACT

Provided are certain TRK inhibitors, pharmaceutical compositions thereof, and methods of use thereof.

31 Claims, No Drawings

MACROCYCLIC COMPOUNDS AS TRK KINASES INHIBITORS

CROSS-REFERENCE TO RELATED APPLICATION

This application is a Section 371 of International Application No. PCT/CN2019/079909 filed Mar. 27, 2019, which was published Oct. 3, 2019, under International Publication No. WO 2019/184955 A1, which claims priority under 35 U.S.C. § 119(b) to U.S. Patent Application No. 62/648,999 filed Mar. 28, 2018, U.S. Patent Application No. 62/674,755 filed May 22, 2018, U.S. Patent Application No. 62/684,535 filed Jun. 13, 2018, and U.S. Patent Application No. 62/800,496 filed Feb. 2, 2019, the disclosures of which are incorporated herein by reference in their entireties.

FIELD OF THE INVENTION

Provided are certain compounds or pharmaceutically acceptable salts thereof which can inhibit TRK family protein tyrosine kinases and may be useful for the treatment of hyper-proliferative diseases like cancer and inflammation, autoimmune diseases and pain.

BACKGROUND OF THE INVENTION

Hyper-proliferative diseases like cancer and inflammation are attracting the scientific community to provide therapeutic benefits. In this regard efforts have been made to identify and target specific mechanisms which play a role in proliferating the diseases.

The tropomyosin receptor kinases (TRKs), also known as neurotrophic tyrosine kinase receptor (NTRK), are the transmembrane tyrosine kinases activated by a group of soluble growth factors named neurotrophins (NT). TRK family includes three different members, namely TRKA, TRKB and TRKC, respectively encoded by the NTRK1, NTRK2 and NTRK3 genes. The respective primary neurotrophic ligands for the three TRK isoforms are: nerve growth factor (NGF) which activates TRKA, brain-derived neurotrophic factor (BDNF) which activates TRKB, and neurotrophin-3 (NT-3) which activates TRKC. Extracellular recognition of neurotrophins to TRK proteins induces receptor dimerization, phosphorylation, and activation of the downstream signal transduction pathways via PI3K, RAS/MAPK/ERK, and PLC-gamma.

TRKs are expressed primarily in neuronal tissues and regulate neuronal survival and differentiation of neuronal cells. Dysregulation of TRK pathway, including gene fusions, protein overexpression, and single nucleotide alterations, potentiate many aberrant physiological processes that negatively impact human health. It has been demonstrated that the inhibitors of the NT/TRK signaling pathway serve as effective treatment for multiple pre-clinical animal model of inflammation and pain. In addition, altered TRK signaling pathway is associated with the poor prognosis of different solid malignancies, such as neuroblastoma, breast cancer, pancreatic cancer, melanoma, multiple myeloma, thyroid cancer, glioblastoma, colorectal cancer, sarcomas, cholangiocarcinoma, non-small cell lung cancer and etc. As such, NTRK gene alterations can serve as predictive biomarker for targeted therapy. The on-going clinical development of selective TRK inhibitors have been demonstrated to be beneficial among patients whose tumors harbor NTRK gene alterations.

Therefore, a compound having an inhibitory activity on TRK will be useful for the prevention or treatment of cancer. In this regard, a novel class of TRK inhibitors is provided herein.

DISCLOSURE OF THE INVENTION

Disclosed herein are certain novel compounds, pharmaceutically acceptable salts thereof, and pharmaceutical compositions thereof, and their use as pharmaceuticals.

In one aspect, disclosed herein is a compound of formula (I)

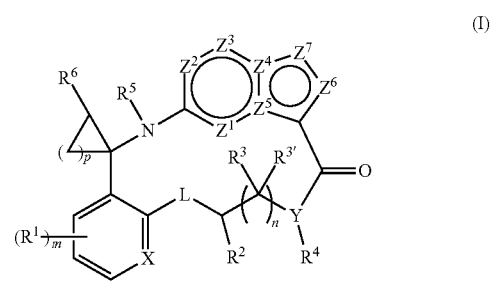

or a pharmaceutically acceptable salt thereof, wherein

X is selected from $CR^X$ and N;

Y is selected from O and N, wherein when Y is O, $R^4$ is absent;

$Z^1, Z^2, Z^3, Z^6$ and $Z^7$ are independently selected from $CR^X$ and N;

$Z^4$ and $Z^5$ are independently selected from C and N, wherein when one of $Z^4$ and $Z^5$ is N, then the other of $Z^4$ and $Z^5$ is C;

L is selected from $-(CR^CR^D)_u-$, $-(CR^CR^D)_uO(CR^CR^D)_t-$, $-(CR^CR^D)_uNR^4(CR^CR^D)_t-$ and $-(CR^CR^D)_uS(CR^CR^D)_t-$;

each $R^1$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $-NR^{A1}R^{B1}$, $-OR^{A1}$, $-C(O)R^{A1}$, $-C(=NR^{E1})R^{A1}$, $-C(=N-OR^{B1})R^{A1}$, $-C(O)OR^{A1}$, $-OC(O)R^{A1}$, $-C(O)NR^{A1}R^{B1}$, $-NR^{A1}C(O)R^{B1}$, $-C(=NR^{E1})NR^{A1}R^{B1}$, $-NR^{A1}C(=NR^{E1})R^{B1}$, $-OC(O)NR^{A1}R^{B1}$, $-NR^{A1}C(O)OR^{B1}$, $-NR^{A1}C(O)NR^{A1}R^{B1}$, $-NR^{A1}C(S)NR^{A1}R^{B1}$, $-NR^{A1}C(=NR^{E1})NR^{A1}R^{B1}$, $-S(O)_rR^{A1}$, $-S(O)(=NR^{E1})R^{B1}$, $-N=S(O)R^{A1}R^{B1}$, $-S(O)_2OR^{A1}$, $-OS(O)_2R^{A1}$, $-NR^{A1}S(O)_rR^{B1}$, $-NR^{A1}S(O)(=NR^{E1})R^{B1}$, $-S(O)_rNR^{A1}R^{B1}$, $-S(O)(=NR^{E1})NR^{A1}R^{B1}$, $-NR^{A1}S(O)_2NR^{A1}R^{B1}$, $-NR^{A1}S(O)(=NR^{E1})NR^{A1}R^{B1}$, $-P(O)R^{A1}R^{B1}$ and $-P(O)(OR^{A1})(OR^{B1})$, wherein alkyl, alkenyl, alkynyl, cycloalkyl, heterocyclyl, aryl and heteroaryl are each unsubstituted or substituted with at least one substituent, independently selected from $R^X$;

$R^2$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $-NR^{A2}R^{B2}$, $-OR^{A2}$, $-C(O)R^{A2}$, $-C(O)OR^{A2}$, $-OC(O)R^{A2}$, $-C(O)NR^{A2}R^{B2}$, $-NR^{A2}C(O)R^{B2}$ and $-S(O)_rR^{A2}$, wherein alkyl, alkenyl, alkynyl, cycloalkyl, heterocyclyl, aryl and heteroaryl are each unsubstituted or substituted with at least one substituent, independently selected from $R^X$;

each $R^3$ and $R^{3'}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, —$NR^{A3}R^{B3}$, —$OR^{A3}$, —$C(O)R^{A3}$, —$C(O)OR^{A3}$, —$OC(O)R^{A3}$, —$C(O)NR^{A3}R^{B3}$, —$NR^{A3}C(O)R^{B3}$, and —$S(O)_rR^{A3}$, wherein alkyl, alkenyl, alkynyl, cycloalkyl, heterocyclyl, aryl and heteroaryl are each unsubstituted or substituted with at least one substituent, independently selected from $R^X$; or "$R^2$ and $R^{3}$" or "$R^2$ and $R^{3'}$" together with the carbon atoms to which they are attached form a $C_{5-7}$ cycloalkyl or heterocyclic ring of 3 to 7 members containing 1, 2 or 3 heteroatoms independently selected from oxygen, sulfur, nitrogen and phosphorus, and optionally substituted with 1, 2 or 3 $R^X$ groups;

or $R^3$ and $R^{3'}$ together with the carbon atoms to which they are attached form a $C_{3-7}$ cycloalkyl or heterocyclic ring of 4 to 7 members containing 1, 2 or 3 heteroatoms independently selected from oxygen, sulfur, nitrogen and phosphorus, and optionally substituted with 1, 2 or 3 $R^X$ groups;

$R^4$ is selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, wherein alkyl, alkenyl, alkynyl, and cycloalkyl are each unsubstituted or substituted with at least one substituent, independently selected from $R^X$;

or $R^3$ and $R^4$ together with the atoms to which they are attached form a heterocyclic ring of 4 to 7 members containing 0, 1 or 2 additional heteroatoms independently selected from oxygen, sulfur, nitrogen and phosphorus, and optionally substituted with 1, 2 or 3 $R^X$ groups;

$R^5$ is selected from hydrogen, $C_{1-10}$ alkyl, $C_{2-10}$ alkenyl, $C_{2-10}$ alkynyl, $C_{3-10}$ cycloalkyl and $C_{3-10}$ cycloalkyl-$C_{1-4}$ alkyl, wherein alkyl, alkenyl, alkynyl and cycloalkyl are each unsubstituted or substituted with at least one substituent, independently selected from $R^X$;

$R^6$ is selected from hydrogen, halogen, $C_{1-10}$ alkyl, $C_{2-10}$ alkenyl, $C_{2-10}$ alkynyl, $C_{3-10}$ cycloalkyl and $C_{3-10}$ cycloalkyl-$C_{1-4}$ alkyl, wherein alkyl, alkenyl, alkynyl and cycloalkyl are each unsubstituted or substituted with at least one substituent, independently selected from $R^X$;

or $R^5$ and $R^6$ together with the atoms to which they are attached form a heterocyclic ring of 5 to 7 members containing 0, 1 or 2 additional heteroatoms independently selected from oxygen, sulfur, nitrogen and phosphorus, and optionally substituted with 1, 2 or 3 $R^X$ groups;

each $R^A$, $R^{A1}$, $R^{A2}$, $R^{A3}$, $R^{B1}$, $R^{B2}$ and $R^{B3}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heterocyclyl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^X$;

or each "$R^{A1}$ and $R^{B1}$", "$R^{A2}$ and $R^{B2}$" and "$R^{A3}$ and $R^{B3}$" together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2 or 3 $R^X$ groups;

$R^C$ and $R^D$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^X$;

or $R^C$ and $R^D$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^X$ groups;

$R^{E1}$ is selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $OR^{a1}$, $SR^{a1}$, —$S(O)_rR^{a1}$, —$C(O)R^{a1}$, $C(O)OR^{a1}$, —$C(O)NR^{a1}R^{b1}$ and —$S(O)_rNR^{a1}R^{b1}$, wherein alkyl, alkenyl, alkynyl, cycloalkyl, heterocyclyl, aryl and heteroaryl are each unsubstituted or substituted with at least one substituent, independently selected from $R^Y$;

each $R^X$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, —$(CR^{c1}R^{d1})_tNR^{a1}R^{b1}$, —$(CR^{c1}R^{d1})_tOR^{b1}$, —$(CR^{c1}R^{d1})_tC(O)R^{a1}$, —$(CR^{c1}R^{d1})_tC(=NR^{e1})R^{a1}$, —$(CR^{c1}R^{d1})_tC(=N—OR^{b1})R^{a1}$, —$(CR^{c1}R^{d1})_tC(O)OR^{b1}$, —$(CR^{c1}R^{d1})_tOC(O)R^{b1}$, —$(CR^{c1}R^{d1})_tC(O)NR^{a1}R^{b1}$, —$(CR^{c1}R^{d1})_tNR^{a1}C(O)R^{b1}$, —$(CR^{c1}R^{d1})_tC(=NR^{e1})NR^{a1}R^{b1}$, —$(CR^{c1}R^{d1})_tNR^{a1}C(=NR^{e1})R^{b1}$, —$(CR^{c1}R^{d1})_tOC(O)NR^{a1}R^{b1}$, —$(CR^{c1}R^{d1})_tNR^{a1}C(O)OR^{b1}$, —$(CR^{c1}R^{d1})_tNR^{a1}C(O)NR^{a1}R^{b1}$, —$(CR^{c1}R^{d1})_tNR^{a1}C(S)NR^{a1}R^{b1}$, —$(CR^{c1}R^{d1})_tNR^{a1}C(=NR^{e1})NR^{a1}R^{b1}$, —$(CR^{c1}R^{d1})_tS(O)_rR^{b1}$, —$(CR^{c1}R^{d1})_tS(O)(=NR^{e1})R^{b1}$, —$(CR^{c1}R^{d1})_tN=S(O)R^{a1}R^{b1}$, —$(CR^{c1}R^{d1})_tS(O)_2OR^{b1}$, —$(CR^{c1}R^{d1})_tOS(O)_2R^{b1}$, —$(CR^{c1}R^{d1})_tNR^{a1}S(O)_rR^{b1}$, —$(CR^{c1}R^{d1})_tNR^{a1}S(O)(=NR^{e1})R^{b1}$, —$(CR^{c1}R^{d1})_tS(O)_rNR^{a1}R^{b1}$, —$(CR^{c1}R^{d1})_tS(O)(=NR^{e1})NR^{a1}R^{b1}$, —$(CR^{c1}R^{d1})_tNR^{a1}S(O)_2NR^{a1}R^{b1}$, —$(CR^{c1}R^{d1})_tNR^{a1}S(O)(=NR^{e1})NR^{a1}R^{b1}$, —$(CR^{c1}R^{d1})_tP(O)R^{a1}R^{b1}$ and —$(CR^{c1}R^{d1})_tP(O)(OR^{a1})(OR^{b1})$, wherein alkyl, alkenyl, alkynyl, cycloalkyl, heterocyclyl, aryl and heteroaryl are each unsubstituted or substituted with at least one substituent, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^Y$;

or $R^{a1}$ and $R^{b1}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^Y$;

or $R^{c1}$ and $R^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, CN, $NO_2$, —$OR^{a2}$, —$SR^{a2}$, —$S(O)_rR^{a2}$, —$C(O)R^{a2}$, —$C(O)OR^{a2}$, —$S(O)_rNR^{a2}R^{b2}$ and —$C(O)NR^{a2}R^{b2}$;

each $R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, —$(CR^{c2}R^{d2})_tNR^{a2}R^{b2}$, —$(CR^{c2}R^{d2})_tOR^{b2}$, —$(CR^{c2}R^{d2})_tC(O)R^{a2}$, —$(CR^{c2}R^{d2})_tC(=NR^{e2})R^{a2}$, —$(CR^{c2}R^{d2})_tC(=N—OR^{b2})R^{a2}$, —$(CR^{c2}R^{d2})_tC(O)OR^{b2}$, —$(CR^{c2}R^{d2})_tOC(O)R^{b2}$, —$(CR^{c2}R^{d2})_tC(O)NR^{a2}R^{b2}$, —$(CR^{c2}R^{d2})_tNR^{a2}C(O)R^{b2}$, —$(CR^{c2}R^{d2})_tC(=NR^{e2})NR^{a2}R^{b2}$, —$(CR^{c2}R^{d2})_tNR^{a2}C(=NR^{e2})R^{b2}$, —$(CR^{c2}R^{d2})_tOC(O)NR^{a2}R^{b2}$, —$(CR^{c2}R^{d2})_tNR^{a2}C(O)OR^{b2}$, —$(CR^{c2}R^{d2})_tNR^{a2}C(O)NR^{a2}R^{b2}$, —$(CR^{c2}R^{d2})_tNR^{a2}C(S)NR^{a2}R^{b2}$, —$(CR^{c2}R^{d2})_tNR^{a2}C(=NR^{e2})NR^{a2}R^{b2}$, —$(CR^{c2}R^{d2})_tS(O)_rR^{b2}$, —$(CR^{c2}R^{d2})_tS(O)(=NR^{e2})R^{b2}$, —$(CR^{c2}R^{d2})_tN=S(O)R^{a2}R^{b2}$, —$(CR^{c2}R^{d2})_tS(O)_2OR^{b2}$, —$(CR^{c2}R^{d2})_tOS(O)_2R^{b2}$, —$(CR^{c2}R^{d2})_tNR^{a2}S(O)_rR^{b2}$, —$(CR^{c2}R^{d2})_tNR^{a2}S(O)(=NR^{e2})R^{b2}$, —$(CR^{c2}R^{d2})_tS(O)_rNR^{a2}R^{b2}$, —$(CR^{c2}R^{d2})_tS(O)(=NR^{e2})NR^{a2}R^{b2}$, —$(CR^{c2}R^{d2})_tNR^{a2}S(O)_2NR^{a2}R^{b2}$, —$(CR^{c2}R^{d2})_tNR^{a2}S(O)(=NR^{e2})NR^{a2}R^{b2}$, —$(CR^{c2}R^{d2})_tP(O)R^{a2}R^{b2}$ and —$(CR^{c2}R^{d2})_tP(O)(OR^{a2})(OR^{b2})$, wherein alkyl, alkenyl, alkynyl, cycloalkyl, heterocyclyl, aryl and heteroaryl are each unsubstituted or substituted with at least one substituent, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —$C(O)C_{1-4}$ alkyl, —$C(O)C_{3-10}$ cycloalkyl, —$C(O)OC_{1-4}$ alkyl, —$C(O)OC_{3-10}$ cycloalkyl, —$C(O)N(C_{1-4}$ alkyl$)_2$, —$C(O)N(C_{3-10}$ cycloalkyl$)_2$, —$S(O)_2C_{1-4}$ alkyl, —$S(O)_2C_{3-10}$ cycloalkyl, —$S(O)_2N(C_{1-4}$ alkyl$)_2$ and —$S(O)_2N(C_{3-10}$ cycloalkyl$)_2$;

m is selected from 0, 1, 2, 3 and 4;
n is selected from 1, 2, 3 and 4;
p is selected from 1, 2, 3 and 4;
each r is independently selected from 0, 1 and 2;
each t is independently selected from 0, 1, 2, 3 and 4;
each u is independently selected from 0, 1, 2, 3 and 4.

In one aspect, disclosed herein is a compound of formula (I) or a pharmaceutically acceptable salt thereof, wherein $R^{3'}$ is hydrogen, shown as formula (II):

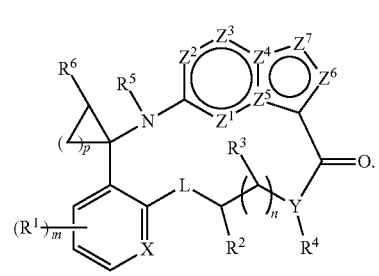

(II)

In one aspect, disclosed herein is a compound of formula (I), wherein $R^3$ and $R^{3'}$ together with the carbon atoms to which they are attached form a $C_{3-7}$ cycloalkyl or heterocyclic ring of 4 to 7 members containing 1, 2 or 3 heteroatoms independently selected from oxygen, sulfur, nitrogen and phosphorus, and optionally substituted with 1, 2 or 3 $R^X$ groups.

In yet another aspect, the present disclosure provides pharmaceutical compositions comprising a compound of formula (I)/(II) or a pharmaceutically acceptable salt thereof and a pharmaceutically acceptable excipient.

In yet another aspect, the disclosure provides methods for modulating TRK, comprising administering to a system or a subject in need thereof, a therapeutically effective amount of a compound of formula (I)/(II) or a pharmaceutically acceptable salt thereof or pharmaceutical compositions thereof, thereby modulating said TRK.

In yet another aspect, disclosed is a method to treat, ameliorate or prevent a condition which responds to inhibition of TRK comprising administering to a system or subject in need of such treatment an effective amount of a compound of formula (I)/(II) or a pharmaceutically acceptable salt thereof or pharmaceutical compositions thereof, and optionally in combination with a second therapeutic agent, thereby treating said condition.

Alternatively, the present disclosure provides the use of a compound of formula (I)/(II) or a pharmaceutically acceptable salt thereof in the manufacture of a medicament for treating a condition mediated by TRK. In particular embodiments, the compounds of the disclosure may be used alone or in combination with a second therapeutic agent to treat a condition mediated by TRK.

Alternatively, disclosed is a compound of formula (I)/(II) or a pharmaceutically acceptable salt thereof for treating a condition mediated by TRK.

Specifically, the condition herein includes but not limited to, an autoimmune disease, a transplantation disease, an infectious disease or a cell proliferative disorder.

Furthermore, the disclosure provides methods for treating a cell proliferative disorder, comprising administering to a system or subject in need of such treatment an effective amount of a compound of formula (I)/(II) or a pharmaceutically acceptable salt thereof or pharmaceutical compositions thereof, and optionally in combination with a second therapeutic agent, thereby treating said condition.

Alternatively, the present disclosure provides the use of a compound of formula (I)/(II) or a pharmaceutically acceptable salt thereof in the manufacture of a medicament for treating a cell-proliferative disorder. In particular examples, the compounds of the disclosure may be used alone or in combination with a chemotherapeutic agent to treat a cell proliferative disorder.

Specifically, the cell proliferative disorder disclosed herein includes but not limited to, lymphoma, osteosarcoma, melanoma, or a tumor of breast, renal, prostate, colorectal, thyroid, ovarian, pancreatic, neuronal, lung, uterine or gastrointestinal tumor.

In the above methods for using the compounds of the disclosure, a compound of formula (I)/(II) or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

The term "substituted" means that a hydrogen atom is removed and replaced by a substituent. It is to be understood that substitution at a given atom is limited by valency. Throughout the definitions, the term "$C_{i\text{-}j}$" indicates a range which includes the endpoints, wherein i and j are integers and indicate the number of carbons. Examples include $C_{1\text{-}4}$, $C_{1\text{-}10}$, $C_{3\text{-}10}$, and the like.

The term "at least one" or "one or more" means one, two, three, four or five or more.

The term "alkyl", employed alone or in combination with other terms, refers to both branched and straight-chain saturated aliphatic hydrocarbon groups having the specified number of carbon atoms. Unless otherwise specified, "alkyl" refers to $C_{1\text{-}10}$ alkyl. For example, $C_{1\text{-}6}$, as in "$C_{1\text{-}6}$ alkyl" is defined to include groups having 1, 2, 3, 4, 5, or 6 carbons in a linear or branched arrangement. For example, "$C_{1\text{-}8}$ alkyl" includes but is not limited to methyl, ethyl, n-propyl, i-propyl, n-butyl, t-butyl, i-butyl, pentyl, hexyl, heptyl, and octyl.

The term "cycloalkyl", employed alone or in combination with other terms, refers to a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0³,⁷]nonane and tricyclo[3.3.1.1³,⁷]decane (adamantane). The monocyclic and bridged cycloalkyl can be attached to the parent molecular moiety through any substitutable atom contained within the ring system.

The term "alkenyl", employed alone or in combination with other terms, refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to, ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl", employed alone or in combination with other terms, refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "halogen" (or "halo") refers to fluorine, chlorine, bromine and iodine.

The term "alkoxy", employed alone or in combination with other terms, refers to an alkyl radical that is single bonded to an oxygen atom. The attachment point of an alkoxy radical to a molecule is through the oxygen atom. An alkoxy radical may be depicted as —O-alkyl. The term "$C_{1-10}$ alkoxy" refers to an alkoxy radical containing from one to ten carbon atoms, having straight or branched moieties. Alkoxy groups, includes but is not limited to, methoxy, ethoxy, propoxy, isopropoxy, butoxy, pentyloxy, hexyloxy, and the like.

The term "cycloalkoxy", employed alone or in combination with other terms, refers to cycloalkyl radical that is single bonded to an oxygen atom. The attachment point of a cycloalkoxy radical to a molecule is through the oxygen atom. A cycloalkoxy radical may be depicted as —O-cycloalkyl. "$C_{3-10}$ cycloalkoxy" refers to a cycloalkoxy radical containing from three to ten carbon atoms. Cycloalkoxy groups, includes but is not limited to, cyclopropoxy, cyclobutoxy, cyclopentyloxy, cyclohexyloxy, and the like.

The term "alkylthio", employed alone or in combination with other terms, refers to an alkyl radical that is single bonded to a sulfur atom. The attachment point of an alkylthio radical to a molecule is through the sulfur atom. An alkylthio radical may be depicted as —S-alkyl. The term "$C_{1-10}$ alkylthio" refers to an alkylthio radical containing from one to ten carbon atoms, having straight or branched moieties. Alkylthio groups, includes but is not limited to, methylthio, ethylthio, propylthio, isopropylthio, butylthio, hexylthio, and the like.

The term "cycloalkylthio", employed alone or in combination with other terms, refers to cycloalkyl radical that is single bonded to a sulfur atom. The attachment point of a cycloalkylthio radical to a molecule is through the sulfur atom. A cycloalkylthio radical may be depicted as —S-cycloalkyl. "$C_{3-10}$ cycloalkylthio" refers to a cycloalkylthio radical containing from three to ten carbon atoms. Cycloalkylthio groups, includes but is not limited to, cyclopropylthio, cyclobutylthio, cyclohexylthio, and the like.

The term "alkylamino", employed alone or in combination with other terms, refers to an alkyl radical that is single bonded to a nitrogen atom. The attachment point of an alkylamino radical to a molecule is through the nitrogen atom. An alkylamino radical may be depicted as —NH(alkyl). The term "$C_{1-10}$ alkylamino" refers to an alkylamino radical containing from one to ten carbon atoms, having straight or branched moieties. Alkylamino groups, includes but is not limited to, methylamino, ethylamino, propylamino, isopropylamino, butylamino, hexylamoino, and the like.

The term "cycloalkylamino", employed alone or in combination with other terms, refers to cycloalkyl radical that is single bonded to a nitrogen atom. The attachment point of a cycloalkylamino radical to a molecule is through the nitrogen atom. A cycloalkylamino radical may be depicted as —NH(cycloalkyl). "$C_{3-10}$ cycloalkylamino" refers to a cycloalkylamino radical containing from three to ten carbon atoms. Cycloalkylamino groups, includes but is not limited to, cyclopropylamino, cyclobutylamino, cyclohexylamino, and the like.

The term "di(alkyl)amino", employed alone or in combination with other terms, refers to two alkyl radicals that are single bonded to a nitrogen atom. The attachment point of an di(alkyl)amino radical to a molecule is through the nitrogen atom. A di(alkyl)amino radical may be depicted as —N(alkyl)$_2$. The term "di($C_{1-10}$ alkyl)amino" refers to a di($C_{1-10}$ alkyl)amino radical wherein the alkyl radicals each independently contains from one to ten carbon atoms, having straight or branched moieties.

The term "aryl", employed alone or in combination with other terms, encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring. The "aryl" may contain 5-20 carbon atoms ($C_{5-20}$ aryl), for example 6-14 carbon atoms ($C_{6-14}$ aryl) or 6-10 carbon atoms ($C_{6-10}$ aryl), e.g. phenyl, naphthyl, indanyl, fluorenyl etc.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "heteroaryl", employed alone or in combination with other terms, refers to
- 5- to 8-membered aromatic, monocyclic rings containing one or more, for example, from 1 to 4, or, in some embodiments, from 1 to 3, heteroatoms selected from N, O and S, with the remaining ring atoms being carbon;
- 8- to 12-membered bicyclic rings containing one or more, for example, from 1 to 4, or, in some embodiments, from 1 to 3, heteroatoms selected from N, O and S, with the remaining ring atoms being carbon and wherein at least one heteroatom is present in an aromatic ring; and
- 11- to 14-membered tricyclic rings containing one or more, for example, from 1 to 4, or in some embodiments, from 1 to 3, heteroatoms selected from N, O and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle", employed alone or in combination with other terms, (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, nitrogen and phosphorus as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, nitrogen and phosphorus. "Heterocycle" also refers to 5- to 7-membered heterocyclic ring containing one or more heteroatoms selected from oxygen, sulfur, nitrogen and phosphorus fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl. 1,4-piperazinyl and 2,3-pyridazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Bicyclic heterocycles include, for example:

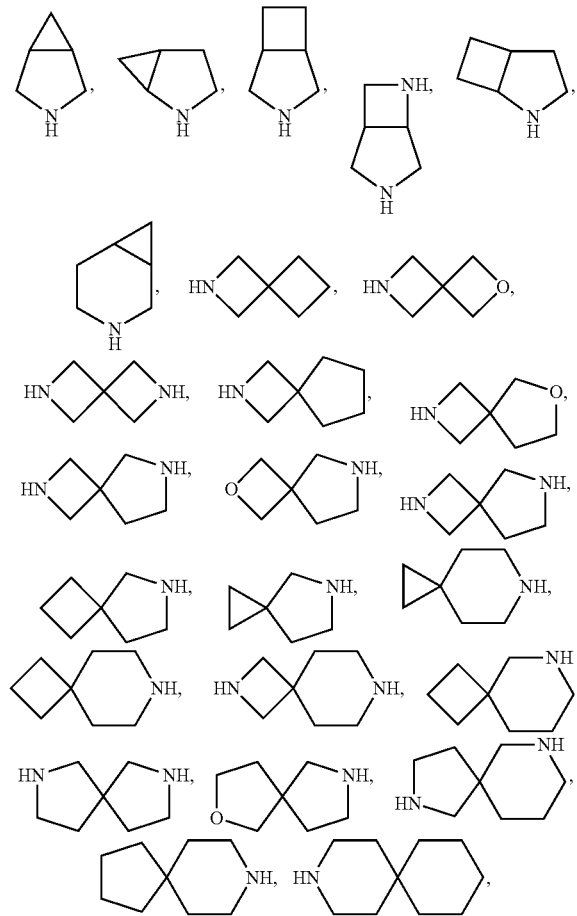

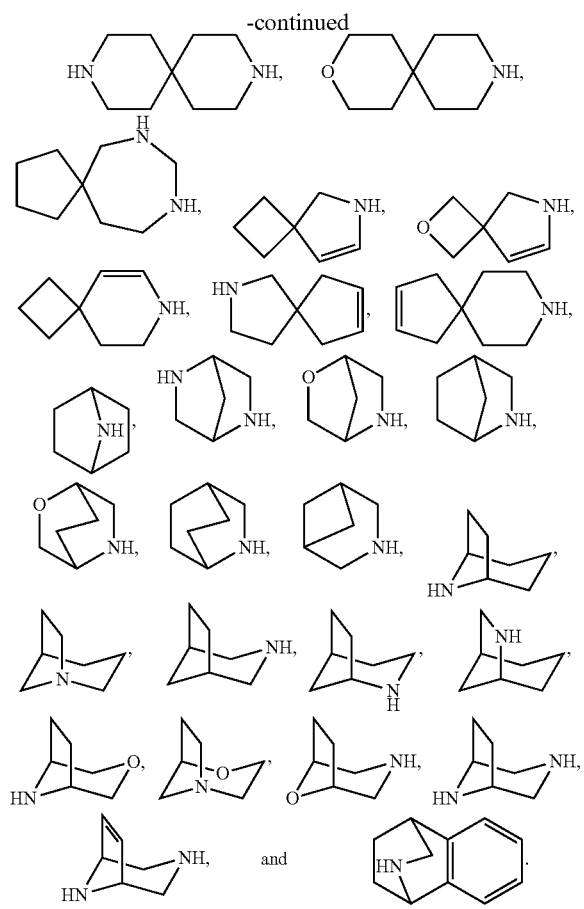

As used herein, "aryl-alkyl" refers to an alkyl moiety substituted by an aryl group. Example aryl-alkyl groups include benzyl, phenethyl and naphthylmethyl groups. In some embodiments, aryl-alkyl groups have from 7 to 20 or 7 to 11 carbon atoms. When used in the phrase "aryl-$C_{1-4}$ alkyl", the term "$C_{1-4}$" refers to the alkyl portion of the moiety and does not describe the number of atoms in the aryl portion of the moiety.

As used herein, "heterocyclyl-alkyl" refers to alkyl substituted by heterocyclyl. When used in the phrase "heterocyclyl-$C_{1-4}$ alkyl", the term "$C_{1-4}$" refers to the alkyl portion of the moiety and does not describe the number of atoms in the heterocyclyl portion of the moiety.

As used herein, "cycloalkyl-alkyl" refers to alkyl substituted by cycloalkyl. When used in the phrase "$C_{3-10}$ cycloalkyl-$C_{1-4}$alkyl", the term "$C_{3-10}$" refers to the cycloalkyl portion of the moiety and does not describe the number of atoms in the alkyl portion of the moiety, and the term "$C_{1-4}$" refers to the alkyl portion of the moiety and does not describe the number of atoms in the cycloalkyl portion of the moiety.

As used herein, "heteroaryl-alkyl" refers to alkyl substituted by heteroaryl. When used in the phrase "heteroaryl-$C_{1-4}$ alkyl", the term "$C_{1-4}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl and/or heteroaryl refers to substitution of each of those groups individually as well as to substitutions of combinations of those groups. That is, if $R^1$ is aryl-$C_{1-4}$ alkyl, the aryl portion may be unsubstituted or substituted with at least one substituent, independently selected from $R^x$ and the alkyl portion may also be unsubstituted or substituted with at least one substituent, independently selected from $R^x$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium and zinc salts. Further, for example, the pharmaceutically acceptable salts derived from inorganic bases may be selected from ammonium, calcium, magnesium, potassium and sodium salts. Salts in the solid form may exist in one or more crystal structures, and may also be in the form of hydrates. Salts derived from pharmaceutically acceptable organic non-toxic bases may be selected, for example, from salts of primary, secondary and tertiary amines, substituted amines including naturally occurring substituted amines, cyclic amines and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric and p-toluenesulfonic acids. In some embodiments, such acid may be selected, for example, from citric, hydrobromic, hydrochloric, maleic, phosphoric, sulfuric, fumaric and tartaric acids.

The terms "administration of" and or "administering" a compound or a pharmaceutically acceptable salt should be understood to mean providing a compound or a pharmaceutically acceptable salt thereof to the individual in recognized need of treatment.

The term "effective amount" means the amount of the a compound or a pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s) and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The term "NH protecting group" as used herein includes, but not limited to, trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyloxy carbonyl, 4-(phenylazo)-benzyloxy carbonyl, 2-furfuryloxycarbonyl, diphenylmethoxy carbonyl, 1,1-dimethyl-propoxy-carbonyl, isopropoxy carbonyl, phthaloyl, succinyl, alanyl, leucyl, 1-adamantyloxycarbonyl, 8-quinolyloxy carbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl and triphenylsilyl.

The term "C(O)OH protecting group" as used herein includes, but not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl, 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl and tert-butylmethoxyphenylsilyl.

The term "OH or SH protecting group" as used herein includes, but not limited to, benzyloxycarbonyl, 4-nitrobenzyloxycarbonyl, 4-bromobenzyloxy carbonyl, 4-methoxybenzyloxy carbonyl, 3,4-dimethoxybenzyloxycarbonyl, methoxy carbonyl, ethoxy carbonyl, tert-butoxy carbonyl, 1,1-dimethylpropoxy carbonyl, isopropoxy carbonyl, isobutyloxy carbonyl, diphenylmethoxy carbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxy carbonyl, 2-furfuryloxycarbonyl, 1-adamantyloxy carbonyl, vinyloxy carbonyl, allyloxy carbonyl, 4-ethoxy-1-naphthyloxycarbonyl, 8-quinolyloxy carbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl and tert-butylmethoxyphenylsilyl.

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85-90%, more preferably an excess of about 95-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, nitrogen, oxygen, phosphorous, sulfur, fluorine, chlorine and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$ and $^{125}I$. Compounds that contain other isotopes of these and/or other atoms are within the scope of this invention.

In another embodiment, the isotope-labeled compounds contain deuterium (H), tritium (H) or C isotopes. Therefore when a substituent is described as hydrogen, it also incorporates the isotopic equivalents such as deuterium and tritium, in particular deuterium (D). Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuterated acid such as $D_2SO_4/D_2O$. In addition to the above, relevant procedures and intermediates are disclosed, for instance, in Lizondo, J et al, Drugs Fut, 21(11), 1116 (1996); Brickner, S J et al., J Med Chem, 39(3), 673 (1996); Mallesham, B et al, Org Lett, 5(7), 963 (2003); PCT publications WO 1997010223, WO2005099353, WO 1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of TRK inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al, J. Labelled Comp. Radiopharmaceut., 36(10):927-932 (1995); Kushner et al., Can. J. Physiol. Pharmacol, 77, 79-88 (1999).

In addition, non-radioactive isotope containing drugs, such as deuterated drugs called "heavy drugs" can be used for the treatment of diseases and conditions related to TRK activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201:357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

In an Embodiment (1), this invention provides to a compound of formula (I)

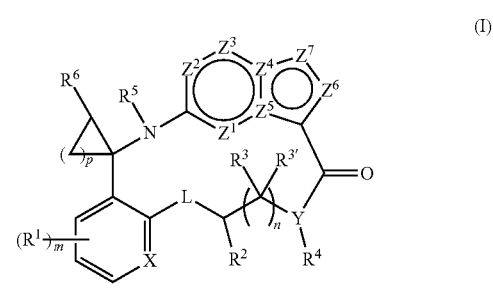

or a pharmaceutically acceptable salt thereof, wherein
X is selected from $CR^X$ and N;
Y is selected from O and N, wherein when Y is O, $R^4$ is absent;
$Z^1$, $Z^2$, $Z^3$, $Z^6$ and $Z^7$ are independently selected from $CR^X$ and N;
$Z^4$ and $Z^5$ are independently selected from C and N, wherein when one of $Z^4$ and $Z^5$ is N, then the other of $Z^4$ and $Z^5$ is C;
L is selected from —$(CR^C R^D)_u$—, —$(CR^C R^D)_u O(CR^C R^D)_t$, —$(CR^C R^D)_u NR^4(CR^C R^D)_t$— and —$(CR^C R^D)_u S(CR^C R^D)_t$;
each $R^1$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, —$NR^{A1}R^{B1}$, —$OR^{A1}$, —$C(O)R^{A1}$, —$C(=NR^{E1})R^{A1}$, —$C(=N-OR^{B1})R^{A1}$, —$C(O)OR^{a1}$, —$OC(O)R^{A1}$, —$C(O)NR^{A1}R^{B1}$, —$NR^{A1}C(O)R^{B1}$, —$C(=NR^{E1})NR^{A1}R^{B1}$, —$NR^{A1}C(=NR^{E1})R^{B1}$, —$OC(O)NR^{A1}R^{B1}$, —$NR^{A1}C(O)OR^{B1}$, —$NR^{A1}C(O)NR^{A1}R^{B1}$, —$NR^{A1}C(S)NR^{A1}R^{B1}$, —$NR^{A1}C(=NR^{E1})NR^{A1}R^{B1}$, —$S(O)_r R^{A1}$, —$S(O)(=NR^{E1})R^{B1}$, —$N=S(O)R^{A1}R^{B1}$, —$S(O)_2 OR^{A1}$, —$OS(O)_2 R^{A1}$, —$NR^{A1}S(O)_r R^{B1}$, —$NR^{A1}S(O)(=NR^{E1})R^{B1}$, —$S(O)_r NR^{A1}R^{B1}$, —$S(O)(=NR^{E1})NR^{A1}R^{B1}$, —$NR^{A1}S(O)_2 NR^{A1}R^{B1}$, —$NR^{A1}S(O)(=NR^{E1})NR^{A1}R^{B1}$, —$P(O)R^{A1}R^{B1}$ and —$P(O)(OR^{A1})(OR^{B1})$, wherein alkyl, alkenyl, alkynyl, cycloalkyl, heterocyclyl, aryl and heteroaryl are each unsubstituted or substituted with at least one substituent, independently selected from $R^X$;
$R^2$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, —$NR^{A2}R^{B2}$, —$OR^{A2}$, —$C(O)R^{A2}$, —$C(O)OR^{A2}$, —$OC(O)R^{A2}$, —$C(O)NR^{A2}R^{B2}$, —$NR^{A2}C(O)R^{B2}$ and —$S(O)_r R^{A2}$, wherein alkyl, alkenyl, alkynyl, cycloalkyl, heterocyclyl, aryl and heteroaryl are each unsubstituted or substituted with at least one substituent, independently selected from $R^X$;
each $R^3$ and $R^{3'}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, —$NR^{A3}R^{B3}$, —$OR^{A3}$, —$C(O)R^{A3}$, —$C(O)OR^{A3}$, —$OC(O)R^{A3}$, —$C(O)NR^{A3}R^{B3}$, —$NR^{A3}C(O)R^{B3}$, and —$S(O)_r R^{A3}$, wherein alkyl, alkenyl, alkynyl, cycloalkyl, heterocyclyl, aryl and heteroaryl are each unsubstituted or substituted with at least one substituent, independently selected from $R^X$; or
"$R^2$ and $R^3$" or "$R^2$ and $R^{3'}$" together with the carbon atoms to which they are attached form a $C_{5-7}$ cycloalkyl or heterocyclic ring of 3 to 7 members containing 1, 2 or 3 heteroatoms independently selected from oxygen, sulfur, nitrogen and phosphorus, and optionally substituted with 1, 2 or 3 $R^X$ groups;
or $R^3$ and $R^{3'}$ together with the carbon atoms to which they are attached form a $C_{3-7}$ cycloalkyl or heterocyclic ring of 4 to 7 members containing 1, 2 or 3 heteroatoms independently selected from oxygen, sulfur, nitrogen and phosphorus, and optionally substituted with 1, 2 or 3 $R^X$ groups;
$R^4$ is selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, wherein alkyl, alkenyl, alkynyl, and cycloalkyl are each unsubstituted or substituted with at least one substituent, independently selected from $R^X$;
or $R^3$ and $R^4$ together with the atoms to which they are attached form a heterocyclic ring of 4 to 7 members containing 0, 1 or 2 additional heteroatoms independently selected from oxygen, sulfur, nitrogen and phosphorus, and optionally substituted with 1, 2 or 3 $R^X$ groups;
$R^5$ is selected from hydrogen, $C_{1-10}$ alkyl, $C_{2-10}$ alkenyl, $C_{2-10}$ alkynyl, $C_{3-10}$ cycloalkyl and $C_{3-10}$ cycloalkyl-$C_{1-4}$ alkyl, wherein alkyl, alkenyl, alkynyl and cycloalkyl are each unsubstituted or substituted with at least one substituent, independently selected from $R^X$;
$R^6$ is selected from hydrogen, halogen, $C_{1-10}$ alkyl, $C_{2-10}$ alkenyl, $C_{2-10}$ alkynyl, $C_{3-10}$ cycloalkyl and $C_{3-10}$ cycloalkyl-$C_{1-4}$ alkyl, wherein alkyl, alkenyl, alkynyl and cycloalkyl are each unsubstituted or substituted with at least one substituent, independently selected from $R^X$;
or $R^5$ and $R^6$ together with the atoms to which they are attached form a heterocyclic ring of 5 to 7 members containing 0, 1 or 2 additional heteroatoms independently selected from oxygen, sulfur, nitrogen and phosphorus, and optionally substituted with 1, 2 or 3 $R^X$ groups;
each $R^A$, $R^{A1}$, $R^{A2}$, $R^{A3}$, $R^{B1}$, $R^{B2}$ and $R^{B3}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^X$;
or each "$R^{A1}$ and $R^{B1}$", "$R^{A2}$ and $R^{B2}$" and "$R^{A3}$ and $R^{B3}$" together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2 or 3 $R^X$ groups;
$R^C$ and $R^D$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^X$;
or $R^C$ and $R^D$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^X$ groups;
$R^{E1}$ is selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $OR^{a1}$, $SR^{a1}$, —$S(O)_r R^{a1}$, —$C(O)R^{a1}$, $C(O)OR^{a1}$, —$C(O)NR^{a1}R^{b1}$ and —$S(O)_r NR^{a1}R^{b1}$, wherein alkyl, alkenyl, alkynyl, cycloalkyl, heterocyclyl, aryl and heteroaryl are each unsubstituted or substituted with at least one substituent, independently selected from $R^Y$;
each $R^X$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl- $C_{1-4}$ alkyl, halogen, CN, $NO_2$, $-(CR^{c1}R^{d1})_tNR^{a1}R^{b1}$, $-(CR^{c1}R^{d1})_tOR^{b1}$, $-(CR^{c1}R^{d1})_tC(O)R^{a1}$, $-(CR^{c1}R^{d1})_tC(=NR^{e1})R^{a1}$, $-(CR^{c1}R^{d1})_tC(=N-OR^{b1})R^{a1}$, $-(CR^{c1}R^{d1})_tC(O)OR^{b1}$, $-(CR^{c1}R^{d1})_tOC(O)R^{b1}$, $-(CR^{c1}R^{d1})_tC(O)NR^{a1}R^{b1}$, $-(CR^{c1}R^{d1})_tNR^{a1}C(O)R^{b1}$, $-(CR^{c1}R^{d1})_tC(=NR^{e1})NR^{a1}R^{b1}$, $-(CR^{c1}R^{d1})_tNR^{a1}C(=NR^{e1})R^{b1}$, $-(CR^{c1}R^{d1})_tOC(O)NR^{a1}R^{b1}$, $-(CR^{c1}R^{d1})_tNR^{a1}C(O)OR^{b1}$, $-(CR^{c1}R^{d1})_tNR^{a1}C(O)NR^{a1}R^{b1}$, $-(CR^{c1}R^{d1})_tNR^{a1}C(S)NR^{a1}R^{b1}$, $-(CR^{c1}R^{d1})_tNR^{a1}C(=NR^{e1})NR^{a1}R^{b1}$, $-(CR^{c1}R^{d1})_tS(O)_rR^{b1}$, $-(CR^{c1}R^{d1})_tS(O)(=NR^{e1})R^{b1}$, $-(CR^{c1}R^{d1})_tN=S(O)R^{a1}R^{b1}$, $-(CR^{c1}R^{d1})_tS(O)_2OR^{b1}$, $-(CR^{c1}R^{d1})_tOS(O)_2R^{b1}$, $-(CR^{c1}R^{d1})_tNR^{a1}S(O)_rR^{b1}$, $-(CR^{c1}R^{d1})_tNR^{a1}S(O)(=NR^{e1})R^{b1}$, $-(CR^{c1}R^{d1})_tS(O)_rNR^{a1}R^{b1}$, $-(CR^{c1}R^{d1})_tS(O)(=NR^{e1})NR^{a1}R^{b1}$, $-(CR^{c1}R^{d1})_tNR^{a1}S(O)_2NR^{a1}R^{b1}$, $-(CR^{c1}R^{d1})_tNR^{a1}S(O)(=NR^{e1})NR^{a1}R^{b1}$, $-(CR^{c1}R^{d1})_tP(O)R^{a1}R^{b1}$ and $-(CR^{c1}R^{d1})_tP(O)(OR^{a1})(OR^{b1})$, wherein alkyl, alkenyl, alkynyl, cycloalkyl, heterocyclyl, aryl and heteroaryl are each unsubstituted or substituted with at least one substituent, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^Y$;

or $R^{a1}$ and $R^{b1}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^Y$;

or $R^{c1}$ and $R^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, CN, $NO_2$, $-OR^{a2}$, $-SR^{a2}$, $-S(O)_rR^{a2}$, $-C(O)R^{a2}$, $-C(O)OR^{a2}$, $-S(O)_rNR^{a2}R^{b2}$ and $-C(O)NR^{a2}R^{b2}$;

each $R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, $-(CR^{c2}R^{d2})_tNR^{a2}R^{b2}$, $-(CR^{c2}R^{d2})_tOR^{b2}$, $-(CR^{c2}R^{d2})_tC(O)R^{a2}$, $-(CR^{c2}R^{d2})_tC(=NR^{e2})R^{a2}$, $-(CR^{c2}R^{d2})_tC(=N-OR^{b2})R^{a2}$, $-(CR^{c2}R^{d2})_tC(O)OR^{b2}$, $-(CR^{c2}R^{d2})_tOC(O)R^{b2}$, $-(CR^{c2}R^{d2})_tC(O)NR^{a2}R^{b2}$, $-(CR^{c2}R^{d2})_tNR^{a2}C(O)R^{b2}$, $-(CR^{c2}R^{d2})_tC(=NR^{e2})NR^{a2}R^{b2}$, $-(CR^{c2}R^{d2})_tNR^{a2}C(=NR^{e2})R^{b2}$, $-(CR^{c2}R^{d2})_tOC(O)NR^{a2}R^{b2}$, $-(CR^{c2}R^{d2})_tNR^{a2}C(O)OR^{b2}$, $-(CR^{c2}R^{d2})_tNR^{a2}C(O)NR^{a2}R^{b2}$, $-(CR^{c2}R^{d2})_tNR^{a2}C(S)NR^{a2}R^{b2}$, $-(CR^{c2}R^{d2})_tNR^{a2}C(=NR^{e2})NR^{a2}R^{b2}$, $-(CR^{c2}R^{d2})_tS(O)_rR^{b2}$, $-(CR^{c2}R^{d2})_tS(O)(=NR^{e2})R^{b2}$, $-(CR^{c2}R^{d2})_tN=S(O)R^{a2}R^{b2}$, $-(CR^{c2}R^{d2})_tS(O)_2OR^{b2}$, $-(CR^{c2}R^{d2})_tOS(O)_2R^{b2}$, $-(CR^{c2}R^{d2})_tNR^{a2}S(O)_rR^{b2}$, $-(CR^{c2}R^{d2})_tNR^{a2}S(O)(=NR^{e2})R^{b2}$, $-(CR^{c2}R^{d2})_tS(O)_rNR^{a2}R^{b2}$, $-(CR^{c2}R^{d2})_tS(O)(=NR^{e2})NR^{a2}R^{b2}$, $-(CR^{c2}R^{d2})_tNR^{a2}S(O)_2NR^{a2}R^{b2}$, $-(CR^{c2}R^{d2})_tNR^{a2}S(O)(=NR^{e2})NR^{a2}R^{b2}$, $-(CR^{c2}R^{d2})_tP(O)R^{a2}R^{b2}$ and $-(CR^{c2}R^{d2})_tP(O)(OR^{a2})(OR^{b2})$, wherein alkyl, alkenyl, alkynyl, cycloalkyl, heterocyclyl, aryl and heteroaryl are each unsubstituted or substituted with at least one substituent, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)N($C_{1-4}$ alkyl)$_2$, —C(O)N($C_{3-10}$ cycloalkyl)$_2$, —S(O)$_2C_{1-4}$ alkyl, —S(O)$_2C_{3-10}$ cycloalkyl, —S(O)$_2$N($C_{1-4}$ alkyl)$_2$ and —S(O)$_2$N($C_{3-10}$ cycloalkyl)$_2$;

m is selected from 0, 1, 2, 3 and 4;

n is selected from 1, 2, 3 and 4;

p is selected from 1, 2, 3 and 4;

each r is independently selected from 0, 1 and 2;

each t is independently selected from 0, 1, 2, 3 and 4;

each u is independently selected from 0, 1, 2, 3 and 4.

In another Embodiment (2), the invention provides a compound of Embodiment (1) or a pharmaceutically acceptable salt thereof, wherein n is 1 or 2 and $R^3$ and $R^{3'}$ are independently selected from hydrogen, halogen, $C_{1-10}$ alkyl, —$OR^{A3}$ and $C_{3-10}$ cycloalkyl, wherein alkyl and cycloalkyl are unsubstituted or substituted with at least one substituent independently selected from $R^X$.

In another Embodiment (3), the invention provides a compound of Embodiment (2) or a pharmaceutically acceptable salt thereof, wherein n is 1 or 2 and $R^3$ and $R^{3'}$ are independently selected from hydrogen, fluorine, methyl and OH.

In another Embodiment (4), the invention provides a compound of Embodiment (1)-(3) or a pharmaceutically acceptable salt thereof, wherein n is 1 or 2 and $R^3$ is hydrogen, shown as formula (II):

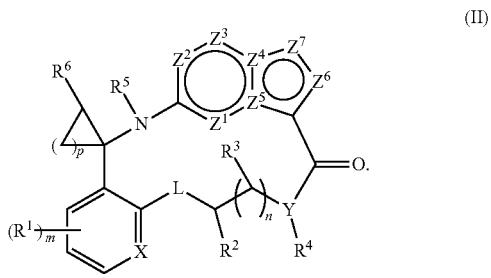

(II)

In another Embodiment (5), the invention provides a compound of Embodiment (1) or a pharmaceutically acceptable salt thereof, wherein $R^3$ and $R^{3'}$ together with the carbon atoms to which they are attached form a $C_{3-7}$ cycloalkyl or heterocyclic ring of 4 to 7 members containing 1, 2 or 3 heteroatoms independently selected from oxygen, sulfur, nitrogen and phosphorus, and optionally substituted with 1, 2 or 3 $R^X$ groups.

In another Embodiment (6), the invention provides a compound of Embodiment (5) or a pharmaceutically acceptable salt thereof, wherein $R^3$ and $R^{3'}$ together with the carbon atoms to which they are attached form cyclopropyl or cyclobutyl.

In another Embodiment (7), the invention provides a compound of Embodiment (1)-(6) or a pharmaceutically acceptable salt thereof, wherein X is CH.

In another Embodiment (8), the invention provides a compound of Embodiment (1)-(6) or a pharmaceutically acceptable salt thereof, wherein X is N.

In another Embodiment (9), the invention provides a compound of any one of Embodiments (1)-(8) or a pharmaceutically acceptable salt thereof, wherein $R^1$ is selected from $C_{1-10}$ alkyl, $C_{3-10}$ cycloalkyl, halogen and CN, wherein alkyl and cycloalkyl are unsubstituted or substituted with at least one substituent independently selected from $R^X$.

In another Embodiment (10), the invention provides a compound of Embodiment (9) or a pharmaceutically acceptable salt thereof, wherein $R^1$ is fluorine and m is 1.

In another Embodiment (11), the invention provides a compound of any one of Embodiments (1)-(10) or a pharmaceutically acceptable salt thereof, wherein L is selected from —($CR^CR^D$)$_u$O($CR^CR^D$)$_t$—, —$CR^CR^D$—, —$NR^A$— and —($CR^CR^D$)$_u$S($CR^CR^D$)$_t$.

In another Embodiment (12), the invention provides a compound of Embodiment (11) or a pharmaceutically acceptable salt thereof, wherein L is selected from —O—, —$CH_2$—, —NH— and —S—.

In another Embodiment (13), the invention provides a compound of any one of Embodiments (1)-(12) or a pharmaceutically acceptable salt thereof, wherein $R^2$ is independently selected from hydrogen, $C_{1-10}$ alkyl and $C_{3-10}$ cycloalkyl, wherein alkyl and cycloalkyl are unsubstituted or substituted with at least one substituent independently selected from $R^X$.

In another Embodiment (14), the invention provides a compound of Embodiment (13) or a pharmaceutically acceptable salt thereof, wherein $R^2$ is selected from hydrogen and methyl.

In another Embodiment (15), the invention provides a compound of any one of Embodiments (1)-(14) or a pharmaceutically acceptable salt thereof, wherein Y is O and $R^4$ is absent.

In another Embodiment (16), the invention provides a compound of any one of Embodiments (1)-(14) or a pharmaceutically acceptable salt thereof, wherein Y is N.

In another Embodiment (17), the invention provides a compound of Embodiment (16) or a pharmaceutically acceptable salt thereof, wherein $R^4$ is selected from hydrogen, $C_{1-10}$ alkyl and $C_{3-10}$ cycloalkyl, wherein alkyl and cycloalkyl are unsubstituted or substituted with at least one substituent independently selected from $R^X$.

In another Embodiment (18), the invention provides a compound of Embodiment (17) or a pharmaceutically acceptable salt thereof, wherein $R^4$ is selected from hydrogen and methyl.

In another Embodiment (19), the invention provides a compound of any one of Embodiments (1)-(16) or a pharmaceutically acceptable salt thereof, wherein $R^3$ and $R^4$ together with the atoms to which they are attached form a heterocyclic ring of 4 to 7 members containing 0, 1 or 2 additional heteroatoms independently selected from oxygen, sulfur, nitrogen and phosphorus, and optionally substituted with $R^X$.

In another Embodiment (20), the invention provides a compound of Embodiment (19) or a pharmaceutically acceptable salt thereof, wherein $R^3$ and $R^4$ together with the atoms to which they are attached form

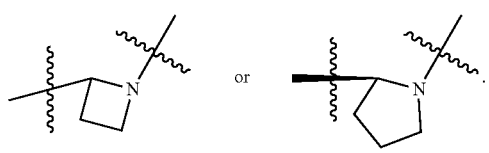

In another Embodiment (21), the invention provides a compound of any one of Embodiments (1)-(20) or a pharmaceutically acceptable salt thereof, wherein $R^5$ and $R^6$ are independently selected from hydrogen, $C_{1-10}$ alkyl, $C_{3-10}$ cycloalkyl and heterocyclyl, wherein alkyl, cycloalkyl and heterocyclyl are each unsubstituted or substituted with at least one substituent independently selected from $R^x$.

In another Embodiment (22), the invention provides a compound of Embodiment (21) or a pharmaceutically acceptable salt thereof, wherein $R^5$ and $R^6$ are independently selected from hydrogen, methyl, $CD_3$ and ethyl.

In another Embodiment (23), the invention provides a compound of any one of Embodiments (1)-(20) or a pharmaceutically acceptable salt thereof, wherein $R^5$ and $R^6$ together with the atoms to which they are attached form a heterocyclic ring of 5 to 7 members containing 0, 1 or 2 additional heteroatoms independently selected from oxygen, sulfur, nitrogen and phosphorus, and optionally substituted with $R^x$.

In another Embodiment (24), the invention provides a compound of Embodiment (23) or a pharmaceutically acceptable salt thereof, wherein $R^5$ and $R^6$ together with the atoms to which they are attached form a 5-6 membered heterocyclic ring without additional heteroatom.

In another Embodiment (25), the invention provides a compound of Embodiment (24) or a pharmaceutically acceptable salt thereof, wherein the substructure of Formula (III)

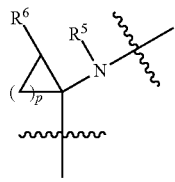

in Formula (I) is

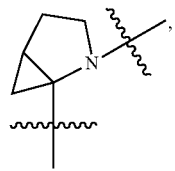 [SMILES: *N1CCC2CC21*]

wherein the ⌇ symbol indicates the point of attachment to the rest of the molecule.

In another Embodiment (26), the invention provides a compound of any one of Embodiments (1)-(24) or a pharmaceutically acceptable salt thereof, wherein p is 1.

In another Embodiment (27), the invention provides a compound of any one of Embodiments (1)-(26) or a pharmaceutically acceptable salt thereof, wherein $Z^4$ is N and $Z^5$ is C.

In another Embodiment (28), the invention provides a compound of any one of Embodiments (1)-(26) or a pharmaceutically acceptable salt thereof, wherein $Z^4$ is C and $Z^5$ is N.

In another Embodiment (29), the invention provides a compound of any one of Embodiments (1)-(28) or a pharmaceutically acceptable salt thereof, wherein Z and Z are N, and $Z^2$, $Z^3$ and $Z^6$ are $CR^x$, $R^x$ is selected from hydrogen, halogen, OH, CN, $NO_2$, $C_{1-10}$ alkyl, $C_{3-10}$ cycloalkyl, $C_{3-10}$ cycloalkyl-$C_{1-4}$ alkyl, heterocyclyl, heteroaryl-$C_{1-4}$ alkyl, $—(CR^{c1}R^{d1})_tNR^{a1}R^{b1}$ and $—(CR^{c1}R^{d1})_tNR^{a1}C(O)R^{b1}$.

In another Embodiment (30), the invention provides a compound of Embodiment (29) or a pharmaceutically acceptable salt thereof, wherein $R^x$ is selected from hydrogen, $NH_2$,

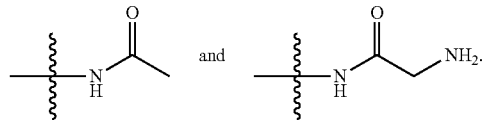

In another Embodiment (31), the invention provides a compound selected from

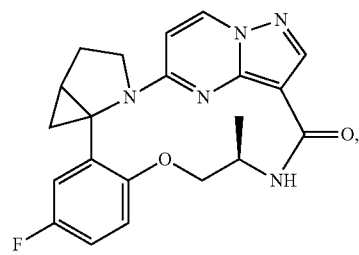

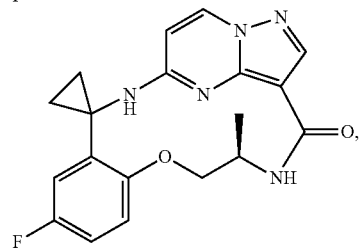

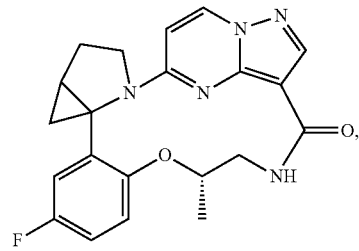

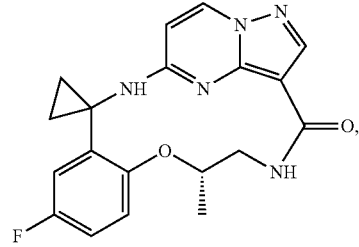

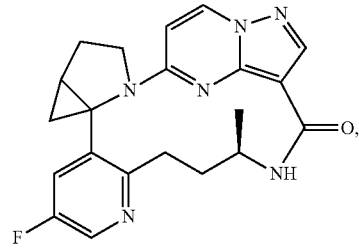

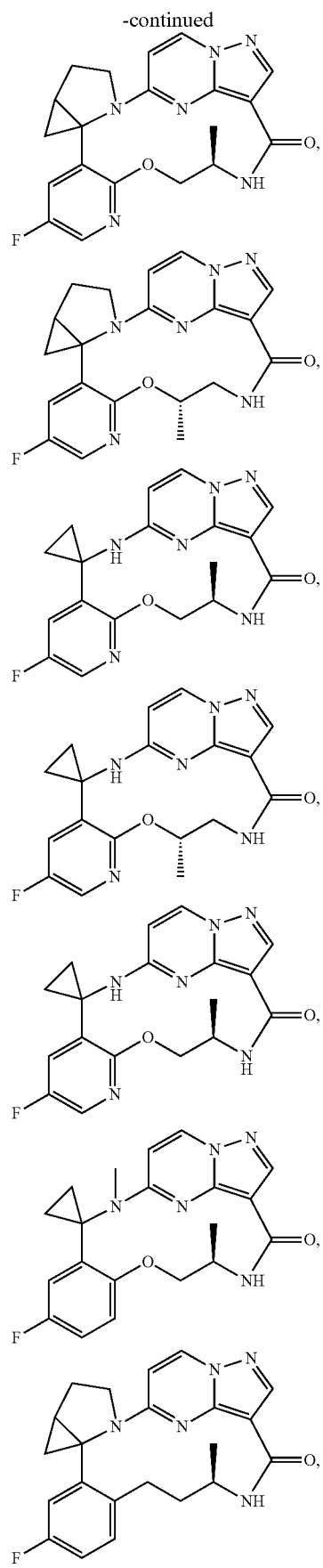
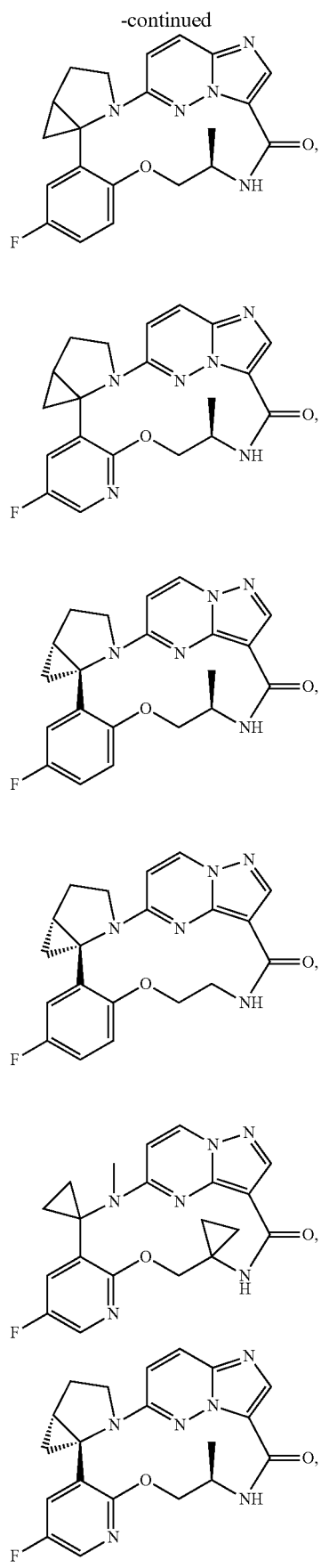

29
-continued
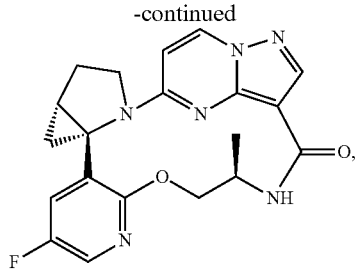
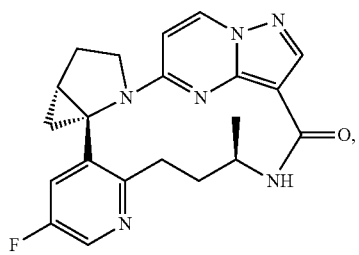
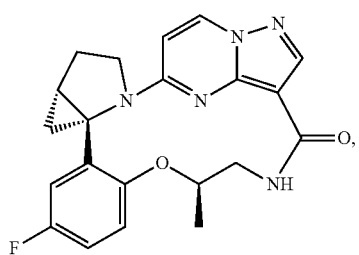
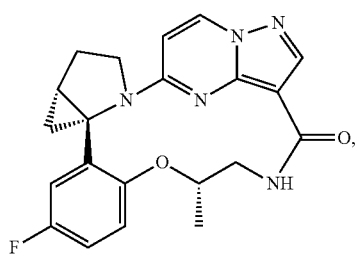
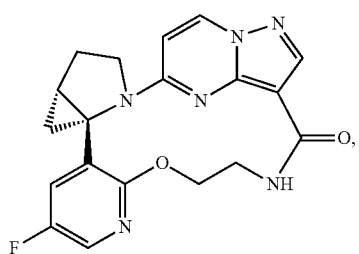
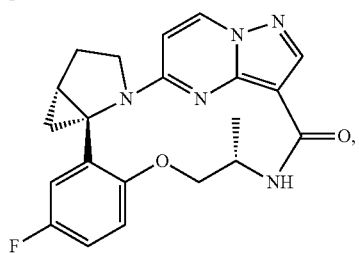
30
-continued
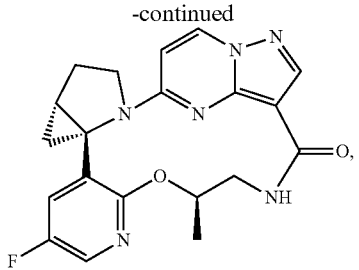
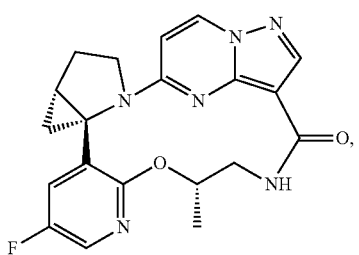
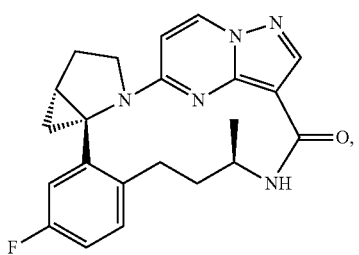
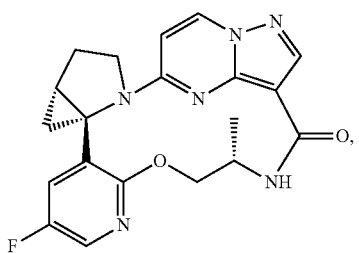
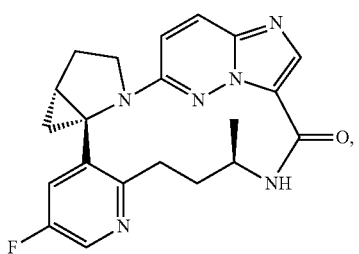
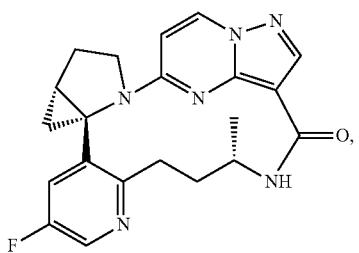

31
-continued
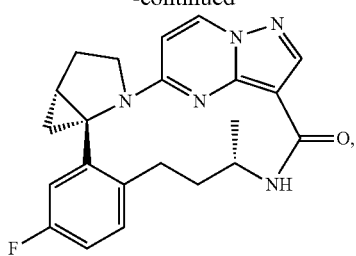
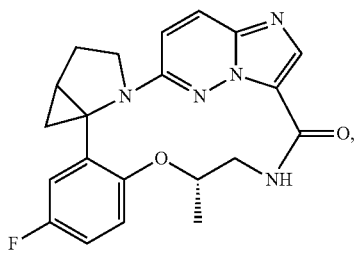
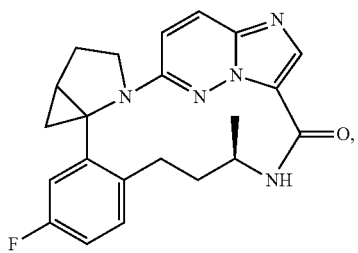
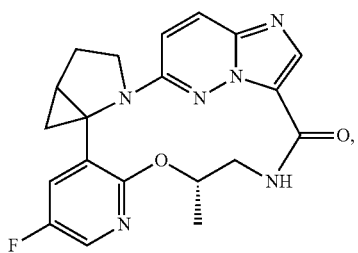
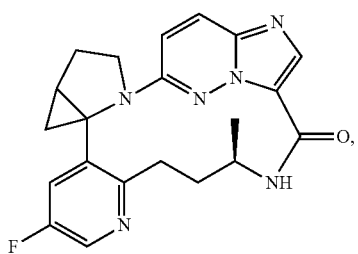
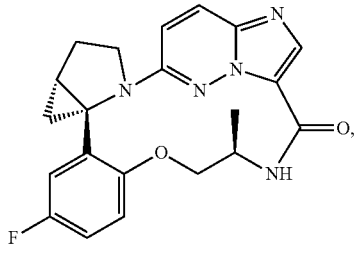
32
-continued
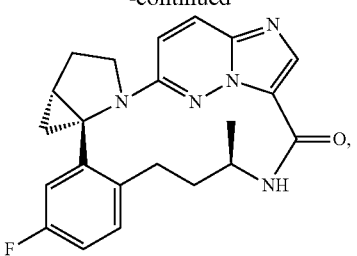
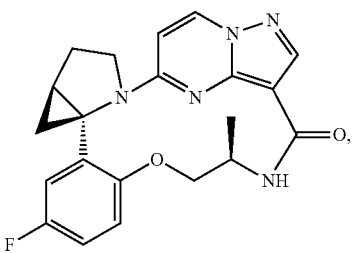
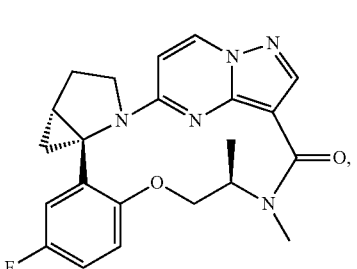
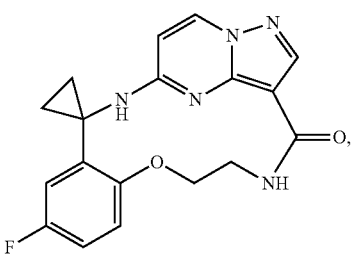
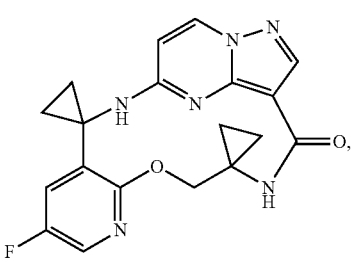
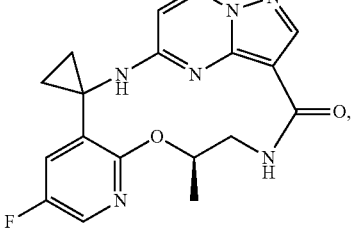

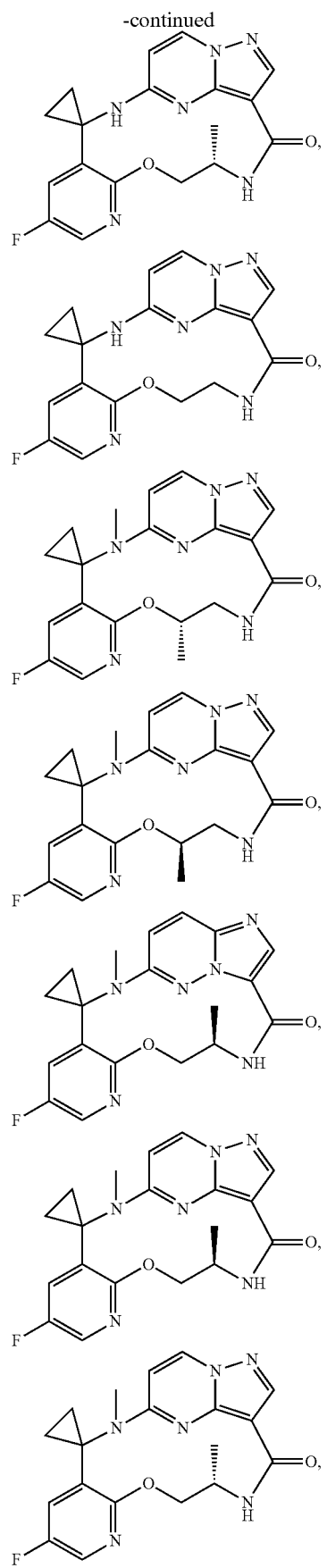
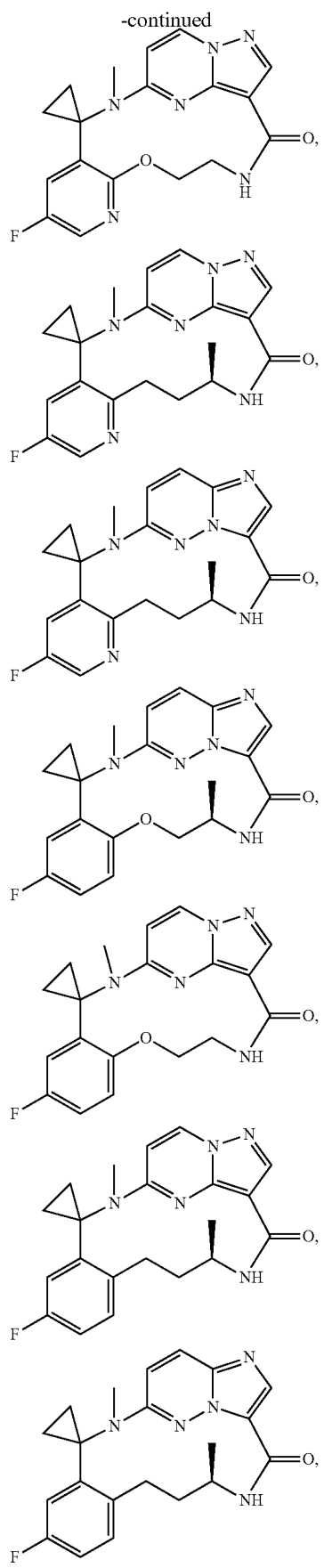

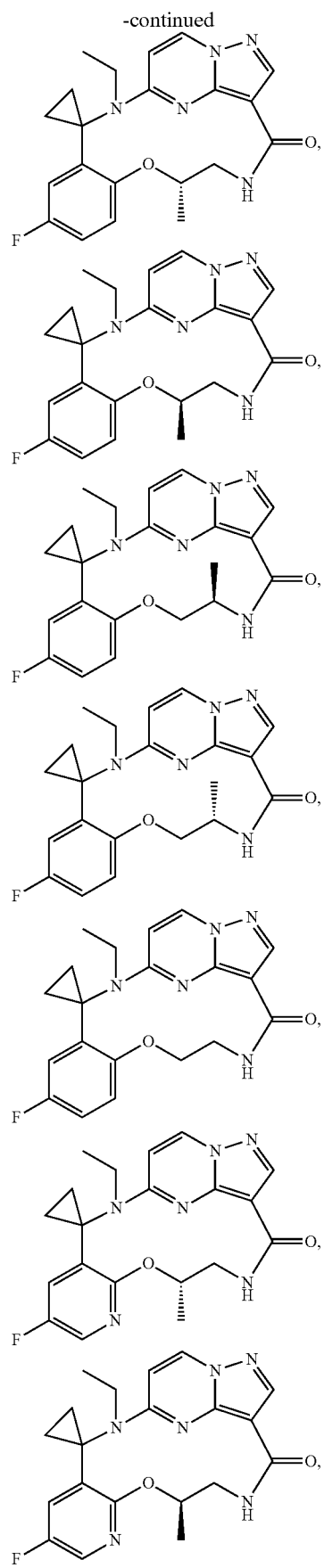
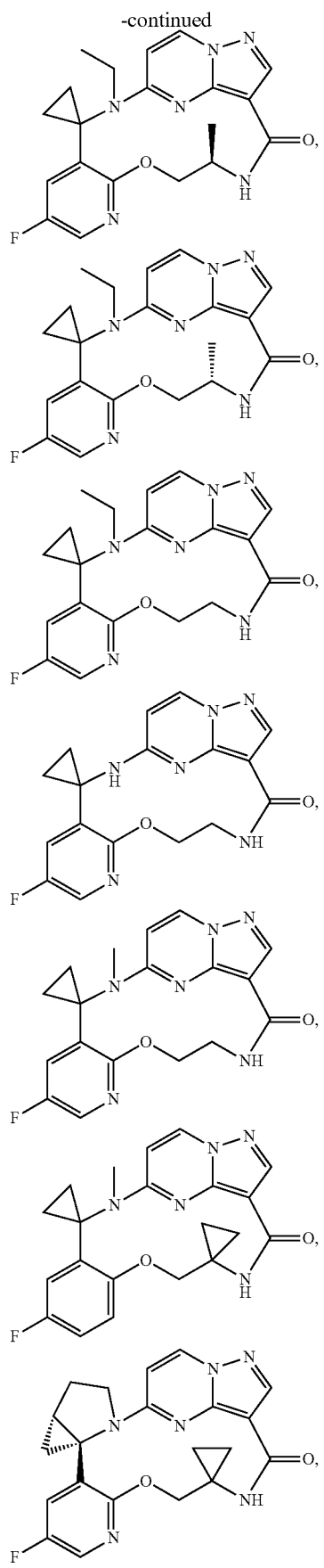

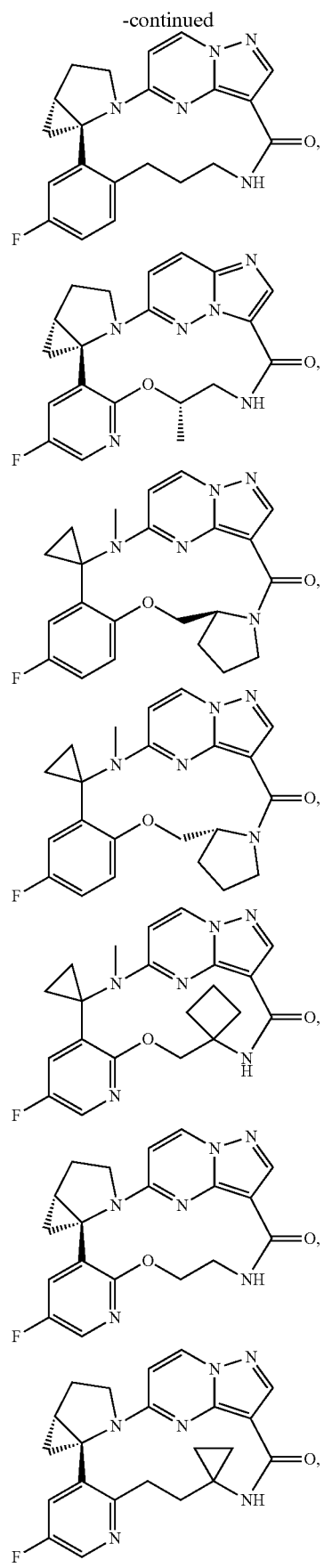
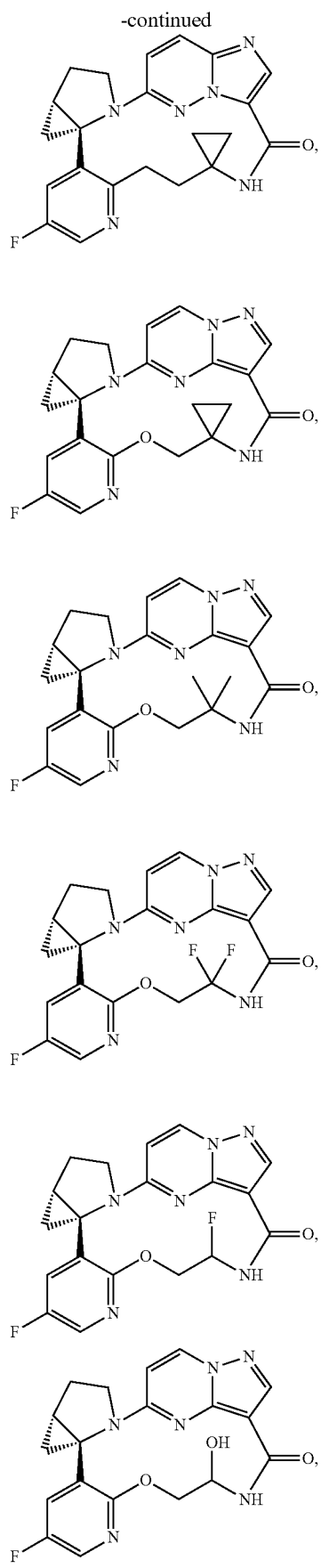

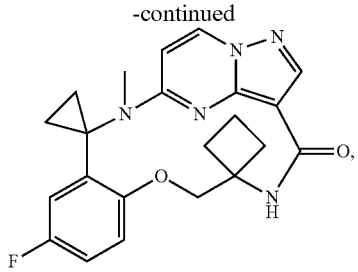
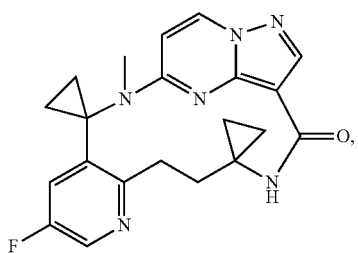
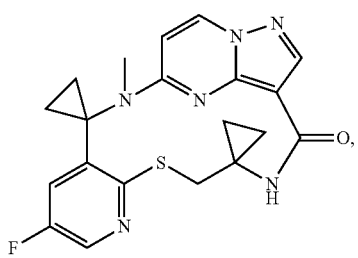
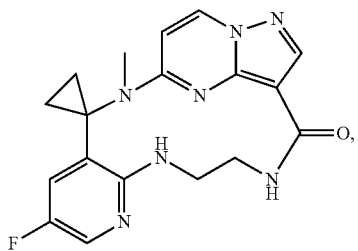
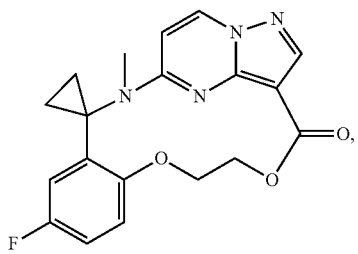
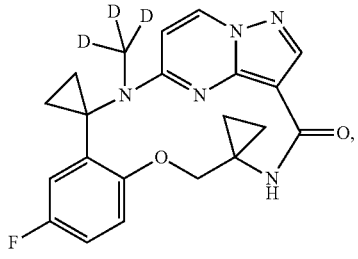
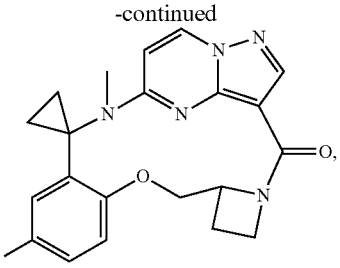
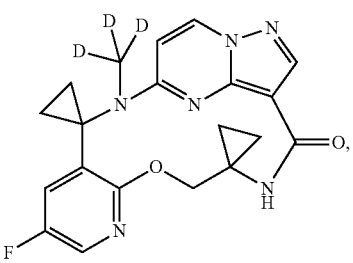
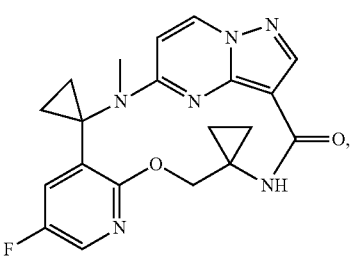
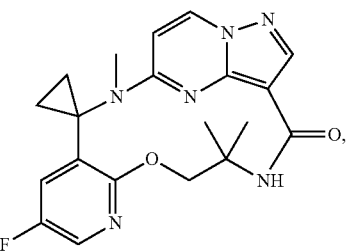
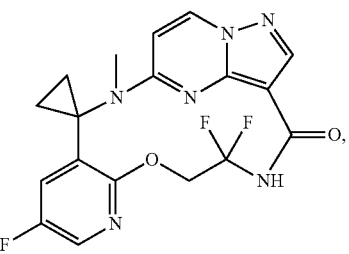
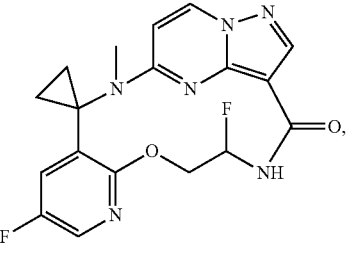

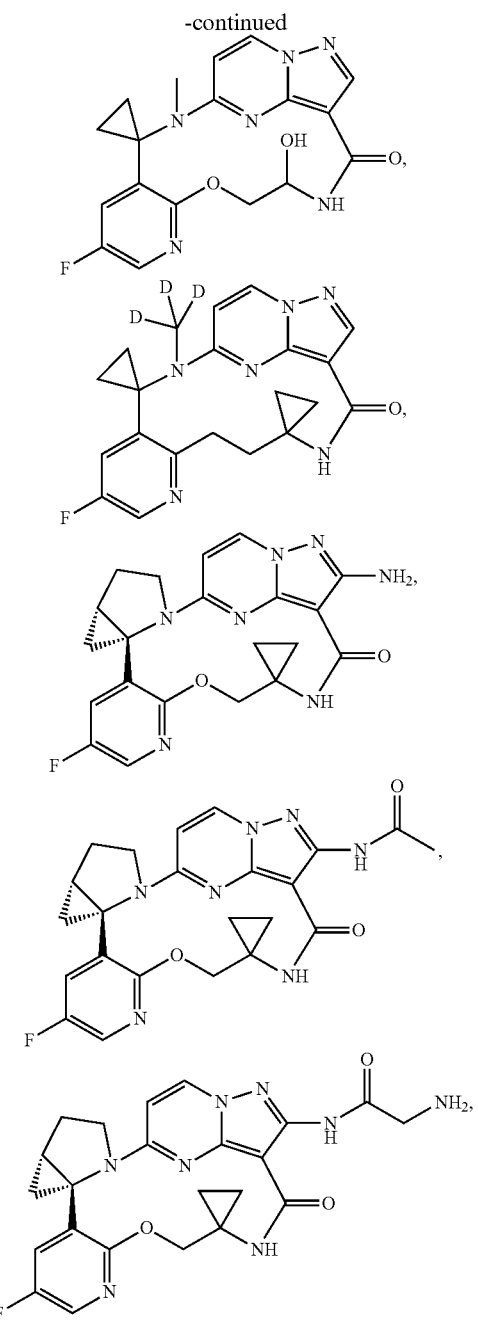

and pharmaceutically acceptable salts thereof.

In another Embodiment (32), the invention provides a pharmaceutical composition comprising a compound of any one of Embodiments (1) to (31) or a pharmaceutically acceptable salt thereof and at least one pharmaceutically acceptable carrier.

In another Embodiment (33), the invention provides a method of treating, ameliorating or preventing a condition, which responds to inhibition of TRK, comprising administering to a subject in need of such treatment an effective amount of a compound of any one of Embodiments (1) to (31), or a pharmaceutically acceptable salt thereof, or a pharmaceutical composition thereof, and optionally in combination with a second therapeutic agent.

In another Embodiment (34), the invention provides a use of a compound of any one of Embodiments (1) to (31) or a pharmaceutically acceptable salt thereof in the preparation of a medicament for treating a cell-proliferative disorder.

In yet another of its aspects, there is provided a kit comprising a compound disclosed herein, or a pharmaceutically acceptable salt thereof; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound disclosed herein, or a pharmaceutically acceptable salt thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound disclosed herein, or a pharmaceutically acceptable salt thereof.

In another of its aspects, there is provided a method of inhibiting a TRK comprising contacting the TRK with a compound disclosed herein, or a pharmaceutically acceptable salt thereof.

In yet another of its aspects, there is provided a method of inhibiting a TRK comprising causing a compound disclosed herein, or a pharmaceutically acceptable salt thereof to be present in a subject in order to inhibit the TRK in vivo.

In a further of its aspects, there is provided a method of inhibiting TRK comprising administering a first compound to a subject that is converted in vivo to a second compound wherein the second compound inhibits the TRK in vivo, the second compound being a compound according to any one of the above embodiments and variations.

In another of its aspects, there is provided a method of treating a disease state for which a TRK possesses activity that contributes to the pathology and/or symptomology of the disease state, the method comprising causing a compound disclosed herein, or a pharmaceutically acceptable salt thereof to be present in a subject in a therapeutically effective amount for the disease state.

In a further of its aspects, there is provided a method of treating a disease state for which a TRK possesses activity that contributes to the pathology and/or symptomology of the disease state, the method comprising administering a first compound to a subject that is converted in vivo to a second compound wherein the second compound inhibits the TRK in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, exzema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another of its aspects, there is provided a method of treating a disease state for which a mutation in the TRK gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament. In yet another of its aspects, the present invention relates to the use of a compound according to any one of the above embodiments and variations in the manufacture of a medicament for inhibiting a TRK.

In a further of its aspects, the present invention relates to the use of a compound according to any one of the above embodiments and variations in the manufacture of a medicament for treating a disease state for which a TRK possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGFYOF® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethyl cellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

Combination Therapies

The compounds or pharmaceutical acceptable salts of the disclosure may be administered as the sole therapy, or together with other therapeutic agent or agents.

For example, the therapeutic effectiveness of one of the compounds described herein may be enhanced by administration of an adjuvant (i.e. by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or the individual may experience a synergistic benefit.

In the instances where the compounds described herein are administered in combination with other therapeutic agents, the compounds described herein may be administered in the same pharmaceutical composition as other therapeutic agents, or because of different physical and chemical characteristics, be administered by a different route. For example, the compounds described herein may be administered orally to generate and maintain good blood levels thereof, while the other therapeutic agent may be administered intravenously. Thus the compounds described herein may be administered concurrently, sequentially or dosed separately to other therapeutic agents.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

EXAMPLES

Various methods may be developed for synthesizing a compound of formula (I)/(II) or a pharmaceutically acceptable salt thereof. Representative methods for synthesizing a compound of formula (I)/(II) or a pharmaceutically acceptable salt thereof are provided in the Examples. It is noted, however, that a compound of formula (I)/(II) or a pharmaceutically acceptable salt thereof may also be synthesized by other synthetic routes that others may devise.

It will be readily recognized that certain compounds of formula (I)/(II) have atoms with linkages to other atoms that confer a particular stereochemistry to the compound (e.g., chiral centers). It is recognized that synthesis of a compound of formula (I)/(II) or a pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

A compound of formula (I)/(II) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I)/(II) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I)/(II) are set forth in the definitions section of this Application. Alternatively, the salt forms of the compounds of formula (I)/(II) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of a compound of formula (I) or a pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in a suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T.W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); µL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxy ethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Bruker AV 600. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet) and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60F-254), visualized with UV light, 5% ethanolic phosphomolybdic acid, ninhydrin, or p-anisaldehyde solution. Flash column chromatography was performed on silica gel (200-300 mesh, Branch of Qingdao Haiyang Chemical Co., Ltd).

Synthetic Schemes

A compound of formula (I)/(II) or a pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described herein after it may be necessary to protect reactive functional groups, for example hydroxyl, amino, imino, thio or carboxyl groups, where these are desired in the final product, to avoid their unwanted participation in the reactions. Conventional protecting groups may be used in accordance with standard practice, for examples see T.W. Greene and P. G. M. Wuts in "Protective Groups in Organic Chemistry" John Wiley and Sons, 1991.

Synthetic methods for preparing the compounds of the present invention are illustrated in the following Schemes and Examples. Starting materials are commercially available or may be made according to procedures known in the art or as illustrated herein.

The intermediates shown in the following schemes are either known in the literature or may be prepared by a variety of methods familiar to those skilled in the art.

As an illustration, one synthesis of compounds of formula (I)/(II) of the present disclosure is shown in Scheme 1. Starting from the intermediates III, which is either commercially available or known in the literature. Intermediate of formula V is prepared by the coupling of III with the intermediates IV using such coupling conditions as Buchwald amination reaction or amination conditions known in the literature. Intermediate of formula VII can be obtained from the appropriately functionalized intermediates V via substitution or cross coupling reactions with intermediates of formula VI. Sequential Hydrolysis of ester VII gives carboxylic acid VIII. Finally, the compounds of formula (I)/(II) can be prepared from VIII by the cleavage of the protecting group and intramolecular cyclization reaction in the presence of coupling reagents.

Scheme 1

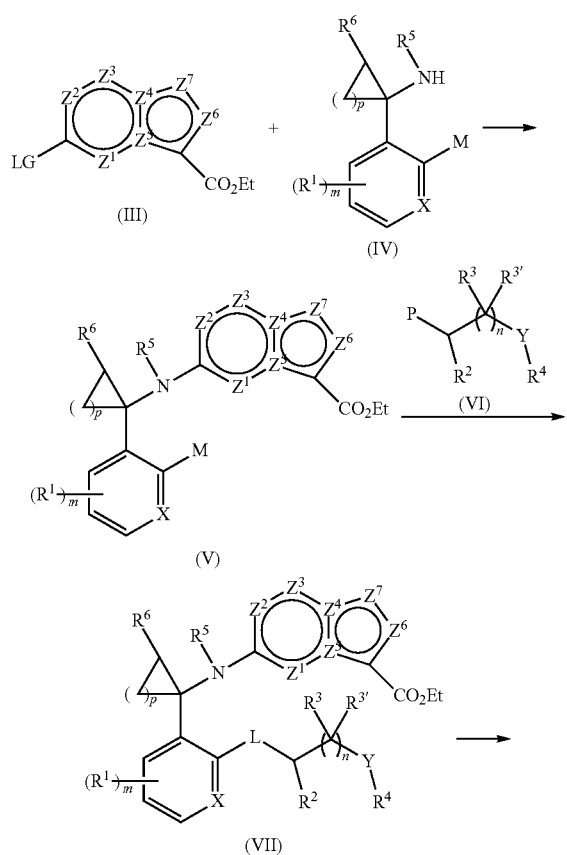

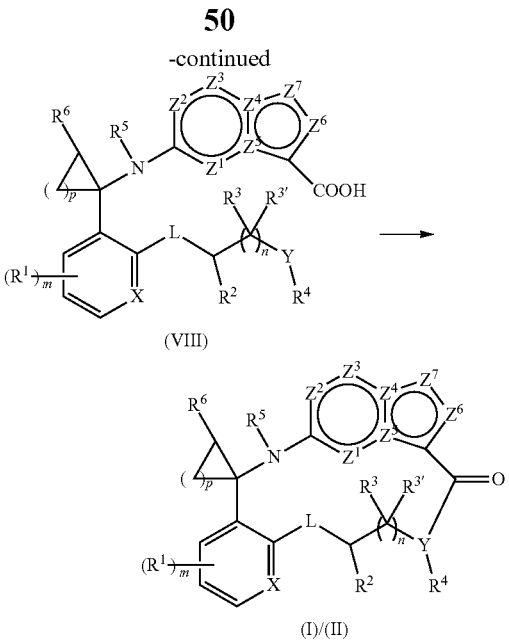

M = O-protecting group, hydroxyl group, or leaving group
P = Reactive functional group, for example hydroyl, amino, thio, alkynyl group, or leaving group
LG = Leaving group As an illustration of the preparation of intermediates of formula IV, one synthetic route of compounds of formula IVa is shown in Scheme 2. Starting from IVa-A, which is either commercially available or known in the literature. Amino alcohols IVa-B can be prepared by treating IVa-A with but-3-en-1-ol via Kulinkovich reaction. Selective protection of amino group gives compounds of formula IVa-C which can be further transformed into IVa-D. Finally, Intermediate of formula IVa can be obtained from IVa-D through intramolecular cyclization in the presence of a base followed by deprotection of the protecting group on the amino.

Scheme 2

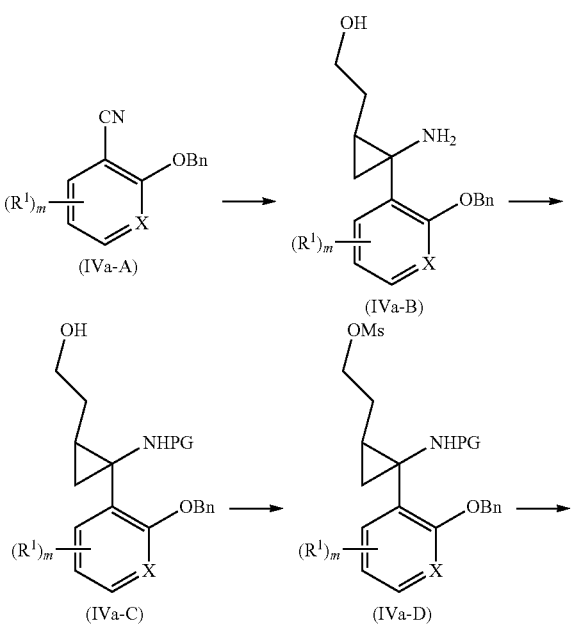

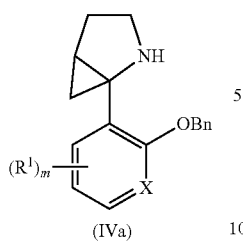

(IVa)

PG = Protecting group

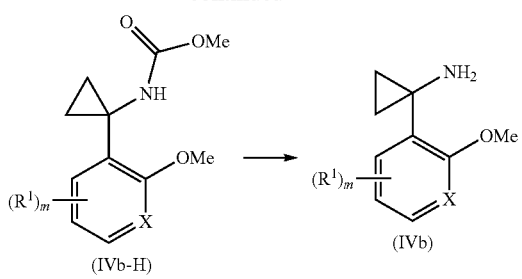

As a further illustration of the preparation of intermediates of formula IV, a preparation of compound of formula IVb is illustrated in Scheme 3. Starting from IVb-A, which is either commercially available or known in the literature. Hydrolysis of of IVb-A results in carboxylic acid IVb-B, and then reduction of IVb-B provides IVb-C. Intermediate of formula IVb-F can be obtained via a three-step sequence of mesylation of hydroxyl group of IVb-C, substitution reaction and cyclopropanation reaction. Hydrolysis of IVb-F gives compounds of formula IVb-G which can be further transformed into IVb-H via Curtius rearrangement. Finally, selective deprotecting of IVb-H leads to compounds of formula IVb.

Another illustration of the preparation of intermediates of formula IV is shown is Scheme 4 which demonstrates preparation of compound of formula IVc. Starting from IVc-A, which is either commercially available or known in the literature. Lactone IVc-B can be prepared by treating IVc-A with (5)-2-(chloromethyl)oxirane. Ammonolysis of IVc-B gives compounds of formula IVc-C which can be further transformed into compounds of formula IVc-D via Curtius rearrangement followed by intramolecular cyclization. Hydrolysis of IVc-D results in amino alcohols IVc-E. Selective protection of the amino group in IVc-E leads to IVc-F. Mesylation of the hydroxyl group in IVc-F into a leaving Group gives IVc-G which can be further transformed into compounds of formula IVc-H through a substitution reaction. Lactam IVc-K can be obtained via a three-step sequence of conversion of the cyano group in IVc-H into the amide group, the cleavage of the protecting groups of IVc-I and intramolecular cyclization. Finally, the reduction of lactam IVc-K leads to compounds of formula IVc.

Scheme 3

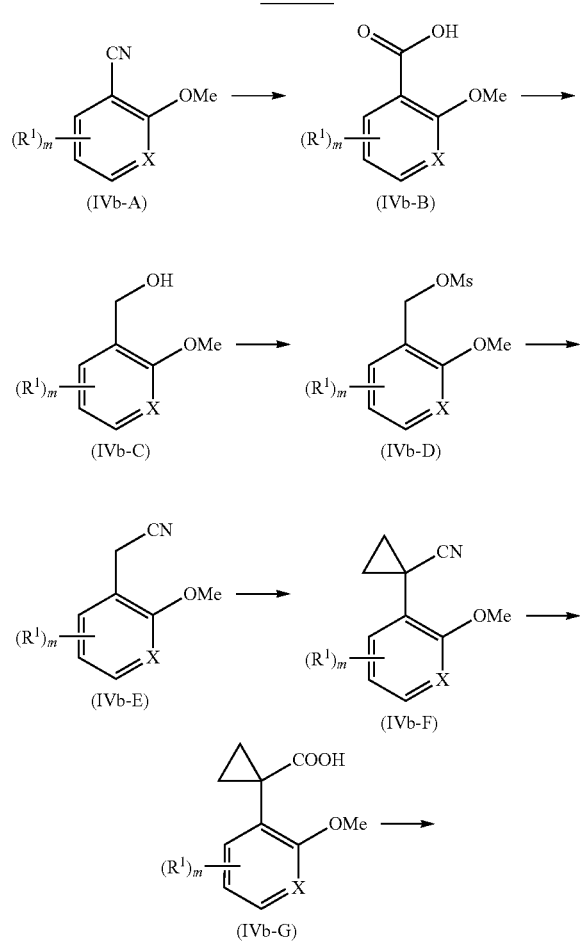

Scheme 4

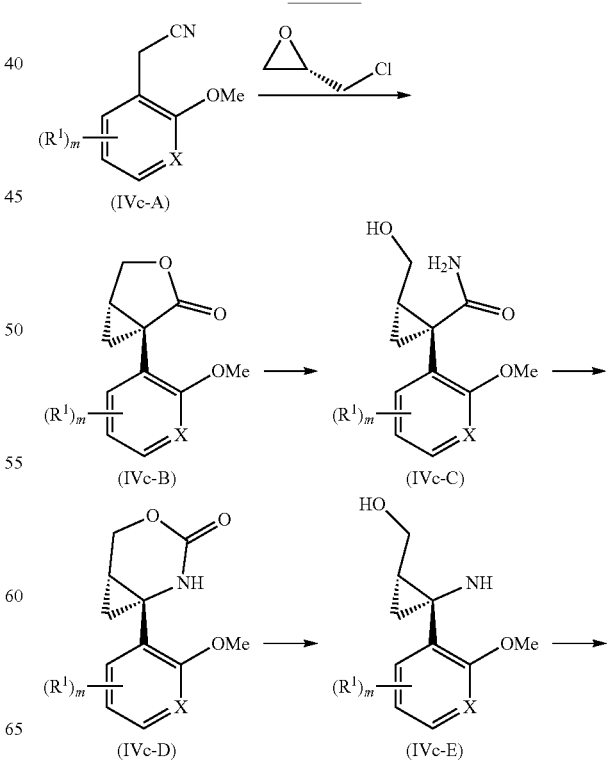

-continued

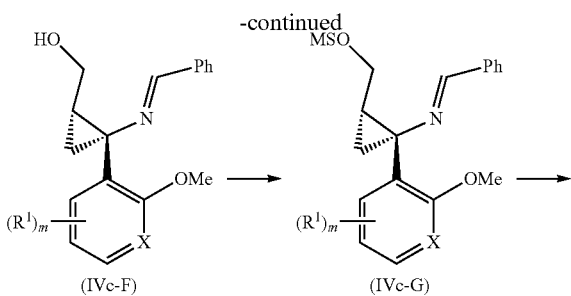

(IVc-F) → (IVc-G) → (IVc-H) → (IVc-I) → (IVc-J) → (IVc-K) → (IVc)

In some cases, the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Preparation of Intermediates

Intermediate A 1-(5-Fluoro-2-hydroxyphenyl)-2-azabicyclo[3.1.0]hexan-2-ium trifluoroacetate (A)

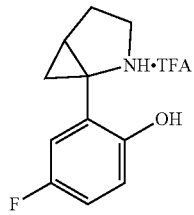

2-(Benzyloxy)-5-fluorobenzonitrile (A-1)

The title compound 2-(benzyloxy)-5-fluorobenzonitrile (A-1) was prepared according to the method described in WO 2007/89646.

2-(2-Amino-2-(2-(benzyloxy)-5-fluorophenyl)cyclopropyl)ethan-1-ol (A-2)

To a solution of Ti(O-i-Pr)$_4$ (4.80 mL, 16.0 mmol) in Et$_2$O (40 mL) was added cyclohexylmagnesium chloride (20.0 mL, 40.0 mmol) dropwise at −78° C. and the resulting mixture was stirred at −78° C. for 20 min. Then a solution of but-3-en-1-ol (0.668 mL, 8.0 mmol) and 2-(benzyloxy)-5-fluorobenzonitrile (A-1) (3.64 g, 16.0 mmol) in Et$_2$O (430 mL) was added to the mixture. The reaction mixture was warmed to RT, and stirred at RT for overnight. The mixture was cooled to 0° C., quenched with 1 N NaOH aqueous solution and extracted with EtOAc (2×100 mL). The organic phase was washed sequentially with water (20 mL) and brine (20 mL), dried over Na$_2$SO$_4$ and concentrated. The residue was purified by column chromatography on silica gel, eluting with PE/EtOAc (3:1~1:3) to give the title compound 2-(2-amino-2-(2-(benzyloxy)-5-fluorophenyl)cyclopropyl)ethan-1-ol (A-2). MS-ESI (m/z): 302 [M+1]$^+$.

tert-Butyl (1-(2-(benzyloxy)-5-fluorophenyl)-2-(2-hydroxyethyl)cyclopropyl) carbamate (A-3)

To a solution of 2-(2-amino-2-(2-(benzyloxy)-5-fluorophenyl)cyclopropyl)ethan-1-ol (A-2) (1.10 g, 3.66 mmol) in DCM (26 mL) was added (Boc)$_2$O (0.958 g, 4.39 mmol) and Et$_3$N (1.02 mL, 7.3 mmol) at 0° C. After addition, the mixture was warmed to RT and stirred at RT for overnight. The reaction was quenched with water, and the mixture was extracted with DCM. The extracts were washed with brine, dried over Na$_2$SO$_4$, and concentrated. The residue was purified by column chromatography on silica gel, eluting with PE/EtOAc (5:1~2:1) to give the title compound tert-butyl (1-(2-(benzyloxy)-5-fluorophenyl)-2-(2-hydroxyethyl)cyclopropyl) carbamate (A-3). MS-ESI (m/z): 402 [M+1]$^+$.

2-(2-(2-(Benzyloxy)-5-fluorophenyl)-2-((tert-butoxycarbonyl)amino)cyclopropyl) ethyl methane sulfonate (A-4)

To a solution of tert-butyl (1-(2-(benzyloxy)-5-fluorophenyl)-2-(2-hydroxyethyl)cyclopropyl)carbamate (A-3) (1.10 g, 2.74 mmol) in DCM (30 mL) was added MsCl (0.300 mL, 4.65 mmol) and Et$_3$N (1.02 mL, 7.3 mmol) at 0° C. The mixture was stirred at 0° C. for 40 min. The reaction was quenched with water and extracted with DCM. The extracts were washed sequentially with water, 0.5 N HCl and brine, dried over Na$_2$SO$_4$, and concentrated to give the title compound 2-(2-(2-(benzyloxy)-5-fluorophenyl)-2-((tert-butoxycarbonyl)amino)-cyclopropyl)ethyl methanesulfonate (A-4). MS-ESI (m/z): 480 [M+1]$^+$.

tert-Butyl 1-(2-(benzyloxy)-5-fluorophenyl)-2-azabicyclo[3.1.0]hexane-2-carboxylate (A-5)

To a solution of 2-(2-(2-(benzyloxy)-5-fluorophenyl)-2-((tert-butoxycarbonyl)-amino)cyclopropyl)ethyl methanesulfonate (A-4) (1.27 g, 2.65 mmol) in DMF (15 mL) was added NaH (159 mg, 4.00 mmol) at 0° C. After addition, the mixture was warmed to RT and stirred at RT for 1.5 h. The reaction was cooled to 0° C., quenched with water and extracted with EtOAc. The extracts were washed with water and brine, dried over Na$_2$SO$_4$, and concentrated. The residue was purified by column chromatography on silica gel, eluting with PE/EtOAc (12:1~5:1) to give the title compound tert-butyl 1-(2-(benzyloxy)-5-fluorophenyl)-2-azabicyclo[3.1.0]hexane-2-carboxylate (A-5). MS-ESI (m/z): 384 [M+1]$^+$.

tert-Butyl 1-(5-fluoro-2-hydroxyphenyl)-2-azabicyclo[3.1.0]hexane-2-carboxylate (A-6)

The mixture of tert-butyl 1-(2-(benzyloxy)-5-fluorophenyl)-2-azabicyclo[3.1.0]-hexane-2-carboxylate (A-5) (0.19 g, 0.50 mmol) and Pd/C (10%, 190 mg) in MeOH (20 mL) was stirred at RT for overnight at the atmosphere of H$_2$ (1 atm). Then the mixture was filtered, and the filtrate was concentrated to give the title compound tert-butyl 1-(5-fluoro-2-hydroxyphenyl)-2-azabicyclo[3.1.0]hexane-2-carboxylate (A-6). MS-ESI (m/z): 294 [M+1]$^+$.

1-(5-Fluoro-2-hydroxyphenyl)-2-azabicyclo[3.1.0]hexan-2-iumtrifluoroacetate (A)

To a solution of tert-butyl 1-(5-fluoro-2-hydroxyphenyl)-2-azabicyclo[3.1.0]hexane-2-carboxylate (A-6) (12.6 mg, 0.043 mmol) in DCM (1.5 mL) was added TFA (0.5 mL). The mixture was stirred at RT for 0.5 h, and concentrated to give 1-(5-fluoro-2-hydroxyphenyl)-2-azabicyclo[3.1.0]hexan-2-ium trifluoroacetate (A) as crude, which was used in next step without further purification. MS-ESI (m/z): 194 [M+1]$^+$.

Intermediate B 1-(2-(Benzyloxy)-5-fluorophenyl)cyclopropan-1-amine (B)

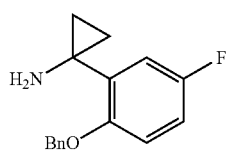

To a solution of 2-(benzyloxy)-5-fluorobenzonitrile (A-1) (1.13 g, 5.00 mmol) in Et$_2$O (25 mL) was added Ti(O-i-Pr)$_4$ (1.81 mL, 5.50 mmol) and EtMgCl (11.0 mL, 11.0 mmol) dropwise at −78° C. and the resulting mixture was stirred at −78° C. for 1 h. The reaction mixture was warmed to RT. Then BF$_3$.OEt$_2$ (1.27 mL, 10.0 mmol) was added, the mixture was stirred at RT for 1 h. The mixture was quenched with 1 N HCl aqueous solution (15 mL), then 10% NaOH aqueous solution (45 mL) was added. The mixture was extracted with EtOAc (2×50 mL). The organic phase was washed sequentially with water (20 mL) and brine (20 mL), dried and concentrated. The residue was purified by column chromatography on silica gel, eluting with PE/EtOAc (5:1~1:1) to give the title compound 1-(2-(benzyloxy)-5-fluorophenyl)cyclopropan-1-amine (B). MS-ESI (m/z): 258 [M+1]$^+$.

Intermediate C 1-(2-(Benzyloxy)-5-fluoropyridin-3-yl)-2-azabicyclo[3.1.0]hexane trifluoroacetate (C)

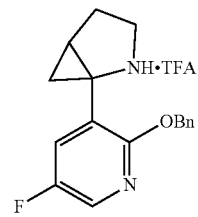

2-(Benzyloxy)-5-fluoro Nicotinonitrile (C-1)

To a solution of 2-chloro-5-fluoronicotinonitrile (1.57 g, 10.0 mmol) and phenylmethanol (1.20 g, 11.0 mmol) in dioxane (100 mL) was added Pd(OAc)$_2$ (225 mg, 1.00 mmol), Cs$_2$CO$_3$ (4.89 g, 15.0 mmol) and [1,1'-binaphthalen]-2-yldi-tert-butylphosphane (800 mg, 2.00 mmol). Then the resulting mixture was heated at 70° C. for 4 h at the atmosphere of N$_2$. The mixture was concentrated and the residue was purified by column chromatography on silica gel, eluting with PE/EtOAc (50:1) to give the title compound 2-(benzyloxy)-5-fluoronicotinonitrile (C-1). MS-ESI (m/z): 229 [M+1]$^+$.

2-(2-Amino-2-(2-(benzyloxy)-5-fluoropyridin-3-yl)cyclopropyl)ethan-1-ol (C-2)

To a solution of Ti(O-i-Pr)$_4$ (2.56 g, 9.00 mmol) in Et$_2$O (25 mL) was added cyclohexylmagnesium chloride (11.3 mL, 22.5 mmol) dropwise at −78° C. and the resulting mixture was stirred at −78° C. for 20 min. Then a solution of but-3-en-1-ol (325 mg, 4.50 mmol) and 2-(benzyloxy)-5-fluoronicotinonitrile (C-1) (2.05 g, 9.00 mmol) in Et$_2$O (25 mL) was added to the mixture. The reaction mixture was warmed to RT, and stirred at RT for overnight. The mixture was cooled to 0° C., quenched with 1 N NaOH aqueous solution and extracted with EtOAc (2×60 mL). The organic phase was washed sequentially with water (20 mL) and brine (20 mL), dried over Na$_2$SO$_4$ and concentrated. The residue was purified by column chromatography on silica gel, eluting with PE/EtOAc (2:1~1:1) to give the title compound 2-(2-amino-2-(2-(benzyloxy)-5-fluoropyridin-3-yl)cyclopropyl)ethan-1-ol (C-2). MS-ESI (m/z): 303 [M+1]⁺.

Tert-butyl (1-(2-(benzyloxy)-5-fluoropyridin-3-yl)-2-(2-hydroxyethyl)cyclopropyl) carbamate (C-3)

To a solution of 2-(2-amino-2-(2-(benzyloxy)-5-fluoropyridin-3-yl)cyclopropyl)-ethan-1-ol (C-2) (130 mg, 0.430 mmol) in DCM (5 mL) was added (Boc)₂O (113 mg, 0.520 mmol) and Et₃N (65 mg, 0.65 mmol) at 0° C. After addition, the mixture was warmed to RT and stirred at RT for overnight. The reaction was quenched with water, and the mixture was extracted with DCM. The extracts were washed with brine, dried over Na₂SO₄, and concentrated. The residue was purified by column chromatography on silica gel, eluting with PE/EtOAc (3:1) to give the title compound tert-butyl (1-(2-(benzyloxy)-5-fluoropyridin-3-yl)-2-(2-hydroxyethyl)-cyclopropyl)carbamate (C-3). MS-ESI (m/z): 403 [M+1]⁺.

2-(2-(2-(Benzyloxy)-5-fluoropyridin-3-yl)-2-((tert-butoxycarbonyl)amino)-cyclopropyl)ethyl methanesulfonate (C-4)

To a solution of tert-butyl (1-(2-(benzyloxy)-5-fluoropyridin-3-yl)-2-(2-hydroxyethyl)cyclopropyl)carbamate (C-3) (239 mg, 0.590 mmol) in DCM (10 mL) was added MsCl (82 mg, 0.71 mmol) and Et₃N (90 mg, 0.89 mmol) at 0° C. The mixture was stirred at 0° C. for 1 h. The reaction was quenched with water and extracted with DCM. The extracts were washed sequentially with water, sat. NaHCO₃ and brine, dried over Na₂SO₄, and concentrated to give the title compound 2-(2-(2-(benzyloxy)-5-fluoropyridin-3-yl)-2-((tert-butoxycarbonyl)amino)-cyclopropyl)ethyl methanesulfonate (C-4). MS-ESI (m/z): 481 [M+1]⁺.

tert-Butyl 1-(2-(benzyloxy)-5-fluoropyridin-3-yl)-2-azabicyclo[3.1.0]hexane-2-carb oxylate (C-5)

To a solution of 2-(2-(2-(benzyloxy)-5-fluoropyridin-3-yl)-2-((tert-butoxycarbonyl)amino)cyclopropyl)ethyl methanesulfonate (C-4) (341 mg, 0.590 mmol) in DMF (5 mL) was added NaH (48.0 mg, 1.19 mmol) at 0° C. After addition, the mixture was warmed to RT and stirred at RT for overnight. The reaction was cooled to 0° C., quenched with water and extracted with EtOAc. The extracts were washed with water and brine, dried over Na₂SO₄, and concentrated. The residue was purified by column chromatography on silica gel, eluting with PE/EtOAc (10:1) to give the title compound tert-butyl 1-(2-(benzyloxy)-5-fluoropyridin-3-yl)-2-azabicyclo[3.1.0]hexane-2-carboxylate (C-5). MS-ESI (m/z): 385 [M+1]⁺.

1-(2-(Benzyloxy)-5-fluoropyridin-3-yl)-2-azabicyclo[3.1.0]hexane trifluoroacetate (C)

To a solution of tert-butyl 1-(2-(benzyloxy)-5-fluoropyridin-3-yl)-2-azabicyclo[3.1.0]hexane-2-carboxylate (C-5) (50 mg, 0.13 mmol) in DCM (5 mL) was added TFA (1.8 mL) at 0° C. After that, the mixture was stirred at RT for 1 h, and concentrated to give 1-(2-(benzyloxy)-5-fluoropyridin-3-yl)-2-azabicyclo[3.1.0]hexane trifluoroacetate (C) as crude, which was used in next step without further purification. MS-ESI (m/z): 285 [M+1]⁺.

Intermediate D

Ethyl 5-((1-(5-fluoro-2-hydroxypyridin-3-yl)cyclopropyl)amino)pyrazolo-[1,5-a]-pyrimidine-3-carboxylate (D)

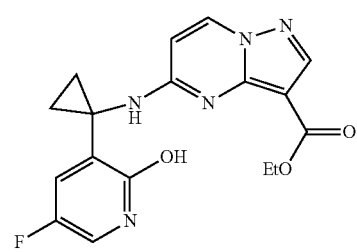

5-Fluoro-2-methoxynicotinonitrile (D-1)

To a solution of 3-bromo-5-fluoro-2-methoxypyridine (7.085 g, 34.39 mmol) in DMF (60 mL) was added Zn(CN)₂ (8.076 g, 68.79 mmol), zinc powder (67.0 mg, 1.03 mmol), 1,1'-bis(diphenyphosphino)ferrocene (DPPF) (825 mg, 1.49 mmol) and Pd₂(dba)₃ (945 mg, 1.03 mmol). The mixture was heated at 100° C. under N₂ for 7 h. The mixture was cooled to RT, diluted with water (350 mL) and extracted with EtOAc (2×100 mL). The extracts were washed with water and brine, dried over Na₂SO₄, and the solvents were evaporated to give yellow solid. This was purified by column chromatography on silica gel to give 5-fluoro-2-methoxynicotinonitrile (D-1). MS-ESI (m/z): 153 [M+1]⁺.

5-Fluoro-2-methoxy nicotinic Acid (D-2)

To a solution of 5-fluoro-2-methoxynicotinonitrile (D-1) (2.95 g, 19.4 mmol) in MeOH (35 mL) was added 5 N NaOH (17 mL). The mixture was heated at reflux for 5 h. The mixture was cooled to RT, diluted with water (50 mL), and acidified with cone. HCl to pH=2~3. The mixture was extracted with EtOAc. The extracts were washed with brine, dried over Na₂SO₄ and concentrated to give 5-fluoro-2-methoxynicotinic acid (D-2). MS-ESI (m/z): 172 [M+1]⁺.

(5-Fluoro-2-methoxypyridin-3-yl)methanol (D-3)

To a suspension of 5-fluoro-2-methoxynicotinic acid (D-2) (2.95 g, 17.0 mmol) in THF (35 mL) was added BH₃-SMe₂ (2.0 M in THF, 17 mL, 34 mmol). The mixture was stirred at RT for 1 h. The mixture was slowly quenched with water (100 mL) and extracted with EtOAc. The extracts were washed with brine, dried over Na₂SO₄, and concentrated to give (5-fluoro-2-methoxypyridin-3-yl)methanol (D-3). MS-ESI (m/z): 158 [M+1]⁺.

(5-Fluoro-2-methoxypyridin-3-yl)methyl methanesulfonate (D-4)

To a solution of (5-fluoro-2-methoxypyridin-3-yl)methanol (D-3) (2.44 g, 15.5 mmol) in DCM (35 mL) at RT was added TEA (2.79 mL) followed by MsCl (1.87 g, 16.3 mmol). The mixture was stirred at RT for 1 h. The mixture was diluted with water (100 mL) and extracted with EtOAc. The extracts were washed with brine, dried over Na₂SO₄, and concentrated to give (5-fluoro-2-methoxypyridin-3-yl) methyl methanesulfonate (D-4). MS-ESI (m/z): 236 [M+1]$^+$.

2-(5-Fluoro-2-methoxypyridin-3-yl)acetonitrile (D-5)

To a solution of (5-fluoro-2-methoxypyridin-3-yl)methyl methanesulfonate (D-4) (3.00 g, 12.8 mmol) in DMSO (30 mL) at RT was added NaCN (1.88 g, 38.3 mmol). The mixture was stirred at RT for 2 h. The mixture was diluted with water (100 mL) and extracted with EtOAc. The extracts were washed with brine, dried over Na$_2$SO$_4$, and concentrated. The residue was purified by column chromatography on silica gel and eluted with 5% 15% ethyl acetate in hexanes to give 2-(5-fluoro-2-methoxypyridin-3-yl)acetonitrile (D-5). MS-ESI (m/z): 167 [M+1]$^+$.

1-(5-Fluoro-2-methoxypyridin-3-yl)cyclopropane-1-carbonitrile (D-6)

To a solution of 2-(5-fluoro-2-methoxypyridin-3-yl)acetonitrile (D-5) (1.89 g, 11.4 mmol) in DMF (15 mL) at 0° C. was added NaH (60%, 1.37 g, 34.2 mmol). The mixture was stirred at 0° C. for 10 min. 1,2-Dibromoethane (4.28 g, 22.8 mmol) in DMF (5 mL) was added at 0° C. The mixture was stirred at RT for 1 h. The reaction was diluted with water (100 mL) and extracted with EtOAc. The extracts were washed with brine, dried over Na$_2$SO$_4$, and concentrated. The residue was purified by column chromatography on silica gel and eluted with 10% ethyl acetate in hexane to give 1-(5-fluoro-2-methoxypyridin-3-yl)cyclopropane-1-carbonitrile (D-6). MS-ESI (m/z): 193 [M+1]$^+$.

1-(5-Fluoro-2-methoxypyridin-3-yl)cyclopropane-1-carboxylic Acid (D-7)

To a solution of 1-(5-fluoro-2-methoxypyridin-3-yl)cyclopropane-1-carbonitrile (D-6) (1.96 g, 10.2 mmol) in EtOH (45 mL) was added 5 N NaOH (22 mL). The mixture was heated at reflux for 8 h. The mixture was cooled to RT, diluted with water (50 mL), and acidified with conc. HCl to pH=2~3. The mixture was extracted with EtOAc, washed with brine, dried over Na$_2$SO$_4$, and concentrated to give 1-(5-fluoro-2-methoxypyridin-3-yl)cyclopropane-1-carboxylic acid (D-7). MS-ESI (m/z): 212 [M+1]$^+$.

Methyl (1-(5-fluoro-2-methoxypyridin-3-yl)cyclopropyl)carbamate (D-8)

To a solution of 1-(5-fluoro-2-methoxypyridin-3-yl)cyclopropane-1-carboxylic acid (D-7) (2.12 g, 10.1 mmol) in toluene (10 mL) was added Et$_3$N (1.12 g, 11.1 mmol) followed by DPPA (3.04 g, 11.1 mmol). The mixture was heated at 100° C. for 2 h. Then MeOH (10 mL) was added. The mixture was heated at 80° C. for additional 2 h. The mixture was cooled to RT, diluted with water (100 mL) and extracted with EtOAc. The extracts were washed with brine, dried (Na$_2$SO$_4$), and concentrated. The residue was purified by column chromatography on silica gel and eluted with 20% ethyl acetate in hexanes to give methyl (1-(5-fluoro-2-methoxypyridin-3-yl)cyclopropyl) carbamate (D-8). MS-ESI (m/z): 241 [M+1]$^+$.

1-(5-Fluoro-2-methoxypyridin-3-yl)cyclopropan-1-amine (D-9)

A solution of (1-(5-fluoro-2-methoxypyridin-3-yl)cyclopropyl)carbamate (D-8) (640 mg, 2.67 mmol) in 32% HBr—HOAc (3 mL) was stirred at RT for 8 h. The mixture was diluted with saturated aqueous NaHCO$_3$ (50 mL) and extracted with EtOAc. The extracts were washed with brine, dried over Na$_2$SO$_4$, and concentrated. The residue was purified by column chromatography on silica gel, eluted with 30-50% EtOAc in hexanes to give 1-(5-fluoro-2-methoxypyridin-3-yl)cyclopropan-1-amine (D-9). MS-ESI (m/z): 183 [M+1]$^+$.

Ethyl 5-((1-(5-fluoro-2-methoxypyridin-3-yl)cyclopropyl)amino)pyrazolo[1,5-a]pyrimidine-3-carboxylate (D-10)

To a solution of 1-(5-fluoro-2-methoxypyridin-3-yl)cyclopropan-1-amine (D-9) (197 mg, 1.03 mmol) and ethyl 5-chloropyrazolo[1,5-a]pyrimidine-3-carboxylate (1a) (WO 2017/007759) (232 mg, 1.03 mmol) in n-butanol (3.5 mL) was added DIPEA (529 mg, 4.10 mmol). The mixture was heated at 110° C. for 8 h. The mixture was cooled to RT, diluted with water (30 mL) and extracted with EtOAc. The extracts were washed with brine, dried over Na$_2$SO$_4$, and concentrated. The residue was purified by column chromatography on silica gel and eluted with 40% ethyl acetate in hexane to give ethyl 5-((1-(5-fluoro-2-methoxypyridin-3-yl) cyclopropyl) amino)pyrazolo-[1,5-a]pyrimidine-3-carboxylate (D-10). MS-ESI (m/z): 372 [M+1]$^+$.

Ethyl 5-((1-(5-fluoro-2-hydroxypyridin-3-yl)cyclopropyl)amino)pyrazolo[1,5-a]pyrimidine-3-carboxylate (D)

To a solution of ethyl 5-((1-(5-fluoro-2-methoxypyridin-3-yl)cyclopropyl)-amino)pyrazolo[1,5-a]pyrimidine-3-carboxylate (D-10) (294 mg, 0.792 mmol) in HOAc (1.5 mL) was added 32% HBr—HOAc (1.5 mL). The mixture was heated at 90° C. for 2 h. The mixture was cooled to RT, diluted with saturated aqueous NaHCO$_3$ (50 mL) and extracted with EtOAc. The extracts were washed with brine, dried over Na$_2$SO$_4$, and concentrated. The residue was purified by column chromatography on silica gel and eluted with 4% MeOH in DCM to give ethyl 5-((1-(5-fluoro-2-hydroxypyridin-3-yl)cyclopropyl)amino)pyrazolo[1,5-a]pyrimidine-3-carboxylate (D). MS-ESI (m/z): 358 [M+1]$^+$.

Intermediate E 1-(2-(Benzyloxy)-5-fluorophenyl)-N-methylcyclopropan-1-amine 2,2,2-trifluoroacetate (E)

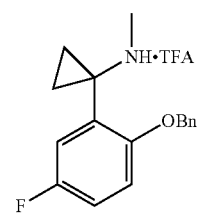

E tert-Butyl (1-(2-(benzyloxy)-5-fluorophenyl)cyclopropyl)carbamate (E-1)

To a solution of 1-(2-(benzyloxy)-5-fluorophenyl)cyclopropan-1-amine (B) (0.24 g, 0.93 mmol) in DCM (15 mL)

was added (Boc)$_2$O (0.304 g, 1.39 mmol) and Et$_3$N (0.39 mL, 2.78 mmol) at RT and stirred for overnight. The reaction was quenched with water, and the mixture was extracted with DCM. The extracts were washed with brine, dried over Na$_2$SO$_4$, and concentrated. The residue was purified by column chromatography on silica gel, eluting with PE/EtOAc (20:1~5:1) to give the title compound tert-butyl (1-(2-(benzyloxy)-5-fluorophenyl)cyclopropyl)-carbamate (E-1). MS-ESI (m/z): 358 [M+1]$^+$.

tert-Butyl (1-(2-(benzyloxy)-5-fluorophenyl)cyclopropyl)(methyl)carbamate (E-2)

To a solution of tert-butyl (1-(2-(benzyloxy)-5-fluorophenyl)cyclopropyl) carbamate (E-1) (0.27 g, 0.91 mmol) in DMF (5 mL) was added NaH (54.0 mg, 1.36 mmol) at 0° C. After 15 mins, CH$_3$I (0.20 mL, 3.2 mmol) was added, the mixture was further stirred for 1 h. The reaction was quenched with water and extracted with EtOAc. The extracts were washed with water and brine, dried over Na$_2$SO$_4$, and concentrated. The residue was purified by column chromatography on silica gel, eluting with PE/EtOAc (20:1~5:1) to give the title compound tert-butyl (1-(2-(benzyloxy)-5-fluorophenyl)cyclopropyl)(methyl)carbamate (E-2). MS-ESI (m/z): 372 [M+1]$^+$.

1-(2-(Benzyloxy)-5-fluorophenyl)-N-methylcyclopropan-1-amine 2,2,2-trifluoroacetate (E)

To a solution of tert-butyl (1-(2-(benzyloxy)-5-fluorophenyl)cyclopropyl) (methyl)carbamate (E-2) (137 mg, 0.370 mmol) in DCM (2.5 mL) was added TFA (0.6 mL) at 0° C. The mixture was stirred at RT for 1 h, and concentrated to give 1-(2-(benzyloxy)-5-fluorophenyl)-N-methylcyclopropan-1-amine 2,2,2-trifluoroacetate (E) as crude, which was used in next step without further purification. MS-ESI (m/z): 272 [M+1]$^+$.

Intermediate F

Ethyl 6-(1-(5-fluoro-2-hydroxyphenyl)-2-azabicyclo[3.1.0]hexan-2-yl)imidazo-[1,2-b]pyridazine-3-carboxylate (F)

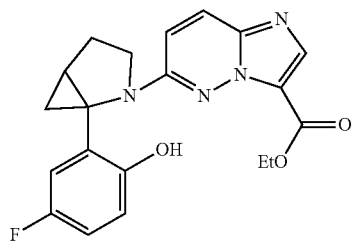

Ethyl 6-chloroimidazo[1,2-b]pyridazine-3-carboxylate (F-1)

The title compound ethyl 6-chloroimidazo[1,2-b]pyridazine-3-carboxylate (F-1) was prepared according to the method described in US 2012/0065184.

Ethyl 6-(1-(2-(benzyloxy)-5-fluorophenyl)-2-azabicyclo[3.1.0]hexan-2-yl)imidazo[1,2-b]pyridazine-3-carboxylate (F-2)

The mixture of 1-(2-(benzyloxy)-5-fluorophenyl)-2-azabicyclo[3.1.0]hexane (170 mg, 0.600 mmol), ethyl 6-chloroimidazo[1,2-b]pyridazine-3-carboxylate (F-1) (220 mg, 1.20 mmol) and KF (348 mg, 6.00 mmol) in DMSO (5 mL) was stirred at 120° C. for 24 h. The reaction was cooled to RT, quenched with water and extracted with EtOAc. The extracts were washed with water and brine, dried over Na$_2$SO$_4$, and concentrated. The residue was purified by column chromatography on silica gel, eluting with PE/EtOAc (5:1~1:1) to give the title compound ethyl 6-(1-(2-(benzyloxy)-5-fluorophenyl)-2-azabicyclo[3.1.0]hexan-2-yl)imidazo[1,2-b]pyridazine-3-carboxylate (F-2). MS-ESI (m/z): 473 [M+1]$^+$.

Ethyl 6-(1-(5-fluoro-2-hydroxyphenyl)-2-azabicyclo[3.1.0]hexan-2-yl)imidazo-[1,2-b]pyridazine-3-carboxylate (F)

The mixture of ethyl 6-(1-(2-(benzyloxy)-5-fluorophenyl)-2-azabicyclo[3.1.0]hexan-2-yl)imidazo[1,2-b]pyridazine-3-carboxylate (F-2) (75 mg, 0.16 mmol) and Pd/C (10%, 25 mg) in MeOH (2 mL) was stirred at RT for 3 h at the atmosphere of H$_2$ (1 atm). Then the mixture was filtered, and the filtrate was concentrated to give the title compound ethyl 6-(1-(5-fluoro-2-hydroxyphenyl)-2-azabicyclo[3.1.0]hexan-2-yl)imidazo[1,2-b]pyridazine-3-carboxylate (F). MS-ESI (m/z): 383 [M+1]$^+$.

Intermediate G

Ethyl 6-(1-(5-fluoro-2-hydroxypyridin-3-yl)-2-azabicyclo[3.1.0]hexan-2-yl)imidazo-f[2-b]pyridazine-S-carboxylate (G)

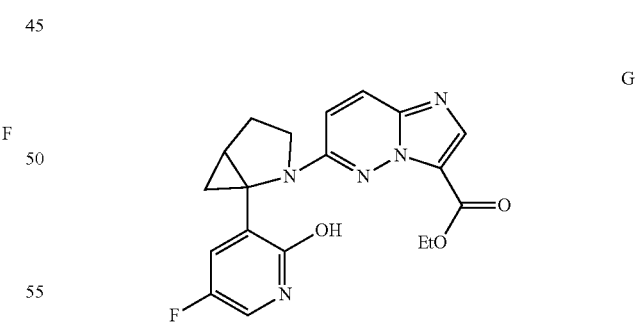

The title compound ethyl 6-(1-(5-fluoro-2-hydroxypyridin-3-yl)-2-azabicyclo-[3.1.0]hexan-2-yl)imidazo[1,2-b]pyridazine-3-carboxylate (G) was prepared according to the synthetic method of Intermediate F by replacing 1-(2-(benzyloxy)-5-fluorophenyl)-2-azabicyclo[3.1.0]hexane with 1-(2-(benzyloxy)-5-fluoropyridin-3-yl)-2-azabicyclo[3.1.0] hexane. MS-ESI (m/z): 384 [M+1]$^+$.

Intermediate H

Ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H)

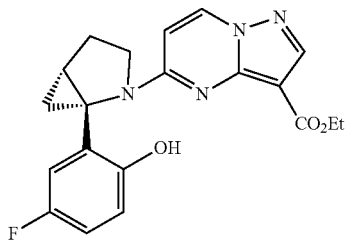

2-(5-Fluoro-2-methoxyphenyl)acetonitrile (H-1)

A mixture of 2-(bromomethyl)-4-fluoro-1-methoxybenzene (6.00 g, 27.4 mmol), NaCN (4.00 g, 81.6 mmol) and n-Bu$_4$NI (1.01 g, 2.74 mmol) in DCM/H$_2$O (60 mL/60 mL) was stirred at RT for 6 hours. The reaction was quenched with saturated NaHCO$_3$ aqueous solution and extracted with DCM. The extracts were washed with brine, dried over Na$_2$SO$_4$, and evaporated to give the crude product. This was purified by column chromatography on silica gel, eluting with PE/EtOAc (10:1~6:1) to give the product of 2-(5-fluoro-2-methoxyphenyl)acetonitrile (H-1).

(1R,5S) 1-(5-fluoro-2-methoxyphenyl)-3-oxabicyclo[3.1.0]hexan-2-one (H-2)

To a mixture of (S)-2-(chloromethyl)oxirane (3.38 mL, 39.1 mmol) and 2-(5-fluoro-2-methoxyphenyl)acetonitrile (H-1) (4.300 g, 26.06 mmol) in THF (36 mL) was added NaHMDS (32.5 mL, 65.2 mmol) dropwise at −15° C. The mixture was stirred at −15° C. for 3 h. The reaction was quenched with water (40 mL) and stirred for 5 min. The mixture was concentrated. The residue was diluted with EtOH (35 mL), and KOH (5.4 g) were added. Then the mixture was stirred at 80° C. for overnight. The reaction mixture was cooled to r.t. and conc. HCl (25 mL) were added. The mixture was stirred at 60° C. for 3 h. The mixture was extracted with EtOAc. The extracts were washed sequentially with water and brine, dried over Na$_2$SO$_4$, and concentrated. The residue was purified by column chromatography on silica gel to give the title compound (1R,5S)-1-(5-fluoro-2-methoxyphenyl)-3-oxabicyclo[3.1.0]hexan-2-one (H-2). MS-ESI (m/z): 223 [M+1]$^+$.

(1R,2S)-1-(5-fluoro-2-methoxyphenyl)-2-(hydroxymethyl)cyclopropane-1-carboxamide (H-3)

A mixture of (1R,5S)-1-(5-fluoro-2-methoxyphenyl)-3-oxabicyclo[3.1.0]hexan-2-one (H-2) (2.09 g, 9.41 mmol) in NH$_3$/MeOH (7 N/20 mL) was stirred at r.t. for 3 h. The mixture was concentrated. The residue was purified by column chromatography on silica gel, eluting with PE/EtOAc (3:1~1:1) to give the title compound (1R,2S)-1-(5-fluoro-2-methoxyphenyl)-2-(hydroxymethyl)cyclopropane-1-carboxamide (H-3). MS-ESI (m/z): 240 [M+1]$^+$.

(1R,6S)-1-(5-fluoro-2-methoxyphenyl)-4-oxa-2-azabicyclo[4.1.0]heptan-3-one (H-4)

To a solution of (1R,2S)-1-(5-fluoro-2-methoxyphenyl)-2-(hydroxymethyl)-cyclopropane-1-carboxamide (H-3) (675 mg, 2.82 mmol) in CH$_3$CN (30 mL) was added phenyl-λ$^3$-iodanediyl diacetate (1.36 g, 4.23 mmol) at 0° C. The mixture was warmed to r.t. and stirred at RT for 13 h. The reaction was quenched with water and extracted with EtOAc. The extracts were washed sequentially with water and brine, dried over Na$_2$SO$_4$, and concentrated to give the title compound (1R,6S)-1-(5-fluoro-2-methoxyphenyl)-4-oxa-2-azabicyclo[4.1.0]heptan-3-one (H-4). MS-ESI (m/z): 238 [M+1]$^+$.

((1S,2R)-2-amino-2-(5-fluoro-2-methoxyphenyl)cyclopropyl)methanol (H-5)

A mixture of (1R,6S)-1-(5-fluoro-2-methoxyphenyl)-4-oxa-2-azabicyclo[4.1.0]heptan-3-one (H-4) (480 mg, 2.02 mmol) and NaOH (400 mg, 10.0 mmol) in EtOH/H$_2$O (3 mL/3 mL) was stirred at 70° C. for overnight. The reaction mixture was cooled to r.t. and concentrated. The residue was washed with PE and extracted with EtOAc. The extracts were washed sequentially with water and brine, dried and concentrated to give the title compound ((1S,2R)-2-amino-2-(5-fluoro-2-methoxyphenyl)cyclopropyl)methanol (H-5). MS-ESI (m/z): 212 [M+1]$^+$.

((1S,2R)-2-(benzylideneamino)-2-(5-fluoro-2-methoxyphenyl)cyclopropyl)methanol (H-6)

The mixture of ((1S,2R)-2-amino-2-(5-fluoro-2-methoxyphenyl)cyclopropyl) methanol (H-5) (250 mg, 1.18 mmol) and benzaldehyde (152 mg, 1.42 mmol) in DCM was stirred at RT for overnight. The mixture was extracted with DCM. The extracts were washed with brine, dried over Na$_2$SO$_4$, and concentrated to give the crude product of the title compound ((1S,2R)-2-(((E)-benzylidene)amino)-2-(5-fluoro-2-methoxyphenyl)cyclopropyl)-methanol (H-6). MS-ESI (m/z): 300 [M+1]$^+$.

((1S,2R)-2-(benzylideneamino)-2-(5-fluoro-2-methoxyphenyl)cyclopropyl) methyl methanesulfonate (H-7)

The mixture of ((1S,2R)-2-(benzylideneamino)-2-(5-fluoro-2-methoxyphenyl) cyclopropyl)methanol (H-6) (352 mg, 1.17 mmol), MsCl (137 µL, 1.75 mmol) and Et$_3$N (326 µL, 2.34 mmol) in DCM (15 mL) was stirred at 0° C. for 1.5 hours. The mixture was extracted with DCM. The extracts were washed with brine, dried over Na$_2$SO$_4$, and concentrated to give the crude product of the title compound ((1S,2R)-2-(((E)-benzylidene)amino)-2-(5-fluoro-2-methoxyphenyl)-methyl methanesulfonate (H-7). MS-ESI (m/z): 378 [M+1]$^+$.

2-((1R,2R)-2-(benzylideneamino)-2-(5-fluoro-2-methoxyphenyl)cyclopropyl) acetonitrile (H-8)

The mixture of ((1S,2R)-2-(benzylideneamino)-2-(5-fluoro-2-methoxyphenyl) cyclopropyl)methyl methanesulfonate (H-7) (200 mg, 0.530 mmol) and NaCN (116 mg, 2.42 mmol) in DMF (6 mL) was stirred at 45° C. for 4 hours. The reaction mixture was cooled to r.t. and extracted with EtOAc. The extracts were washed sequentially with water and brine, dried over Na$_2$SO$_4$, and concentrated to give the crude product of the title compound 2-((1R,2R)-2-(((E)-benzylidene)amino)-2-(5-fluoro-2-methoxyphenyl)cyclopropyl)acetonitrile (H-8). MS-ESI (m/z): 309 [M+1]⁺.

2-((1R,2R)-2-(benzylideneamino)-2-(5-fluoro-2-methoxyphenyl)cyclopropyl) acetamide (H-9)

A mixture of 2-((1R,2R)-2-(benzylideneamino)-2-(5-fluoro-2-methoxyphenyl) cyclopropyl)acetonitrile (H-8) (2.67 g, 8.66 mmol) and $K_2CO_3$ (3.00 g, 21.0 mmol) in DMSO (80 mL) was added dropwise $H_2O_2$ (30%, 20 mL, 172 mmol) under ice water bath in portions for 4 times and stirred at RT for overnight. The reaction mixture was diluted with water (200 mL) and extracted with EtOAc (3×100 mL). The extracts were washed sequentially with water and brine, dried over $Na_2SO_4$, and concentrated to give the crude product of the title compound 2-((1R,2R)-2-(((E)-benzylidene)amino)-2-(5-fluoro-2-methoxyphenyl)cyclopropyl)acetamide (H-9). MS-ESI (m/z): 327 [M+1]⁺.

2-((1R,2R)-2-amino-2-(5-fluoro-2-methoxyphenyl)cyclopropyl)acetamide (H-10)

To a mixture of 2-((1R,2R)-2-(((E)-benzylidene)amino)-2-(5-fluoro-2-methoxyphenyl)cyclopropyl)acetamide (H-9) (616 mg, 1.89 mmol) in $CH_3CN$ (6 mL) was added HCl (1 N, 10 mL) at 0° C. The mixture was warmed to room temperature and stirred for 2 hours. The mixture was extracted with PE/EtOAc (1:1) and washed with HCl (1 N, 10 mL). The combined aqueous layers were washed with PE/EtOAc (1:1). The aqueous layer were adjusted to pH=8~9 using saturated aqueous $Na_2CO_3$ and extracted with EtOAc (4×80 mL), dried over $Na_2SO_4$, and concentrated to give the crude product of the title compound 2-((1R,2R)-2-amino-2-(5-fluoro-2-methoxyphenyl)cyclopropyl)acetamide (H-10). MS-ESI (m/z): 239 [M+1]⁺.

(1R,5R)-1-(5-fluoro-2-methoxyphenyl)-2-azabicyclo[3.1.0]hexan-3-one (H-11)

A mixture of 2-((1R,2R)-2-amino-2-(5-fluoro-2-methoxyphenyl)cyclopropyl)-acetamide (H-10) (327 mg, 1.37 mmol) and conc. HCl (1 mL, 12 mmol) in MeOH (6.5 mL) was stirred at 60° C. for 5 h. The reaction mixture was cooled to 0° C., $Na_2CO_3$ (1.100 g, 10.38 mmol) and water (13 mL) were added. The mixture was stirred at 60° C. for 3 h. The reaction mixture was cooled to r.t. and extracted with DCM, the extracts were washed sequentially with HCl (1 N), water and brine, dried over $Na_2SO_4$, and concentrated to give the crude product of the title compound (1R,5R)-1-(5-fluoro-2-methoxyphenyl)-2-azabicyclo[3.1.0]hexan-3-one (H-11). MS-ESI (m/z): 222 [M+1]⁺.

(1R,5S)-1-(5-fluoro-2-methoxyphenyl)-2-azabicyclo[3.1.0]hexane (H-12)

To a mixture of (1R,5R)-1-(5-fluoro-2-methoxyphenyl)-2-azabicyclo[3.1.0]hexan-3-one (H-11) (247 mg, 1.12 mmol) in dry THF (10 mL) was added borane dimethyl sulfide complex solution (10 M, 0.67 mL) dropwise at 0° C. Then the mixture was warmed to 60° C. and stirred for 12 h. The reaction mixture was cooled to r.t., quenched with MeOH (7 mL) and HCl aqueous (6 N, 6 mL). The mixture was stirred at RT for 1 h. The mixture was extracted with EtOAc (2×15 mL), the aqueous layer were adjusted to pH=10 using NaOH (1.08 g) and extracted with EtOAc. The extracts were washed sequentially with water and brine, dried over $Na_2SO_4$, and concentrated to give the crude product of the title compound (1R,5S)-1-(5-fluoro-2-methoxyphenyl)-2-azabicyclo[3.1.0]hexane (H-12). MS-ESI (m/z): 208 [M+1]⁺.

Ethyl 5-((1R,5S)-1-(5-fluoro-2-methoxyphenyl)-2-azabicyclo[3.1.0]hexan-2-yl)pyrazolo[1,5-a]pyrimidine-3-carboxylate (H-13)

A mixture of (1R,5S)-1-(5-fluoro-2-methoxyphenyl)-2-azabicyclo-[3.1.0]hexane (H-12) (120 mg, 0.580 mmol), ethyl 5-chloropyrazolo[1,5-a]pyrimidine-3-carboxylate (1a) (WO 2017/007759) (177 mg, 0.700 mmol) and DIPEA (0.50 mL, 2.9 mmol) in n-BuOH (4 mL) was stirred at 125° C. for 19 h. The reaction mixture was cooled to RT and extracted with EtOAc. The extracts were washed sequentially with water and brine, dried over $Na_2SO_4$, concentrated. The residue was purified by column chromatography on silica gel, eluting with PE/EtOAc (5:1~3:1) to give the product of ethyl 5-((1R,5S)-1-(5-fluoro-2-methoxyphenyl)-2-azabicyclo[3.1.0]hexan-2-yl)pyrazolo[1,5-a]pyrimidine-3-carboxylate (H-13). MS-ESI (m/z): 397 [M+1]⁺.

Ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H)

To a solution of ethyl 5-((1R,5S)-1-(5-fluoro-2-methoxyphenyl)-2-azabicyclo[3.1.0]hexan-2-yl)pyrazolo[1,5-a]pyrimidine-3-carboxylate (H-13) (0.15 g, 0.38 mmol) in DCM (15 mL) was added $BBr_3$ (0.64 mL, 0.65 mmol) at 0° C. and stirred at the same temperature for 1.5 h. Then additional $BBr_3$ (0.64 mL, 0.65 mmol) was added and stirred at 0° C. for 2 h. The reaction was quenched with water. The mixture was extracted with DCM. The extracts were sequentially with saturated $NaHCO_3$, water and brine, dried over $Na_2SO_4$, and concentrated to give the crude product of the title compound ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H). MS-ESI (m/z): 383 [M+1]⁺.

Intermediate I

Ethyl 5-((1R,5S)-1-(5-fluoro-2-hydroxypyridin-3-yl)-2-azabicyclo[3.1.0]hexan-2-yl)pyrazolo[1,5-a]pyrimidine-3-carboxylate (I)

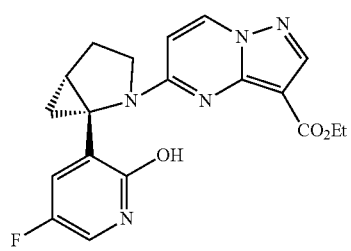

The title compound I was prepared according to the synthetic method of H by replacing 2-(5-fluoro-2-methoxyphenyl)acetonitrile (H-1) with 2-(5-fluoro-2-methoxypyridin-3-yl)acetonitrile (D-5). MS-ESI (m/z): 384 [M+1]⁺.

Intermediate J

Ethyl 5-((1-(5-fluoro-2-hydroxypyridin-3-yl)cyclopropyl)(methyl)amino)pyrazolo[1,5-a]pyrimidine-3-carboxylate (J)

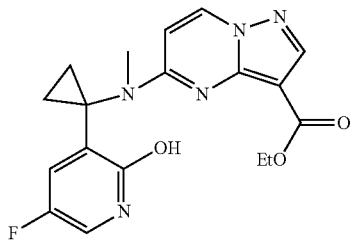

Ethyl 5-((1-(5-fluoro-2-methoxypyridin-3-yl)cyclopropyl)(methyl)amino)pyrazolo[1,5-a]pyrimidine-3-carboxylate (J-1)

To a solution of ethyl 5-((1-(5-fluoro-2-methoxypyridin-3-yl)cyclopropyl)amino)-pyrazolo[1,5-a]pyrimidine-3-carboxylate (D-10) (331 mg, 0.892 mmol) in DMF (5 mL) was added NaH (60%, 71.4 mg, 1.78 mmol) at RT and stirred for 10 min. Then MeI (253 mg, 1.75 mmol) was added dropwise and stirred for 50 min. The mixture was diluted with water (30 mL) and extracted with EtOAc (2×). The extracts were washed with brine, dried over $Na_2SO_4$, and concentrated to give ethyl 5-((1-(5-fluoro-2-methoxypyridin-3-yl) cyclopropyl)(methyl)amino)pyrazolo[1,5-a]pyrimidine-3-carboxylate (J-1) as crude, which was used in next step without further purification. MS-ESI (m/z): 386 $[M+1]^+$.

Ethyl 5-((1-(5-fluoro-2-hydroxypyridin-3-yl)cyclopropyl)(methyl)amino)pyrazolo[1,5-a]pyrimidine-3-carboxylate (J)

The title compound J was prepared according to the synthetic method of D by replacing ethyl 5-((1-(5-fluoro-2-methoxypyridin-3-yl)cyclopropyl)amino)pyrazolo[1,5-a]pyrimidine-3-carboxylate (D-10) with ethyl 5-((1-(5-fluoro-2-methoxypyridin-3-yl) cyclopropyl)(methyl)amino) pyrazolo[1,5-a]pyrimidine-3-carboxylate (J-1). MS-ESI (m/z): 372 $[M+1]^+$.

Example 1

($1^3$E,$1^4$E,6R)-$3^5$-fluoro-6-methyl-4-oxa-$2^2$,7-diaza-1(5,3)-pyrazolo[1,5-a]pyrimidina-2(2,1)-azabicyclo[3.1.0]hexana-3(1,2)-benzenacyclooctaphan-8-one (1)

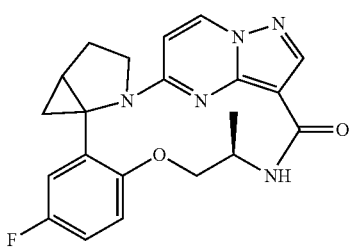

Ethyl 5-chloropyrazolo[1,5-a]pyrimidine-3-carboxylate (1a)

The title compound ethyl 5-chloropyrazolo[1,5-a]pyrimidine-3-carboxylate (1a) was prepared according to the method described in WO 2017/007759.

Ethyl 5-(1-(5-fluoro-2-hydroxyphenyl)-2-azabicyclo[3.1.0]hexan-2-yl)pyrazolo-[1,5-a]pyrimidine-3-carboxylate (1b)

The mixture of ethyl 5-chloropyrazolo[1,5-a]pyrimidine-3-carboxylate (1a) (82.0 mg, 0.360 mmol), 1-(5-fluoro-2-hydroxyphenyl)-2-azabicyclo[3.1.0]hexan-2-ium trifluoroacetate (A) (96.0 mg, 0.330 mmol) and DIPEA (0.40 mL, 2.4 mmol) in n-BuOH (3 mL) was stirred at 120° C. for 6 h. The reaction was cooled to RT, quenched with water and extracted with EtOAc. The extracts were washed with water and brine, dried over $Na_2SO_4$, and concentrated. The residue was purified by column chromatography on silica gel, eluting with PE/EtOAc (3:1~1:1) to give the title compound ethyl 5-(1-(5-fluoro-2-hydroxyphenyl)-2-azabicyclo[3.1.0]hexan-2-yl)pyrazolo[1,5-a]pyrimidine-3-carboxylate (1b). MS-ESI (m/z): 383 $[M+1]^+$.

(R)-2-((tert-butoxycarbonyl)amino)propyl methanesulfonate (1c)

The title compound (R)-2-((tert-butoxycarbonyl)amino) propyl methanesulfonate (1c) was prepared according to the method described in J. Org. Chem. 2010, 75, 2718-2721.

Ethyl 5-(1-(2-((R)-2-((tert-butoxycarbonyl)amino)propoxy)-5-fluorophenyl)-2-azabicyclo[3.1.0]hexan-2-yl)pyrazolo[1,5-a]pyrimidine-3-carboxylate (1d)

To a solution of ethyl 5-(1-(5-fluoro-2-hydroxyphenyl)-2-azabicyclo[3.1.0]-hexan-2-yl)pyrazolo[1,5-a]pyrimidine-3-carboxylate (1b) (54.0 mg, 0.142 mmol) in DMF (3 mL) was added $Cs_2CO_3$ (278 mg, 0.852 mmol). The mixture was heated to 70° C. and stirred for 30 min. Then (ethyl (R)-2-((tert-butoxycarbonyl)amino)propyl methanesulfonate (1c) (107 mg, 0.426 mmol) was added. The mixture was stirred at 70° C. for overnight. The mixture was cooled to RT, diluted with water, and extracted with EtOAc. The extracts were washed with brine, dried over $Na_2SO_4$, and concentrated. The residue was purified by column chromatography on silica gel, eluting with PE/EtOAc (1:1) to give ethyl 5-(1-(2-((R)-2-((tert-butoxycarbonyl)amino)-propoxy)-5-fluorophenyl)-2-azabicyclo[3.1.0]hexan-2-yl) pyrazolo[1,5-a]pyrimidine-3-carboxylate (1d). MS-ESI (m/z): 540 $[M+1]^+$.

5-(1-(2-((R)-2-((tert-butoxycarbonyl)amino)propoxy)-5-fluorophenyl)-2-azabicyclo[3.1.0]hexan-2-yl)pyrazolo[1,5-a]pyrimidine-3-carboxylic acid (1e)

A mixture of ethyl 5-(1-(2-((R)-2-((tert-butoxycarbonyl) amino)propoxy)-5-fluorophenyl)-2-azabicyclo[3.1.0]hexan-2-yl)pyrazolo[1,5-a]pyrimidine-3-carboxylate (1d) (38 mg, 0.071 mmol) and $LiOH \cdot H_2O$ (40 mg, 0.95 mmol) in MeOH/ $H_2O$ (2 mL/0.2 mL) was stirred at 70° C. for 4 h. The mixture was cooled to RT and concentrated. The residue was acidified to pH=3~4 with 0.5 N HCl aqueous solution and extracted with EtOAc. The extracts were was washed with brine, dried over $Na_2SO_4$, and concentrated to give the title compound 5-(1-(2-((R)-2-((tert-butoxycarbonyl)amino)propoxy)-5-fluorophenyl)-2-azabicyclo[3.1.0]hexan-2-yl)pyrazolo[1,5-a]pyrimidine-3-carboxylic acid (1e). MS-ESI (m/z): 512 [M+1]$^+$.

(2R)-1-(2-(2-(3-carboxypyrazolo[1,5-a]pyrimidin-5-yl)-2-azabicyclo[3.1.0]Hexan-1-yl)-4-fluorophenoxy)propan-2-aminium Trifluoroacetate (1f)

To a solution of 5-(1-(2-((R)-2-((tert-butoxycarbonyl)amino)propoxy)-5-fluorophenyl)-2-azabicyclo[3.1.0]hexan-2-yl)pyrazolo[1,5-a]pyrimidine-3-carboxylic acid (1e) (35 mg, 0.069 mmol) in DCM (2 mL) at 0° C. was added TFA (2 mL). The mixture was stirred at RT for 45 min, and concentrated to give (2R)-1-(2-(2-(3-carboxypyrazolo[1,5-a]pyrimidin-5-yl)-2-azabicyclo[3.1.0]hexan-1-yl)-4-fluorophenoxy)propan-2-aminium trifluoroacetate (1f) as crude, which was used in next step without further purification. MS-ESI (m/z): 412 [M+1]$^+$.

(1$^3$E,1$^4$E,6R)-3$^5$-fluoro-6-methyl-4-oxa-2$^2$,7-diaza-1(5,3)-pyrazolo[1,5-a]pyrimidina-2(2,1)-bicyclo[3.1.0]hexana-3(1,2)-benzenacyclooctaphan-8-one (1)

To a solution of (2R)-1-(2-(2-(3-carboxypyrazolo[1,5-a]pyrimidin-5-yl)-2-azabicyclo[3.1.0]hexan-1-yl)-4-fluorophenoxy)propan-2-aminium trifluoroacetate (1f) (26.8 mg, 0.0650 mmol) in DMF (11 mL) at RT was added HATU (30 mg, 0.078 mmol). Then a solution of DIPEA (0.11 mL, 0.65 mmol) in DMF was added dropwise to the mixture at RT and the resulting mixture was stirred for overnight. The mixture was diluted with water (10 mL) and extracted with EtOAc. The extracts were washed with brine (40 mL), dried over Na$_2$SO$_4$ and concentrated. The residue was purified by preparative TLC, eluting with DCM/MeOH (20:1) to give (1$^3$E,1$^4$E,6R)-3$^5$-fluoro-6-methyl-4-oxa-2$^2$,7-diaza-1(5,3)-pyrazolo[1,5-a]pyrimidina-2(2,1)-bicyclo[3.1.0]hexana-3(1,2)-benzenacyclooctaphan-8-one (1). MS-ESI (m/z): 394 [M+1]$^+$.

Example 2

(R,3'E,4'E)-5'-fluoro-7'-methylspiro[cyclopropane-1,3'-5-oxa-2,8-diaza-1(5,3)-pyrazolo[1,5-a]pyrimidina-4(1,2)-benzenacyclononaphan]-9'-one (2)

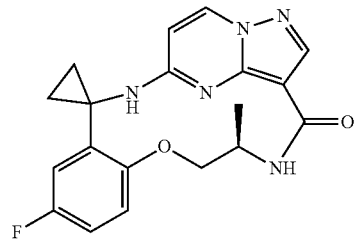

Ethyl 5-((1-(2-(benzyloxy)-5-fluorophenyl)cyclopropyl)amino)pyrazolo[1,5-a]-pyrimidine-3-carboxylate (2a)

The title compound ethyl 5-((1-(2-(benzyloxy)-5-fluorophenyl)cyclopropyl)-amino)pyrazolo[1,5-a]pyrimidine-3-carboxylate (2a) was prepared according to the synthetic method of ethyl 5-(1-(5-fluoro-2-hydroxyphenyl)-2-azabicyclo[3.1.0]hexan-2-yl)pyrazolo-[1,5-a]pyrimidine-3-carboxylate (1b) by replacing 1-(5-fluoro-2-hydroxyphenyl)-2-azabicyclo[3.1.0]hexan-2-ium trifluoroacetate (A) with 1-(2-(benzyloxy)-5-fluorophenyl)-cyclopropan-1-amine (B). MS-ESI (m/z): 447 [M+1]$^+$.

Ethyl 5-((1-(5-fluoro-2-hydroxyphenyl)cyclopropyl)amino)pyrazolo[1,5-a]pyrimidine-3-carboxylate (2b)

The title compound ethyl 5-((1-(5-fluoro-2-hydroxyphenyl)cyclopropyl)amino)-pyrazolo[1,5-a]pyrimidine-3-carboxylate (2b) was prepared according to the synthetic method of tert-butyl 1-(5-fluoro-2-hydroxyphenyl)-2-azabicyclo[3.1.0]hexane-2-carboxylate (A-6) by replacing tert-butyl 1-(2-(benzyloxy)-5-fluorophenyl)-2-azabicyclo[3.1.0]hexane-2-carboxylate (A-5) with ethyl 5-((1-(2-(benzyloxy)-5-fluorophenyl)cyclopropyl)amino)pyrazolo[1,5-a]-pyrimidine-3-carboxylate (2a). MS-ESI (m/z): 357 [M+1]$^+$.

(R,3'E,4'E)-5'-fluoro-7'-methylspiro[cyclopropane-1,3'-5-oxa-2,8-diaza-1(5,3)-pyrazolo[1,5-a]pyrimidina-4(1,2)-benzenacyclononaphan]-9'-one (2)

The title compound (R,3'E,4'E)-5'-fluoro-7'-methylspiro[cyclopropane-1,3'-5-oxa-2,8-diaza-1(5,3)-pyrazolo[1,5-a]pyrimidina-4(1,2)-benzenacyclononaphan]-9'-one (2) was prepared according to the synthetic method of 1 by replacing ethyl 5-(1-(5-fluoro-2-hydroxyphenyl)-2-azabicyclo[3.1.0]hexan-2-yl)pyrazolo[1,5-a]pyrimidine-3-carboxylate (1b) with ethyl 5-((1-(5-fluoro-2-hydroxyphenyl)cyclopropyl)amino)pyrazolo-[1,5-a]pyrimidine-3-carboxylate (2b). MS-ESI (m/z): 368 [M+1]$^+$.

Example 3

(1$^3$E,1$^4$E,5S)-3$^5$-fluoro-5-methyl-4-oxa-2$^2$,7-diaza-1(5,3)-pyrazolo[1,5-a]pyrimidina-2(2,1)-bicyclo[3.1.0]hexana-3(1,2)-benzenacyclooctaphan-8-one (3)

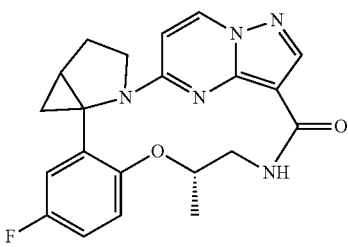

The title compound (1$^4$E,1$^4$E,5S)-3$^5$-fluoro-5-methyl-4-oxa-2$^2$,7-diaza-1(5,3)-pyrazolo[1,5-a]pyrimidina-2(2,1)-bicyclo[3.1.0]hexana-3(1,2)-benzenacyclooctaphan-8-one (3) was prepared according to the synthetic method of example 1 by replacing (R)-2-((tert-butoxycarbonyl)-amino)propyl methanesulfonate (1c) with (R)-1-((tert-butoxycarbonyl)amino)propan-2-yl methanesulfonate. MS-ESI (m/z): 394 [M+1]$^+$.

Example 4

(S,3'E,4E)-5'-fluoro-6'-methylspiro[cyclopropane-1,3'-5-oxa-2,8-diaza-1(5,3)-pyrazolo[1,5-a]pyrimidina-4(7,2)-benzenacyclononaphan]-9'-one (4)

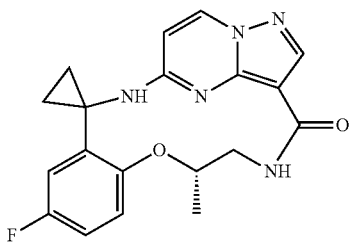

The title compound (S,3'E,4'E)-5'-fluoro-6'-methylspiro[cyclopropane-1,3'-5-oxa-2,8-diaza-1(5,3)-pyrazolo[1,5-a]pyrimidina-4(1,2)-benzenacyclononaphan]-9'-one (4) was prepared according to the synthetic method of example 2 by replacing (R)-2-((tert-butoxycarbonyl)-amino)propyl methanesulfonate (1c) with (R)-1-((tert-butoxycarbonyl)amino)propan-2-yl methanesulfonate. MS-ESI (m/z): 368 [M+1]$^+$.

Example 5

(1$^3$E,1$^4$E,6R)-3$^5$-fluoro-6-methyl-2$^2$,7-diaza-1(5,3)-pyrazolo[1,5-a]pyrimidina-3(3,2)-pyridina-2(2,1)-bicyclo[3.1.0]hexanacyclooctaphan-8-one (5)

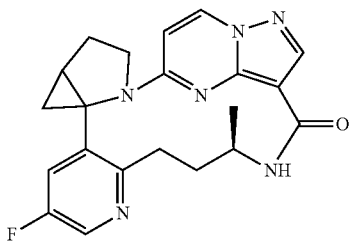

Ethyl 5-(1-(2-(benzyloxy)-5-fluoropyridin-3-yl)-2-azabicyclo[3.1.0]hexan-2-yl)pyrazolo[1,5-a]pyrimidine-3-carboxylate (5a)

The mixture of ethyl 5-chloropyrazolo[1,5-a]pyrimidine-3-carboxylate (1a) (44 mg, 0.20 mmol), 1-(2-(benzyloxy)-5-fluoropyridin-3-yl)-2-azabicyclo[3.1.0]hexane trifluoroacetate (C) (37 mg, 0.13 mmol) and DIPEA (98 mg, 0.78 mmol) in n-BuOH (3.5 mL) was stirred at 120° C. for 12 h. The reaction was cooled to r.t., quenched with water and extracted with EtOAc. The extracts were washed with water and brine, dried over Na$_2$SO$_4$, and concentrated. The residue was purified by column chromatography on silica gel, eluting with PE/EtOAc (3:1) to give the title compound ethyl 5-(1-(2-(benzyloxy)-5-fluoropyridin-3-yl)-2-azabicyclo[3.1.0]hexan-2-yl)pyrazolo[1,5-a]pyrimidine-3-carboxylate (5a). MS-ESI (m/z): 474 [M+1]$^+$.

Ethyl 5-(1-(5-fluoro-2-hydroxypyridin-3-yl)-2-azabicyclo[3.1.0]hexan-2-yl)pyrazolo[1,5-a]pyrimidine-3-carboxylate (5b)

To a solution of ethyl 5-(1-(2-(benzyloxy)-5-fluoropyridin-3-yl)-2-azabicyclo hexan-2-yl)pyrazolo[1,5-a]pyrimidine-3-carboxylate (5a) (69 mg, 0.15 mmol) in DCM (5 mL) was added TFA (5 mL) at RT and stirred at RT for 21 h. The reaction mixture was concentrated, quenched with water and extracted with DCM. The extracts were washed sequentially with water and sat. NaHCO$_3$, dried over Na$_2$SO$_4$. The solvents were evaporated to give ethyl 5-(1-(5-fluoro-2-hydroxypyridin-3-yl)-2-azabicyclo[3.1.0]hexan-2-yl)pyrazolo[1,5-a]pyrimidine-3-carboxylate (5b) as crude, which was used in next step without further purification. MS-ESI (m/z): 384 [M+1]$^+$.

Ethyl 5-(1-(5-fluoro-2-(((trifluoromethyl)sulfonyl)oxy)pyridin-3-yl)-2-azabicyclo[3.1.0]hexan-2-yl)pyrazolo[1,5-a]pyrimidine-3-carboxylate (5c)

To a solution of ethyl 5-(1-(5-fluoro-2-hydroxypyridin-3-yl)-2-azabicyclo[3.1.0]-hexan-2-yl)pyrazolo[1,5-a]pyrimidine-3-carboxylate (5b) (40 mg, 0.10 mmol) in DCM (8 mL) was added Tf$_2$O (88.4 mg, 0.310 mmol) and pyridine (83 mg, 1.0 mmol) at 0° C. The mixture was stirred at RT for overnight. The reaction was quenched with water and extracted with DCM. The extracts were washed sequentially with water and brine, dried over Na$_2$SO$_4$, and concentrated. The residue was purified by column chromatography on silica gel, eluting with PE/EtOAc (3:1) to give the title compound ethyl 5-(1-(5-fluoro-2-(((trifluoromethyl)sulfonyl)oxy)-pyridin-3-yl)-2-azabicyclo[3.1.0]hexan-2-yl)pyrazolo[1,5-a]pyrimidine-3-carboxylate (5c). MS-ESI (m/z): 516 [M+1]$^+$.

tert-Butyl (R)-but-3-yn-2-ylcarbamate (5d)

The title compound tert-butyl (R)-but-3-yn-2-ylcarbamate (5d) was prepared according to the method described in WO 2006/065703.

Ethyl 5-(1-(2-((R)-3-((tert-butoxycarbonyl)amino)but-1-yn-1-yl)-5-fluoropyridin-3-yl)-2-azabicyclo[3.1.0]hexan-2-yl)pyrazolo[1,5-a]pyrimidine-3-carboxylate (5e)

To a solution of ethyl 5-(1-(5-fluoro-2-(((trifluoromethyl)sulfonyl)oxy)pyridin-3-yl)-2-azabicyclo[3.1.0]hexan-2-yl)pyrazolo[1,5-a]pyrimidine-3-carboxylate (5c) (23 mg, 0.045 mmol) and tert-butyl (R)-but-3-yn-2-ylcarbamate (5d) (30.2 mg, 0.180 mmol) in DMF (0.5 mL) was added Pd(PPh$_3$)$_2$C$_{1-2}$ (6.3 mg, 0.0089 mmol), CuI (1.7 mg, 0.0089 mmol) and DIPEA (29 mg, 0.22 mmol). The resulting mixture was heated at 80° C. for 18 h at the atmosphere of N$_2$. The reaction was cooled to RT, quenched with water and extracted with EtOAc. The extracts were washed with water and brine, dried over Na$_2$SO$_4$, and concentrated. The residue was purified by column chromatography on silica gel, eluting with PE/EtOAc (1.5:1) to give the title compound ethyl 5-(1-(2-((R)-3-((tert-butoxycarbonyl)amino)but-1-yn-1-yl)-5-fluoropyridin-3-yl)-2-azabicyclo[3.1.0]-hexan-2-yl)pyrazolo[1,5-a]pyrimidine-3-carboxylate (5e). MS-ESI (m/z): 535 [M+1]$^+$.

Ethyl 5-(1-(2-((R)-3-((tert-butoxycarbonyl)amino)butyl)-5-fluoropyridin-3-yl)-2-azabicyclo[3.1.0]hexan-2-yl)pyrazolo[5-a]pyrimidine-3-carboxylate (5f)

The mixture of ethyl 5-(1-(2-((R)-3-((tert-butoxycarbonyl)amino)but-1-yn-1-yl)-5-fluoropyridin-3-yl)-2-azabicyclo[3.1.0]hexan-2-yl)pyrazolo[1,5-a]pyrimidine-3-carboxylate (5e) (20 mg, 0.037 mmol) and Pd(OH)$_2$/C (20%, 8 mg) in MeOH (5 mL) was stirred at RT for 5 h at the atmosphere of H$_2$ (1 atm). Then the mixture was filtered, and the filtrate was concentrated. The residue was purified by preparative TLC, eluting with DCM/MeOH (30:1) to give the title compound ethyl 5-(1-(2-((R)-3-((tert-butoxycarbonyl)amino)butyl)-5-fluoropyridin-3-yl)-2-azabicyclo[3.1.0]hexan-2-yl)pyrazolo[1,5-a]pyrimidine-3-carboxylate (5f). MS-ESI (m/z): 539 [M+1]$^+$.

5-(1-(2-((R)-3-((tert-butoxycarbonyl)amino)butyl)-5-fluoropyridin-3-yl)-2-azabicyclo[3.1.0]hexan-2-yl) pyrazolo[1,5-a]pyrimidine-3-carboxylic acid (5 g)

A mixture of ethyl 5-(1-(2-((R)-3-((tert-butoxycarbonyl)amino)butyl)-5-fluoropyridin-3-yl)-2-azabicyclo[3.1.0]hexan-2-yl)pyrazolo[1,5-a]pyrimidine-3-carboxylate (5f) (12 mg, 0.022 mmol) and LiOH.H$_2$O (10 mg, 0.22 mmol) in MeOH/H$_2$O (5 mL/1 mL) was stirred at 70° C. for 17 h. The mixture was cooled to RT and concentrated. The residue was acidified to pH=4~5 with 1 N HCl aqueous solution and extracted with EtOAc. The extracts were washed with brine, dried over Na$_2$SO$_4$, and concentrated to give the title compound 5-(1-(2-((R)-3-((tert-butoxycarbonyl)amino)butyl)-5-fluoropyridin-3-yl)-2-azabicyclo[3.1.0]hexan-2-yl)pyrazolo[1,5-a]p yrimidine-3-carboxylic acid (5 g). MS-ESI (m/z): 511 [M+1]$^+$.

(2R)-4-(3-(2-(3-carboxypyrazolo[1,5-a]pyrimidin-5-yl)-2-azabicyclo[3.1.0]hexan-1-yl)-5-fluoropyridin-2-yl)butan-2-aminium 2,2,2-trifluoroacetate (5h)

To a solution of 5-(1-(2-((R)-3-((tert-butoxycarbonyl)amino)butyl)-5-fluoropyridin-3-yl)-2-azabicyclo[3.1.0]hexan-2-yl)pyrazolo[1,5-a]pyrimidine-3-carboxylic acid (5 g) (11.4 mg, 0.0220 mmol) in DCM (6 mL) at 0° C. was added TFA (2 mL). The mixture was stirred at RT for 40 min, and concentrated to give (2R)-4-(3-(2-(3-carboxypyrazolo[1,5-a]-pyrimidin-5-yl)-2-azabicyclo[3.1.0]hexan-1-yl)-5-fluoropyridin-2-yl)butan-2-aminium 2,2,2-trifluoroacetate (5h) as crude, which was used in next step without further purification. MS-ESI (m/z): 411 [M+1]$^+$.

(1$^3$E,1$^4$E,6R)-3$^5$-fluoro-6-methyl-2$^2$,7-diaza-1(5,3)-pyrazolo[1,5-a]pyrimidina-3(3,2)-pyridina-2(2,1)-bicyclo[3.1.0]hexanacyclooctaphan-8-one (5)

To a solution of (2R)-4-(3-(2-(3-carboxypyrazolo[1,5-a]pyrimidin-5-yl)-2-azabicyclo[3.1.0]hexan-1-yl)-5-fluoropyridin-2-yl)butan-2-aminium 2,2,2-trifluoroacetate (5h) (10 mg, 0.022 mmol) in DMF (10 mL) at RT was added FDPP (9.0 mg, 0.022 mmol) and DIPEA (30.0 mg, 0.22 mmol). The resulting mixture was stirred at RT for overnight. Then the mixture was diluted with water (50 mL) and extracted with EtOAc. The extracts were washed with brine (40 mL), dried over Na$_2$SO$_4$ and concentrated. The residue was purified by preparative TLC, eluting with DCM/MeOH (25:1) to give the title compound (1$^3$E,1$^4$E,6R)-3$^5$-fluoro-6-methyl-2$^2$,7-diaza-1(5,3)-pyrazolo[1,5-a]pyrimidina-3(3,2)-pyridina-2(2,1)-bicyclo[3.1.0]hexanacyclooctaphan-8-one (5). MS-ESI (m/z): 393 [M+1]$^+$.

Example 6

(1$^3$E,1$^4$E,6R)-3$^5$-fluoro-6-methyl-4-oxa-2$^2$,7-diaza-1 (5,3)-pyrazolo[1,5-a]-pyrimidina-3(3,2)-pyridina-2 (2,1)-bicyclo[3.1.0]hexanacyclooctaphan-8-one (6)

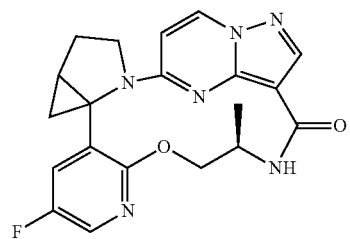

6

Ethyl 5-(1-(2-((R)-2-((tert-butoxycarbonyl)amino) propoxy)-5-fluoropyridin-3-yl)-2-azabicyclo[3.1.0] hexan-2-yl)pyrazolo[1,5-a]pyrimidine-3-carboxylate (6a)

To a solution of ethyl 5-(1-(5-fluoro-2-hydroxypyridin-3-yl)-2-azabicyclo[3.1.0]hexan-2-yl)pyrazolo[1,5-a]pyrimidine-3-carboxylate (5b) (15 mg, 0.039 mmol) in DMF (4 mL) was added Cs$_2$CO$_3$ (102 mg, 0.313 mmol). The mixture was heated to 70° C. and stirred for 30 min. Then (R)-2-((tert-butoxycarbonyl)amino)propyl methanesulfonate (1c) (60 mg, 0.24 mmol) was added, the mixture was stirred at 70° C. for 3 h. After that the mixture was cooled to RT, diluted with water, and extracted with EtOAc. The extracts were washed with brine, dried over Na$_2$SO$_4$, and concentrated. The residue was purified by preparative TLC eluting with DCM/MeOH (30:1) to give the title compound ethyl 5-(1-(2-((R)-2-((tert-butoxycarbonyl)amino)propoxy)-5-fluoropyridin-3-yl)-2-azabicyclo[3.1.0]hexan-2-yl)pyrazolo-[1,5-a]pyrimidine-3-carboxylate (6a). MS-ESI (m/z): 541 [M+1]$^+$.

5-(1-(2-((R)-2-((tert-butoxycarbonyl)amino) propoxy)-5-fluoropyridin-3-yl)-2-azabicyclo[3.1.0] hexan-2-yl)pyrazolo[1,5-a]pyrimidine-3-carboxylic Acid (6b)

A mixture of ethyl 5-(1-(2-((R)-2-((tert-butoxycarbonyl)amino)propoxy)-5-fluoropyridin-3-yl)-2-azabicyclo[3.1.0]hexan-2-yl)pyrazolo[1,5-a]pyrimidine-3-carboxylate (6a) (28 mg, 0.052 mmol) and LiOH.H$_2$O (22 mg, 0.52 mmol) in MeOH/H$_2$O (5 mL/1 mL) was stirred at 70° C. for 17 h. The mixture was cooled to RT and concentrated. The residue was acidified to pH=5 with 1 N HCl aqueous solution and extracted with DCM. The organic layer was washed with brine, dried over Na$_2$SO$_4$, and concentrated to give the title compound 5-(1-(2-((R)-2-((tert-butoxycarbonyl)amino) propoxy)-5-fluoropyridin-3-yl)-2-azabicyclo[3.1.0]hexan-2-yl)pyrazolo-[1,5-a]pyrimidine-3-carboxylic acid (6b). MS-ESI (m/z): 513 [M+1]$^+$.

(2R)-1-((3-(2-(3-carboxypyrazolo[1,5-a]pyrimidin-5-yl)-2-azabicyclo[3.1.0]hexan-1-yl)-5-fluoropyridin-2-yl)oxy)propan-2-aminium 2,2,2-trifluoroacetate (6c)

To a solution of 5-(1-(2-((R)-2-((tert-butoxycarbonyl)amino)propoxy)-5-fluoropyridin-3-yl)-2-azabicyclo[3.1.0]

hexan-2-yl)pyrazolo[1,5-a]pyrimidine-3-carboxylic acid (6b) (26.5 mg, 0.0520 mmol) in DCM (2 mL) at 0° C. was added TFA (0.7 mL). The mixture was stirred at RT for 40 min, and concentrated to give (2R)-1-((3-(2-(3-carboxy-pyrazolo-[1,5-a]pyrimidin-5-yl)-2-azabicyclo[3.1.0]hexan-1-yl)-5-fluoropyridin-2-yl)oxy)propan-2-aminium 2,2,2-trifluoroacetate (6c) as crude, which was used in next step without further purification. MS-ESI (m/z): 413 [M+1]$^+$.

($1^3$E,$1^4$E,6R)-$3^5$-fluoro-6-methyl-4-oxa-$2^2$,7-diaza-1(5,3)-pyrazolo[1,5-a]pyrimidina-3(3,2)-pyridina-2(2,1)-bicyclo[3.1.0]hexanacyclooctaphan-8-one (6)

To a solution of (2R)-1-((3-(2-(3-carboxypyrazolo[1,5-a]pyrimidin-5-yl)-2-azabicyclo[3.1.0]hexan-1-yl)-5-fluoro-pyridin-2-yl)oxy)propan-2-aminium 2,2,2-trifluoroacetate (6c) (21.4 mg, 0.0520 mmol) in DMF (15 mL) at RT was added FDPP (20.0 mg, 0.0520 mmol) and DIPEA (65.0 mg, 0.520 mmol). The resulting mixture was stirred at RT for 18 h. Then the mixture was diluted with water (100 mL) and extracted with EtOAc. The extracts were washed with brine (40 mL), dried over Na$_2$SO$_4$ and concentrated. The residue was purified by preparative TLC eluting with DCM/MeOH (20:1) to give the title compound ($1^3$E,$1^4$E,6R)-$3^5$-fluoro-6-methyl-4-oxa-$2^2$,7-diaza-1(5,3)-pyrazolo[1,5-a]pyrimidina-3(3,2)-pyridina-2(2,1)-bicyclo[3.1.0]hexanacyclooctaphan-8-one (6). MS-ESI (m/z): 395 [M+1]$^+$.

Example 7

($1^3$E,$1^4$E,5S)-$3^5$-fluoro-5-methyl-4-oxa-$2^2$,7-diaza-1(5,3)-pyrazolo[1,5-a]pyrimidina-3(3,2)-pyridina-2(2,1)-bicyclo[3.1.0]hexanacyclooctaphan-8-one (7)

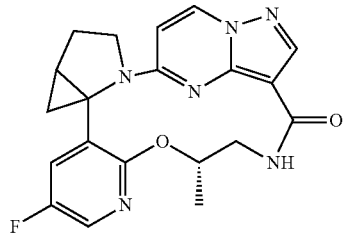

7

The title compound ($1^3$E,$1^4$E,5S)-$3^5$-fluoro-5-methyl-4-oxa-$2^2$,7-diaza-1(5,3)-pyrazolo[1,5-a]pyrimidina-3(3,2)-pyridina-2(2,1)-bicyclo[3.1.0]hexanacyclooctaphan-8-one (7) was prepared according to the synthetic method of example 6 by replacing (R)-2-((tert-butoxycarbonyl)amino)propyl methanesulfonate (1c) with (R)-1-((tert-butoxy-carbonyl)-amino)propan-2-yl methanesulfonate. MS-ESI (m/z): 395 [M+1]$^+$.

Example 8

(R,3'E,4'E)-5'-fluoro-7'-methylspiro[cyclopropane-1,3'-5-oxa-2,8-diaza-1(5,3)-pyrazolo[1,5-a]pyrimidina-4(3,2)-pyridinacyclononaphan]-9'-one (8)

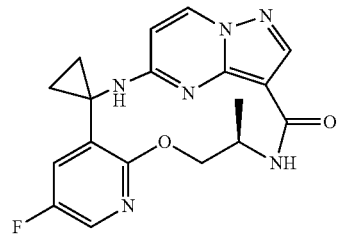

8

5-((1-(5-Fluoro-2-hydroxypyridin-3-yl)cyclopropyl)amino)pyrazolo[1,5-a]pyrimidine-3-carboxylic acid (8a)

To a solution of ethyl 5-((1-(5-fluoro-2-hydroxypyridin-3-yl)cyclopropyl)amino)-pyrazolo[1,5-a]pyrimidine-3-carboxylate (D) (36 mg, 0.10 mmol) in THF-MeOH (1:1, 1.5 mL) was added 5 N NaOH (1 mL). The mixture was stirred at RT for 16 h. The mixture was acidified with 3N HCl to pH=2~3. The mixture was loaded on silica gel column and eluted with 10% MeOH in DCM to give 5-((1-(5-fluoro-2-hydroxypyridin-3-yl)cyclopropyl)amino)pyrazolo-[1,5-a]pyrimidine-3-carboxylic acid (8a). MS-ESI (m/z): 330 [M+1]$^+$.

(R)-5-((1-(5-fluoro-2-hydroxypyridin-3-yl)cyclopropyl)amino)-N-(1-hydroxypropan-2-yl)pyrazolo[1,5-a]pyrimidine-3-carboxamide (8b)

To a solution of 5-((1-(5-fluoro-2-hydroxypyridin-3-yl)cyclopropyl)amino)-pyrazolo[1,5-a]pyrimidine-3-carboxylic acid (8a) (32.2 mg, 0.0980 mmol) in DMF (1.0 mL) was added D-alaninol (14.7 mg, 0.196 mmol), HATU (56.0 mg, 0.147 mmol) and DIPEA (25.0 mg, 0.196 mmol). The mixture was stirred at RT for 2 h. The mixture was diluted with water (10 mL) and extracted with EtOAc. The extracts were washed with brine, dried (Na$_2$SO$_4$), and concentrated. The residue was purified by column chromatography on silica gel, eluting with 5-10% MeOH in DCM to give (R)-5-((1-(5-fluoro-2-hydroxypyridin-3-yl)cyclopropyl)amino)-N-(1-hydroxypropan-2-yl)pyrazolo[1,5-a]pyrimidine-3-carboxamide (8b). MS-ESI (m/z): 387 [M+1]$^+$.

(R,3'E,4'E)-5'-fluoro-7'-methyl-2'-(methylsulfonyl)spiro[cyclopropane-1,3'-5-oxa-2,8-diaza-1(5.3)-pyrazolo[1,5-a]pyrimidina-4(3,2)-pyridinacyclononaphan]-9'-one (8c)

To a solution of (R)-5-((1-(5-fluoro-2-hydroxypyridin-3-yl)cyclopropyl)amino)-N-(1-hydroxypropan-2-yl)pyrazolo[1,5-a]pyrimidine-3-carboxamide (8b) (13.6 mg, 0.0352 mmol) in DCM (0.5 mL) was added methanesulfonyl chloride (23 mg, 0.20 mmol) and TEA (35 mg, 0.35 mmol). The mixture was stirred at RT for 5 h. The mixture was diluted with water (5 mL) and extracted with EtOAc. The extracts were washed with brine, dried (Na$_2$SO$_4$), and concentrated. The residue was purified by column chromatography on silica gel, and eluted with 5% MeOH in DCM to give (R,3'E,4'E)-5'-fluoro-7'-methyl-2'-(methylsulfonyl)spiro[cyclopropane-1,3'-5-oxa-2,8-diaza-1(5,3)-pyrazolo[1,5-a]pyrimidina-4(3,2)-pyridinacyclononaphan]-9'-one (8c). MS-ESI (m/z): 447 [M+1]⁺.

(7'R,E)-3a'-bromo-5'-fluoro-7'-methylspiro[cyclopropane-1,3'-5-oxa-2,8-diaza-1(5,3)-pyrazolo[1,5-a]pyrimidina-4(3,2)-pyridinacyclononaphan]-9'-one (8d)

To a solution of (R,3'E,4'E)-5'-fluoro-7'-methyl-2'-(methylsulfonyl)spiro-[cyclopropane-1,3'-5-oxa-2,8-diaza-1(5,3)-pyrazolo[1,5-a]pyrimidina-4(3,2)-pyridinacyclononaphan]-9'-one (8c) (7.5 mg, 0.017 mmol) in 32% HBr—HOAc (0.5 mL). The mixture was heated at 85° C. for 1 h. The solvents were evaporated to give crude (7'R,E)-3a'-bromo-5'-fluoro-7'-methylspiro[cyclopropane-1,3'-5-oxa-2,8-diaza-1(5,3)-pyrazolo[1,5-a]pyrimidina-4(3,2)-pyridinacyclononaphan]-9'-one (8d), which was used in next step without further purification. MS-ESI (m/z): 449/451 (1:1) [M+1]⁺.

(R,3'E,4'E)-5'-fluoro-7'-methylspiro[cyclopropane-1,3'-5-oxa-2,8-diaza-1(5,3)-pyrazolo[1,5-a]pyrimidina-4(3,2)-pyridinacyclononaphan]-9'-one (8)

To a solution of above crude (7'R,E)-3a'-bromo-5'-fluoro-7'-methylspiro[cyclopropane-1,3'-5-oxa-2,8-diaza-1(5,3)-pyrazolo[1,5-a]pyrimidina-4(3,2)-pyridinacyclononaphan]-9'-one (8d) in MeOH (0.5 mL) was added 5 N NaOH (0.5 mL). The mixture was stirred at RT for 4 h. The mixture was diluted with water and extracted with DCM. The extracts were washed with brine, dried (Na₂SO₄), and the solvents were evaporated. The residue was purified by column chromatography on a silica gel, eluting with DCM-MeOH—NH₄OH (92:7:1) to give (R,3'E,4'E)-5'-fluoro-7'-methylspiro[cyclopropane-1,3'-5-oxa-2,8-diaza-1(5,3)-pyrazolo[1,5-a]pyrimidina-4(3,2)-pyridinacyclononaphan]-9'-one (8). MS-ESI (m/z): 369 [M+1]⁺.

Example 9

(S,3'E,4'E)-5'-fluoro-6'-methylspiro[cyclopropane-1,3'-5-oxa-2,8-diaza-1(5,3)-pyrazolo[1,5-a]pyrimidina-4(3,2)-pyridinacyclononaphan]-9'-one (9)

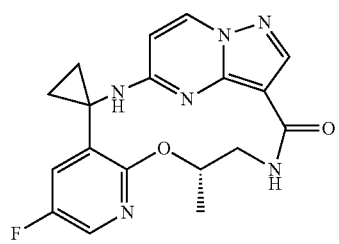

(R)-1-((tert-butoxycarbonyl)amino)propan-2-yl methanesulfonate (9a)

To a solution of tert-butyl (R)-(2-hydroxypropyl)carbamate (780 mg, 4.46 mmol) in DCM (10 mL) was added methanesulfonyl chloride (536 mg, 4.68 mmol) and TEA (744 mg, 7.37 mmol). The mixture was stirred at RT for 2 h. The solvents were evaporated, the residue was dissolved in EtOAc (50 mL). The solution was washed with water and brine, dried (Na₂SO₄), and concentrated to give (R)-1-((tert-butoxycarbonyl)amino)propan-2-yl methanesulfonate (9a). MS-ESI (m/z): 276 [M+23]⁺.

Ethyl (S)-5-((1-(2-((1-((tert-butoxycarbonyl)amino)propan-2-yl)oxy)-5-fluoropyridin-3-yl)cyclopropyl)amino)pyrazolo[1,5-a]pyrimidine-3-carboxylate (9b)

To a solution of ethyl 5-((1-(5-fluoro-2-hydroxypyridin-3-yl)cyclopropyl)-amino)pyrazolo[1,5-a]pyrimidine-3-carboxylate (D) (47.0 mg, 0.132 mmol) in DMF (1 mL) was added (R)-1-((tert-butoxycarbonyl)amino)propan-2-yl methanesulfonate (9a) (50.0 mg, 0.197 mmol) and Cs₂CO₃ (52.0 mg, 0.158 mmol). The mixture was heated at 70° C. for 3 h. The mixture was diluted with water and extracted with EtOAc. The extracts were washed with brine, dried (Na₂SO₄), and the solvents were evaporated. The residue was purified by silica gel chromatography, eluting with 30% EtOAc in hexane to give ethyl (S)-5-((1-(2-((1-((tert-butoxycarbonyl)amino)-propan-2-yl)oxy)-5-fluoropyridin-3-yl)cyclopropyl)amino)pyrazolo[1,5-a]pyrimidine-3-carboxylate (9b). MS-ESI (m/z): 515 [M+1]⁺.

(S)-5-((1-(2-((1-aminopropan-2-yl)oxy)-5-fluoropyridin-3-yl)cyclopropyl)amino)-pyrazolo[1,5-a]pyrimidine-3-carboxylic acid (9c)

To a solution of ethyl (S)-5-((1-(2-((1-((tert-butoxycarbonyl)amino)propan-2-yl)oxy)-5-fluoropyridin-3-yl)cyclopropyl)amino)pyrazolo[1,5-a]pyrimidine-3-carboxylate (9b) (27.1 mg, 0.0527 mmol) in 1:1 MeOH-THF (1.5 mL) was added 5 N NaOH (1 mL). The mixture was heated at 60° C. for 4 h. The mixture was cooled to RT, diluted with water (6 mL), acidified with 3 N HCl to pH=3~4, and extracted with EtOAc. The extracts were dried (Na₂SO₄), and the solvent was evaporated to give the crude acid. The crude acid was dissolved in DCM (1 mL) and TFA (0.5 mL) was added. The mixture was stirred at RT for 1 h. The solvents were evaporated to give the crude amino acid as TFA salt of (S)-5-((1-(2-((1-aminopropan-2-yl)oxy)-5-fluoropyridin-3-yl)cyclopropyl)amino)pyrazolo[1,5-a]pyrimidine-3-carboxylic acid (9c). MS-ESI (m/z): 387 [M+1]⁺.

(S,3'E,4'E)-5'-fluoro-6'-methylspiro[cyclopropane-1,3'-5-oxa-2,8-diaza-1(5,3)-pyrazolo[1,5-a]pyrimidina-4(3,2)-pyridinacyclononaphan]-9'-one (9)

To a solution of (S)-5-((1-(2-((1-aminopropan-2-yl)oxy)-5-fluoropyridin-3-yl)cyclopropyl)amino)pyrazolo[1,5-a]pyrimidine-3-carboxylic acid (9c) (10 mg, 0.026 mmol) in DMF (0.3 mL) was added HATU (14.8 mg, 0.0390 mmol) and DIPEA (13.4 mg, 0.104 mmol). The mixture was stirred at RT for 14 h. The mixture was diluted with water and extracted with EtOAc. The extracts were washed with brine, dried (Na₂SO₄), and the solvents were evaporated. The residue was purified by preparative TLC on silica gel, eluting with 90:10:0.5 DCM-MeOH—NH₄OH to give (S,3'E,4'E)-5'-fluoro-6'-methylspiro[cyclopropane-1,3'-5-oxa-2,8-diaza-1(5,3)-pyrazolo[1,5-a]pyrimidina-4(3,2)-pyridinacyclononaphan]-9'-one (9). MS-ESI (m/z): 369 [M+1]⁺.

Example 10

(R,3'E,4'E)-5'-fluoro-7'-methylspiro[cyclopropane-1,3'-2,8-diaza-1(5,3)-pyrazolo[1,5-a]pyrimidina-4(3,2)-pyridinacyclononaphan]-9'-one (10)

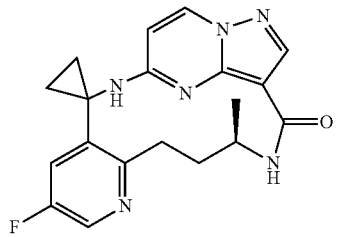

Ethyl 5-((1-(5-fluoro-2-(((trifluoromethyl(sulfonyl)oxy)pyridin-3-yl)cyclopropyl)-amino)pyrazolo[1,5-a]pyrimidine-3-carboxylate (10a)

To a solution of ethyl 5-((1-(5-fluoro-2-hydroxypyridin-3-yl)cyclopropyl) amino)pyrazolo[1,5-a]pyrimidine-3-carboxylate (D) (105 mg, 0.294 mmol) in DCM (20 mL) at 0° C. was added pyridine (231 mg, 2.92 mmol) and triflic anhydride (248 mg, 0.879 mmol). The mixture was stirred at RT for 1 h. The reaction was diluted with water and extracted with DCM (2×). The extracts were washed with brine, dried (Na$_2$SO$_4$), and concentrated. The crude product was purified by silica gel chromatography, eluting with 30% EtOAc in hexane to give ethyl 5-((1-(5-fluoro-2-(((trifluoromethyl)sulfonyl)oxy)pyridin-3-yl)cyclopropyl)amino)pyrazolo[1,5-a]pyrimidine-3-carboxylate (10a). MS-ESI (m/z): 490 [M+1]$^+$.

Ethyl (R)-5-((1-(2-(3-((tert-butoxycarbonyl)amino)but-1-yn-1-yl)-5-fluoropyridin-3-yl)cyclopropyl)amino)pyrazolo[1,5-a]pyrimidine-3-carboxylate (10b)

To a solution of 5-((1-(5-fluoro-2-(((trifluoromethyl)sulfonyl)oxy)pyridin-3-yl)cyclopropyl)amino) pyrazolo[1,5-a]pyrimidine-3-carboxylate (10a) (112 mg, 0.229 mmol) and tert-butyl (R)-but-3-yn-2-ylcarbamate (77.4 mg, 0.460 mmol) in DMF (4 mL) was added CuI (8.8 mg, 0.046 mmol), Pd(PPh$_3$)$_2$Cl$_{1-2}$ (32.3 mg, 0.0460 mmol), and diisopropylamine (58 mg, 0.57 mmol). The mixture was heated at 80° C. for 2 h. After cooling to RT, the reaction was diluted with water and extracted with EtOAc (2×). The extracts were washed with brine, dried (Na$_2$SO$_4$), and concentrated. The residue was purified by silica gel chromatography, eluting with 40% EtOAc in hexane to give ethyl (R)-5-((1-(2-(3-((tert-butoxycarbonyl)amino)but-1-yn-1-yl)-5-fluoropyridin-3-yl)cyclopropyl)amino)pyrazolo[1,5-a]pyrimidine-3-carboxylate (10b). MS-ESI (m/z): 509 [M+1]$^+$.

Ethyl (R)-5-((1-(2-(3-((tert-butoxycarbonyl)amino)butyl)-5-fluoropyridin-3-yl)cyclopropyl)amino)pyrazolo[1,5-a]pyrimidine-3-carboxylate (10c)

To a solution of ethyl (R)-5-((1-(2-(3-((tert-butoxycarbonyl)amino)but-1-yn-1-yl)-5-fluoropyridin-3-yl)cyclopropyl)amino)pyrazolo[1,5-a]pyrimidine-3-carboxylate (10b) (116 mg, 0.228 mmol) in MeOH (5 mL) was added Pd(OH)$_2$ on carbon (20%, contain 50% H$_2$O, 60 mg). The mixture was stirred at 1 atmosphere of H$_2$ for 2 h. The catalyst was removed by filtration and the filter cake was washed with MeOH. The filtrate was concentrated. The residue was purified by silica gel chromatography, eluting with 40% EtOAc in hexane to give ethyl (R)-5-((1-(2-(3-((tert-butoxycarbonyl)amino)butyl)-5-fluoropyridin-3-yl)cyclopropyl)amino)pyrazolo[1,5-a]pyrimidine-3-carboxylate (10c). MS-ESI (m/z): 513 [M+1]$^+$.

(R)-5-((1-(2-(3-aminobutyl)-5-fluoropyridin-3-yl)cyclopropyl)amino)pyrazolo-[1,5-a]pyrimidine-3-carboxylate acid (10d)

To a solution of ethyl (R)-5-((1-(2-(3-((tert-butoxycarbonyl)amino)butyl)-5-fluoropyridin-3-yl)cyclopropyl)amino)pyrazolo[1,5-a]pyrimidine-3-carboxylate (10c) (91.4 mg, 0.178 mmol) in 1:1 MeOH-THF (4.5 mL) was added 5 N NaOH (3 mL). The mixture was heated at 60° C. for 3 h. The mixture was cooled to RT, diluted with water (20 mL), acidified with 3 N HCl to pH=3~4, and extracted with EtOAc. The extracts were dried (Na$_2$SO$_4$), and the solvents were evaporated to give the crude acid. The crude acid was dissolved in 4 N HCl-dioxane (3 mL). The mixture was stirred at RT for 1 h. The solvents were evaporated to give the crude amino acid as HCl salt of (R)-5-((1-(2-(3-aminobutyl)-5-fluoropyridin-3-yl)cyclopropyl)amino)pyrazolo[1,5-a]pyrimidine-3-carboxylic acid (10d). MS-ESI (m/z): 385 [M+1]$^+$.

(R,3'E,4'E)-5'-fluoro-7'-methylspiro[cyclopropane-1,3'-2,8-diaza-1(5,3)-pyrazolo[1,5-a]pyrimidina-4(3,2)-pyridinacyclononaphan]-9'-one (10)

To a solution of (R)-5-((1-(2-(3-aminobutyl)-5-fluoropyridin-3-yl)cyclopropyl) amino)pyrazolo[1,5-a]pyrimidine-3-carboxylic acid hydrochloride (10d) (20 mg, 0.044 mmol) in DMF (2 mL) was added DIPEA (49 mg, 0.38 mmol). FDPP (40 mg, 0.104 mmol) was added in 4 portions during 3 h. The mixture was stirred at RT for 14 h. The mixture was diluted with water and extracted with EtOAc. The extracts were washed with brine, dried (Na$_2$SO$_4$), and the solvents were evaporated. The residue was purified by preparative TLC on silica gel, eluting with 90:10:0.5 DCM-MeOH—NH$_4$OH to give (R,3'E,4'E)-5'-fluoro-7'-methylspiro[cyclopropane-1,3'-2,8-diaza-1(5,3)-pyrazolo[1,5-a]pyrimidina-4(3,2)-pyridinacyclononaphan]-9'-one (10). MS-ESI (m/z): 367 [M+1]$^+$.

Example 11

(R,3'E,4'E)-5'-fluoro-2'7'-dimethylspiro[cyclopropane-1,3'-5-oxa-2,8-diaza-1(5.3)-pyrazolo[1,5-a]pyrimidina-4(1,2)-benzenacyclononaphan]-9'-one (111

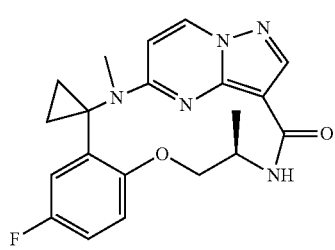

The title compound (R,3'E,4'E)-5'-fluoro-2',7'-dimethyl-spiro[cyclopropane-1,3'-5-oxa-2,8-diaza-1(5,3)-pyrazolo[1,5-a]pyrimidina-4(1,2)-benzenacyclononaphan]-9'-one (11) was prepared according to the synthetic method of example 2 by replacing 1-(2-(benzyloxy)-5-fluorophenyl)-cyclopropan-1-amine (B) with 1-(2-(benzyloxy)-5-fluorophenyl)-A-methylcyclopropan-1-amine 2,2,2-trifluoroacetate (E). MS-ESI (m/z): 382 [M+1]$^+$.

Example 12

($1^3$E,$1^4$E,6R)-$3^5$-fluoro-6-methyl-$2^2$,7-diaza-1(5,3)-pyrazolo[1,5-a]pyrimidina-2(2,1)-bicyclo[3.1.0]hexana-3(1,2)-benzenacyclooctaphan-8-one (12A and 12B)

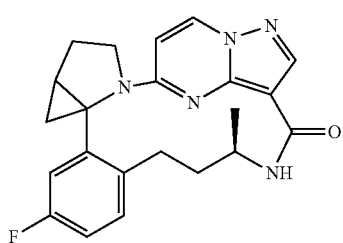

12A and 12B

Ethyl 5-(1-(5-fluoro-2-(((trifluoromethyl)sulfonyl)oxy)phenyl)-2-azabicyclo-[3.1.0]hexan-2-yl)pyrazolo[1,5-a]pyrimidine-3-carboxylate (12a)

The title compound ethyl 5-(1-(5-fluoro-2-(((trifluoromethyl)sulfonyl)oxy)-phenyl)-2-azabicyclo-[3.1.0]hexan-2-yl)pyrazolo[1,5-a]pyrimidine-3-carboxylate (12a) was prepared according to the synthetic method of ethyl 5-(1-(5-fluoro-2-(((trifluoromethyl)sulfonyl) oxy)-pyridin-3-yl)-2-azabicyclo[3.1.0]hexan-2-yl)pyrazolo[1,5-a]-pyrimidine-3-carboxylate (5c) by replacing ethyl 5-(1-(5-fluoro-2-hydroxypyridin-3-yl)-2-azabicyclo[3.1.0]hexan-2-yl)pyrazolo[1,5-a]pyrimidine-3-carboxylate (5b) with ethyl 5-(1-(5-fluoro-2-hydroxyphenyl)-2-azabicyclo[3.1.0]hexan-2-yl)pyrazolo[1,5-a]pyrimidine-3-carboxylate (1b). MS-ESI (m/z): 515 [M+1]$^+$.

Ethyl 5-(1-(2-((R)-3-((tert-butoxycarbonyl)amino)but-1-yn-1-yl)-5-fluorophenyl)-2-azabicyclo[3.1.0]hexan-2-yl)pyrazolo[1,5-a]pyrimidine-3-carboxylate (12b-A and 12b-B)

To a solution of ethyl 5-(1-(5-fluoro-2-(((trifluoromethyl)sulfonyl)oxy)phenyl-3-yl)-2-azabicyclo[3.1.0]hexan-2-yl)pyrazolo[1,5-a]pyrimidine-3-carboxylate (12a) (84 mg, 0.16 mmol) and tert-butyl (R)-but-3-yn-2-ylcarbamate (5d) (110 mg, 0.650 mmol) in DMF (2.0 mL) was added Pd(PPh$_3$)$_2$C$_{1-2}$ (23.0 mg, 0.0327 mmol), CuI (6.2 mg, 0.033 mmol) and DIPEA (105 mg, 0.820 mmol). Then the resulting mixture was heated at 80° C. for 18 h at the atmosphere of N$_2$. The reaction was cooled to RT, quenched with water and extracted with EtOAc. The extracts were washed with water and brine, dried over Na$_2$SO$_4$, and concentrated. The residue was purified by preparative TLC to give the title compound ethyl 5-(1-(2-((R)-3-((tert-butoxycarbonyl)amino) but-1-yn-1-yl)-5-fluorophenyl)-2-azabicyclo[3.1.0]hexan-2-yl)pyrazolo-[1,5-a]pyrimidine-3-carboxylate (12b-A) (upper spot) and ethyl 5-(1-(2-((R)-3-((tert-butoxycarbonyl)amino)but-1-yn-1-yl)-5-fluorophenyl)-2-azabicyclo[3.1.0]hexan-2-yl) pyrazolo-[1,5-a]pyrimidine-3-carboxylate (12b-B) (lower spot). Both compounds shown MS-ESI (m/z): 534 [M+1]$^+$.

($1^3$E,$1^4$E,6R)-$3^5$-fluoro-6-methyl-$2^2$,7-diaza-1(5,3)-pyrazolo[1,5-a]pyrimidina-2(2,1)-bicyclo[3.1.0]hexana-3(1,2)-benzenacyclooctaphan-8-one (12A and 12B)

The title compound ($1^3$E, $1^4$E,6R)-$3^5$-fluoro-6-methyl-$2^2$,7-diaza-1(5,3)-pyrazolo[1,5-a]pyrimidina-2(2,1)-bicyclo[3.1.0]hexana-3(1,2)-benzenacyclooctaphan-8-one (12A and 12B) was prepared according to the synthetic method of 5 by replacing ethyl 5-(1-(2-((R)-3-((tert-butoxycarbonyl)amino)but-1-yn-1-yl)-5-fluoropyridin-3-yl)-2-azabicyclo[3.1.0]hexan-2-yl) pyrazolo[1,5-a]pyrimidine-3-carboxylate (5e) with ethyl 5-(1-(2-((R)-3-((tert-butoxycarbonyl)amino)but-1-yn-1-yl)-5-fluorophenyl)-2-azabicyclo[3.1.0]hexan-2-yl)pyrazolo-[1,5-a]pyrimidine-3-carboxylate (12b-A) or ethyl 5-(1-(2-((R)-3-((tert-butoxycarbonyl)amino)but-1-yn-1-yl)-5-fluorophenyl)-2-azabicyclo[3.1.0]hexan-2-yl)pyrazolo-[1,5-a]pyrimidine-3-carboxylate (12b-B). MS-ESI (m/z): 392 [M+1]$^+$.

Example 13

(6R,E)-$3^5$-fluoro-6-methyl-4-oxa-2,7-diaza-1(6,3)-imidazo[1,2-b]pyridazina-2(2,1)-bicyclo[3.1.0]hexana-3(1,2)-benzenacyclooctaphan-8-one (13)

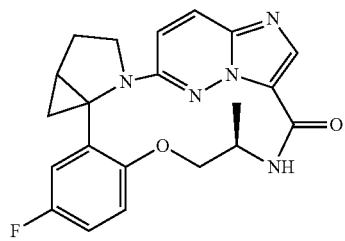

13

The title compound (6R,E)-$3^5$-fluoro-6-methyl-4-oxa-$2^2$,7-diaza-1(6,3)-imidazo[1,2-b]pyridazina-2(2,1)-bicyclo[3.1.0]hexana-3(1,2)-benzenacyclooctaphan-8-one (13) was prepared according to the synthetic method of example 1 by replacing ethyl 5-(1-(5-fluoro-2-hydroxyphenyl)-2-azabicyclo[3.1.0]hexan-2-yl)pyrazolo[1,5-a]pyrimidine-3-carboxylate (1b) with ethyl 6-(1-(5-fluoro-2-hydroxyphenyl)-2-azabicyclo[3.1.0]hexan-2-yl)imidazo[1,2-b]pyridazine-3-carboxylate (F). MS-ESI (m/z): 394 [M+1]$^+$.

Example 14

(6R,E)-3-fluoro-6-methyl-4-oxa-2,7-diaza-1(6,3)-imidazo[1,2-b]pyridazina-3(3,2)-pyridina-2(2,1)-bicyclo[3.1.0]hexanacyclooctphan-8-one (14]

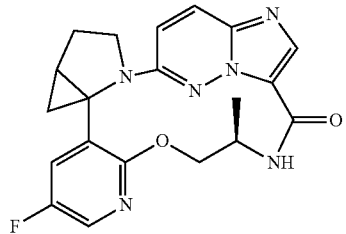

The title compound (6R,E)-3⁵-fluoro-6-methyl-4-oxa-2², 7-diaza-1(6,3)-imidazo[1,2-b]pyridazina-3(3,2)-pyridina-2(2,1)-bicyclo[3.1.0]hexanacyclotaphan-8-one (14) was prepared according to the synthetic method of example 1 by replacing ethyl 5-(1-(5-fluoro-2-hydroxyphenyl)-2-azabicyclo[3.1.0]hexan-2-yl)pyrazolo[1,5-a]pyrimidine-3-carboxylate (1b) with ethyl 6-(1-(5-fluoro-2-hydroxypyridin-3-yl)-2-azabicyclo[3.1.0]hexan-2-yl)imidazo[1,2-b]pyridazine-3-carboxylate (G). MS-ESI (m/z): 395 [M+1]⁺.

Example 15

(1³E,1⁴E,2¹R,2⁵S,6R)-3⁵-fluoro-6-methyl-4-oxa-2², 7-diaza-1(5,3)-pyrazolo[1,5-a]pyrimidina-2(2,1)-bicyclo[3.1.0]hexana-3(1,2)-benzenacyclooctaphan-8-one (15]

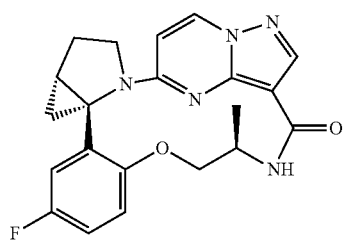

Ethyl 5-((1R,5S)-1-(2-((R)-2-((tert-butoxycarbonyl)amino)propoxy)-5-fluorophenyl)-2-azabicyclo[3.1.0]hexan-2-yl)pyrazolo[1,5-a]pyrimidine-3-carboxylate (15a)

To a solution of ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H) (120 mg, 0.320 mmol) in DMF (5 mL) was added $Cs_2CO_3$ (626 mg, 1.92 mmol), the mixture was stirred at 70° C. for 30 min. To the reaction mixture was added (R)-2-((tert-butoxycarbonyl)amino)propyl methanesulfonate (238 mg, 0.960 mmol) at 70° C. and stirred at 70° C. for overnight. The reaction mixture was cooled to RT, diluted with water and extracted with EtOAc. The extracts were washed with brine, dried over $Na_2SO_4$ and concentrated. The residue was purified by column chromatography on silica gel, eluting with PE/EtOAc (5:1~1:1) to give the title compound ethyl 5-((1R,5S)-1-(2-((R)-2-((tert-butoxycarbonyl)amino)propoxy)-5-fluorophenyl)-2-azabicyclo[3.1.0]hexan-2-yl)pyrazolo[1,5-a]pyrimidine-3-carboxylate (15a). MS-ESI (m/z): 540 [M+1]⁺.

5-((1R,5S)-1-(2-((R)-2-((tert-butoxycarbonyl)amino)propoxy)-5-fluorophenyl)-2-azabicyclo[3.1.0]hexan-2-yl)pyrazolo[1,5-a]pyrimidine-3-carboxylic acid (15b)

To a solution of ethyl 5-((1R,5S)-1-(2-((R)-2-((tert-butoxycarbonyl)amino)-propoxy)-5-fluorophenyl)-2-azabicyclo[3.1.0]hexan-2-yl)pyrazolo[1,5-a]pyrimidine-3-carboxylate (15a) (77.0 mg, 0.143 mmol) in MeOH (4 mL) was added a solution of LiOH (133 mg, 3.17 mmol) in $H_2O$ (0.7 mL) and stirred at 70° C. overnight and concentrated. The residue was adjusted PH=3~4 by 0.5 N HCl and extracted with EtOAc. The extracts were washed sequentially with $H_2O$ and brine, dried over $Na_2SO_4$ and concentrated to give 5-((1R,5S)-1-(2-((R)-2-((tert-butoxycarbonyl)-amino)propoxy)-5-fluorophenyl)-2-azabicyclo[3.1.0]hexan-2-yl)pyrazolo[1,5-a]pyrimidine-3-carboxylic acid (15b), which was used for next step directly. MS-ESI (m/z): 512 [M+1]⁺.

(R)-1-(2-((1R,5S)-2-(3-carboxypyrazolo[1,5-a]pyrimidin-5-yl)-2-azabicyclo[3.1.0]Hexan-1-yl)-4-fluorophenoxy)propan-2-aminium 2,2,2-trifluoroacetate (15c)

To a solution of 5-((1R,5S)-1-(2-((R)-2-((tert-butoxycarbonyl)amino)propoxy)-5-fluorophenyl)-2-azabicyclo[3.1.0]hexan-2-yl)pyrazolo[1,5-a]pyrimidine-3-carboxylic acid (15b) (72 mg, 0.14 mmol) in DCM (5 mL) was added TFA (4 mL) at 0° C. Then the mixture was warmed to r.t. and stirred for 40 min. The reaction mixture was evaporated to give the crude product of (R)-1-(2-((1R,5S)-2-(3-carboxypyrazolo[1,5-a]pyrimidin-5-yl)-2-azabicyclo[3.1.0]hexan-1-yl)-4-fluorophenoxy)propan-2-aminium 2,2,2-trifluoroacetate (15c), which was used for next step directly. MS-ESI (m/z): 412 [M+1]⁺.

(1³E,1⁴E,2¹R,2⁵S,6R)-3⁵-fluoro-6-methyl-4-oxa-2², 7-diaza-1(5,3)-pyrazolo[1,5-a]pyrimidina-2(2,1)-bicyclo[3.1.0]hexana-3(1,2)-benzenacyclooctaphan-8-one (15)

A mixture of (R)-1-(2-((1R,5S)-2-(3-carboxypyrazolo[1, 5-a]pyrimidin-5-yl)-2-azabicyclo[3.1.0]hexan-1-yl)-4-fluorophenoxy)propan-2-aminium 2,2,2-trifluoroacetate (15c) (194 mg, 0.143 mmol), FDPP (55.0 mg, 0.143 mmol) and DIPEA (0.300 mL, 1.82 mmol) in DMF (40 mL) was stirred at RT for overnight. The mixture was diluted with water and extracted with EtOAc. The extracts were washed with brine, dried over $Na_2SO_4$ and concentrated. The residue was purified by preparative TLC to give the title compound (1³E, 1⁴E,2¹R,2⁵S,6R)-3⁵-fluoro-6-methyl-4-oxa-2²,7-diaza-1(5, 3)-pyrazolo[1,5-a]pyrimidina-2(2,1)-bicyclo[3.1.0]hexana-3(1,2)-benzenacyclooctaphan-8-one (15). ¹H NMR (600 MHz, $CDCl_3$): δ 9.87 (d, 1H), 8.27-8.26 (m, 2H), 7.14 (dd, 1H), 6.87-6.85 (m, 1H), 6.72 (dd, 1H), 6.20 (d, 1H), 4.54 (brs, 1H), 4.41 (q, 1H), 4.24 (d, 1H), 4.06 (dd, 1H), 3.73-3.69 (m, 1H), 2.66-2.60 (m, 1H), 2.31 (t, 1H), 2.14-

2.10 (m, 1H), 1.74-1.70 (m, 1H), 1.47 (d, 3H), 1.33 (t, 1H).MS-ESI (m/z): 394 [M+1]+.

Example 16

(1³E,1⁴E,2¹R,2⁵S)-3⁵-fluoro-4-oxa-2²,7-diaza-1(5,3)-pyrazolo[1,5-a]pyrimidina-2(2,1)-bicyclo[3.1.0]Hexana-3(1,2)-benzeneacyclooctaphan-8-one (16)

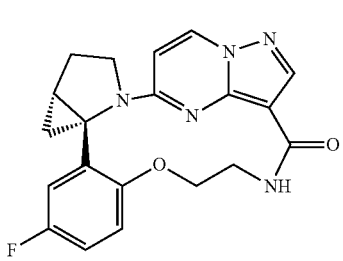

The title compound 16 was prepared according to the syndetic method of 15 by replacing (R)-2-((tert-butoxycarbonyl)amino)propyl methanesulfonate with 2-((tert-butoxycarbonyl)amino)ethyl methanesulfonate. ¹H NMR (600 MHZ, CDCl₃): δ 9.59 (s, 1H), 8.27-8.26 (m, 2H), 7.14 (dd, 1H), 6.86 (dt, 1H), 6.77 (dd, 1H), 6.21 (d, 1H), 4.45-4.41 (m, 1H), 4.37-4.34 (m, 1H), 4.18-4.16 (m, 1H), 4.08-4.06 (m, 1H), 3.67-3.64 (m, 1H), 3.58-3.53 (m, 1H), 2.66-2.60 (m, 1H), 2.28-2.26 (m, 1H), 2.17-2.13 (m, 1H), 1.71-1.67 (m, 1H), 1.26 (t, 1H). MS-ESI (m/z): 380 [M+1]+.

Example 17

(3'E,4'E)-5'-fluoro-2'-methyldispiro[cyclopropane-1,3'-5-oxa-2,8-diaza-1(5,3)-pyrazolo[1,5-a]pyrimidina-4(3,2)-pyridinacyclononaphane-7',1'''-cyclopropan]-9'-one (17)

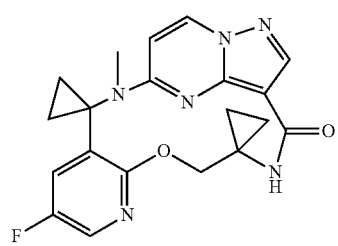

The title compound 17 was prepared according to the synthetic method of 15 by replacing ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H) and (R)-2-((tert-butoxycarbonyl)amino)propyl methanesulfonate with ethyl 5-((1-(5-fluoro-2-hydroxypyridin-3-yl)cyclopropyl)(methyl)amino) pyrazolo[1,5-a]pyrimidine-3-carboxylate (J) and (1-((tert-butoxycarbonyl)amino)cyclopropyl) methyl methanesulfonate. ¹H NMR (600 MHz, CDCl₃): δ 9.30 (s, 1H), 8.29 (d, 1H), 8.27 (s, 1H), 7.87 (d, 1H), 7.61 (dd, 1H) 6.26 (d, 1H), 4.85 (d, 1H), 3.56 (d, 1H), 3.48 (s, 3H), 2.61-2.57 (m, 1H), 2.39-2.35 (m, 1H), 1.47-1.40 (m, 2H), 1.03-1.00 (m, 2H), 0.93-0.92 (m, 1H), 0.77-0.73 (m, 1H). MS-ESI (m/z): 395 [M+1]+.

Example 18

(2¹R,2⁵S,6R,E)-3-fluoro-6-methyl-4-oxa-2²,7-diaza-1(6,3j-imidazo[1,2-b]pyridazina-3(3,2)-pyridina-2(2,1)-bicyclo[3.1.0]hexanacyclooctaphan-8-one (18)

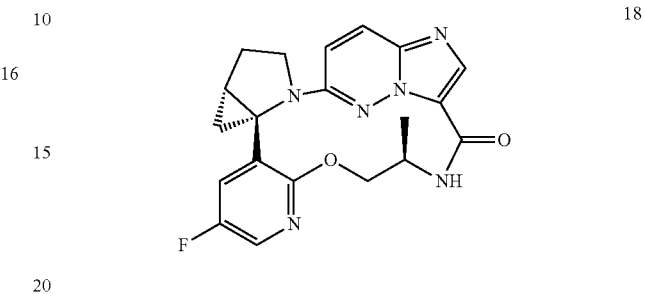

The title compound 18 was prepared according to the synthetic method of 15 by replacing 2-(5-fluoro-2-methoxyphenyl)acetonitrile (H-1) and ethyl 5-chloropyrazolo[1,5-a]pyrimidine-3-carboxylate (1a) with 2-(5-fluoro-2-methoxypyridin-3-yl)acetonitrile (D-5) and ethyl 6-chloroimidazo[1,2-b]pyridazine-3-carboxylate (F-1). ¹H NMR (600 MHz, CDCl₃): δ 9.96 (d, 1H), 8.18 (s, 1H), 7.87 (d, 1H), 7.79 (d, 1H), 7.61 (dd, 1H), 6.75 (d, 1H), 4.96 (dd, 1H), 4.65-4.62 (m, 1H), 4.37-4.33 (m, 1H), 4.14 (d, 1H), 3.40 (q, 1H), 2.67-2.61 (m, 1H), 2.30 (t, 1H), 2.26-2.23 (m, 1H), 1.73-1.71 (m, 1H), 1.50 (d, 3H), 1.38 (t, 1H). MS-ESI (m/z): 395 [M+1]+.

Example 19

(1³E,1⁴E,2¹R,2⁵S,6R)-3⁵-fluoro-6-methyl-4-oxa-2²,7-diaza-1(5,3)pyrazolo[1,5-a]pyrimidina-3(3,2)-pyridina-2(2,1)-bicyclo[3.1.0]hexanacyclooctaphan-8-one (19)

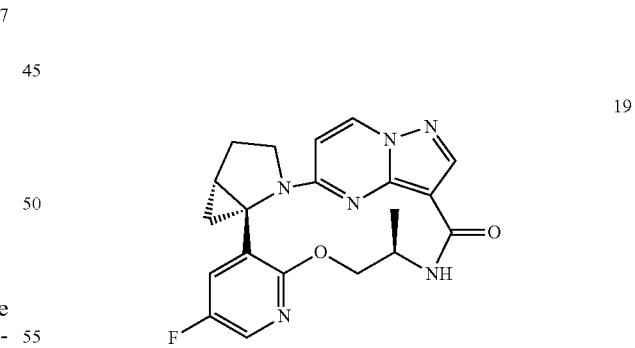

The title compound 19 was prepared according to the synthetic method of 15 by replacing 2-(5-fluoro-2-methoxyphenyl)acetonitrile (H-1) with 2-(5-fluoro-2-methoxypyridin-3-yl)acetonitrile (D-5). ¹H NMR (600 MHz, CDCl₃): δ 9.47 (d, 1H), 8.28-8.27 (m, 2H), 7.86 (d, 1H), 7.49 (dd, 1H), 6.21 (d, 1H), 4.95 (dd, 1H), 4.51-4.50 (m, 1H), 4.38-4.33 (m, 1H), 4.07 (dd, 1H), 3.65-3.61 (m, 1H), 2.69-2.63 (m, 1H), 2.27 (t, 1H), 2.22-2.17 (m, 1H), 1.78-1.74 (m, 1H), 1.47 (d, 3H), 1.32 (t, 1H). MS-ESI (m/z): 395 [M+1]+.

Example 20

(1³E,1⁴E,2¹R,2⁵S,6R)-3⁵-fluoro-6-methyl-2²,7-diaza-1(5,3)-pyrazolo[1,5-a]pyrimidina-3(3,2)-pyridina-2(2,1)-bicyclo[3.1.0]hexanacyclooctaphan-8-one (20)

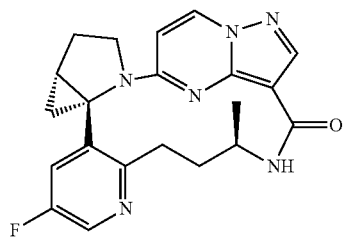

The title compound 20 was prepared according to the synthetic method of 10 by replacing ethyl 5-((1-(5-fluoro-2-hydroxypyridin-3-yl)cyclopropyl)amino)pyrazolo[1,5-a]pyrimidine-3-carboxylate (D) with ethyl 5-((1R,5S)-1-(5-fluoro-2-hydroxypyridin-3-yl)-2-azabicyclo[3.1.0]hexan-2-yl)pyrazolo[1,5-a]pyrimidine-3-carboxylate (I). ¹H NMR (600 MHz, CDCl₃): δ 8.29 (d, 1H), 8.26 (d, 1H), 8.24 (s, 1H), 8.06 (d, 1H), 7.37 (dd, 1H), 6.24 (d, 1H), 4.35-4.31 (m, 1H), 4.29-4.26 (m, 1H), 3.72-3.67 (m, 1H), 3.57 (q, 1H), 2.81-2.77 (m, 2H), 2.68-2.63 (m, 1H), 2.33-2.29 (m, 1H), 2.06-2.01 (m, 2H), 1.68-1.67 (m, 1H), 1.49 (t, 1H), 1.40 (d, 3H). MS-ESI (m/z): 393 [M+1]⁺.

Example 21

(1³E,1⁴E,2¹R,2⁵S,5R)-3³-fluoro-5-methyl-4-oxa-2², 7-diaza-1(5,3)-pyrazolo[1,5-a]pyrimidina-2(2,1)-bicyclo[3.1.0]hexana-3(1,2)-benzenacyclooctaphan-8-one (21)

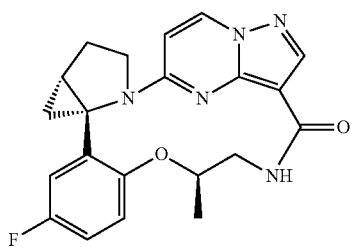

Ethyl 5-((1 R,5S)-1-(2-(((R)-1-((tert-butoxycarbonyl)amino)propan-2-yl)oxy)-5-fluorophenyl)-2-azabicyclo[3.1.0]hexan-2-yl)pyrazolo[1,5-a]pyrimidine-3-carboxylate 121a)

To a solution of ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H) (1.50 g, 3.93 mmol) and tert-butyl (5)-(2-hydroxypropyl)carbamate (1.03 g, 5.90 mmol) in THF (66 mL) was added PPh₃ (1.55 g, 5.90 mmol) at r.t. under N₂ atmosphere. Then DIAD (1.27 g, 5.90 mmol) was added dropwise. The mixture was stirred at 30° C. for overnight. The reaction mixture was concentrated and redisolved in EtOAc. The solution was washed with brine, dried over Na₂SO₄ and concentrated. The residue was purified by flash column chromatography on silica gel, eluting with DCM/MeOH (200:1~100:1) to give the title compound ethyl 5-((1R,5S)-1-(2-(((R)-1-((tert-butoxycarbonyl)-amino)propan-2-yl)oxy)-5-fluorophenyl)-2-azabicyclo[3.1.0]hexan-2-yl)pyrazolo[1,5-a]pyrimidine-3-carboxylate (21a). MS-ESI (m/z): 540 [M+1]⁺.

(1³E,1⁴E,2¹R,2⁵S,5R)-3⁵-fluoro-5-methyl-4-oxa-2², 7-diaza-1(5,3)-pyrazolo[1,5-a]pyrimidina-2(2,1)-bicyclo[3.1.0]hexana-3(1,2)-benzenacyclooctaphan-8-one (21)

The title compound 21 was prepared according to the synthetic method of 15 by replacing ethyl 5-((1R,5S)-1-(2-((R)-2-((tert-butoxycarbonyl)amino)propoxy)-5-fluorophenyl)-2-azabicyclo[3.1.0]hexan-2-yl)pyrazolo[1,5-a]pyrimidine-3-carboxylate (15a) with ethyl 5-((1R,5S)-1-(2-(((R)-1-((tert-butoxycarbonyl)amino)propan-2-yl)oxy)-5-fluorophenyl)-2-azabicyclo[3.1.0]hexan-2-yl)pyrazolo[1,5-a]pyrimidine-3-carboxylate (21a). ¹H NMR (600 MHz, CDCl₃): δ 9.23 (s, 1H), 8.29-8.28 (m, 2H), 7.13 (dd, 1H), 6.90-6.87 (m, 1H), 6.80-6.79 (m, 1H), 6.23 (d, 1H), 4.73-4.72 (m, 1H), 4.31-4.27 (m, 1H), 3.87-3.80 (m, 2H), 3.59-3.55 (m, 1H), 2.62-2.61 (m, 1H), 2.30-2.28 (m, 1H), 2.20-2.17 (m, 1H), 1.70-1.68 (m, 1H), 1.56 (d, 3H), 1.22 (t, 1H). MS-ESI (m/z): 394 [M+1]⁺.

Example 22

(1³E,1⁴E,2¹R,2⁵S,5S)-3⁵-fluoro-5-methyl-4-oxa-2², 7-diaza-1(5,3)-pyrazolo[1,5-a]pyrimidina-2(2,1)-bicyclo[3.1.10]hexana-3(1,2)-benzenacyclooctaphan-8-one (22)

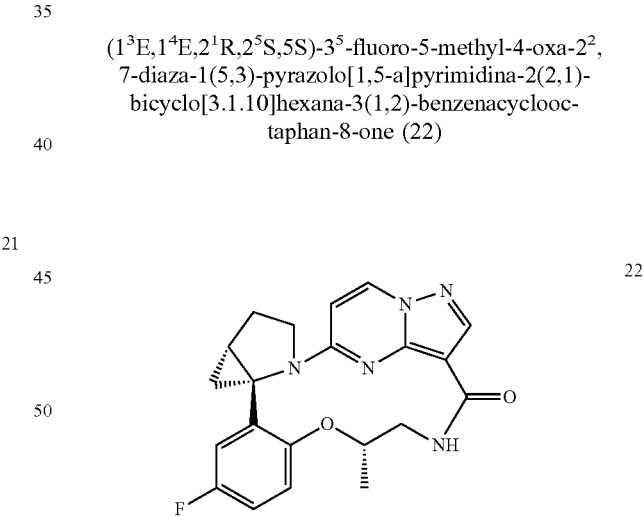

The title compound 22 was prepared according to the synthetic method of 21 by replacing tert-butyl (5)-(2-hydroxypropyl)carbamate with tert-butyl (R)-(2-hydroxypropyl)-carbamate. ¹H NMR (600 MHz, CDCl₃): δ 9.67 (s, 1H), 8.28-8.26 (m, 2H), 7.13 (dd, 1H), 6.86-6.83 (m, 1H), 6.80-6.78 (m, 1H), 6.21 (d, 1H), 4.56-4.53 (m, 1H), 4.36-4.33 (m, 1H), 4.10-4.06 (m, 1H), 3.64-3.60 (m, 1H), 3.31-3.27 (m, 1H), 2.67-2.61 (m, 1H), 2.32-2.29 (m, 1H), 2.20-2.15 (m, 1H), 1.71-1.67 (m, 1H), 1.49 (d, 3H), 1.23 (t, 1H). MS-ESI (m/z): 394 [M+1]⁺.

Example 23

(1³E,1⁴E,2¹R,2⁵S)-3⁵-fluoro-4-oxa-2²,7-diaza-1(5, 3)-pyrazolo[1,5-a]pyrimidina-3(3,2)-pyridina-2(2,1)-bicyclo[3.1.0]hexanacyclooctaphan-8-one (23)

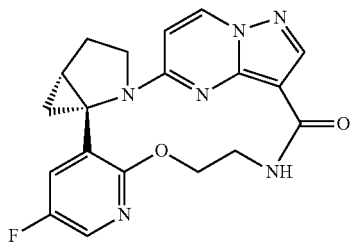

The title compound 23 was prepared according to the synthetic method of 15 by replacing ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H) and (R)-2-((tert-butoxycarbonyl)amino)propyl methanesulfonate with ethyl 5-((1R,5S)-1-(5-fluoro-2-hydroxypyridin-3-yl)-2-azabicyclo[3.1.0]-hexan-2-yl)pyrazolo[1,5-a]pyrimidine-3-carboxylate (I) and 2-((tert-butoxycarbonyl)amino)ethyl methanesulfonate. ¹H NMR (600 MHz, CDCl₃): δ 9.19 (brs, 1H), 8.29-8.28 (m, 2H), 7.87 (d, 1H), 7.50 (dd, 1H), 6.22 (d, 1H), 5.01-4.98 (m, 1H), 4.34-4.30 (m, 2H), 4.05-4.01 (m, 1H), 3.65-3.55 (m, 2H), 2.69-2.63 (m, 1H), 2.26-2.20 (m, 2H), 1.76-1.72 (m, 1H), 1.27 (t, 1H). MS-ESI (m/z): 381 [M+1]⁺.

Example 24

(1³E,1⁴E,2¹R,2⁵S,6S)-3⁵-fluoro-6-methyl-4-oxa-2², 7-diaza-1(5,3)-pyrazolo[1,5-a]pyrimidina-2(2,1)-bicyclo[3.1.0]hexana-3(1,2)-benzenacyclooctaphan-8-one (24)

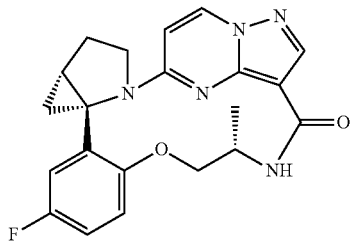

The title compound 24 was prepared according to the synthetic method of 15 by replacing (R)-2-((tert-butoxycarbonyl)amino)propyl methanesulfonate with (S)-2-((tert-butoxycarbonyl)amino)propyl methanesulfonate. ¹H NMR (600 MHZ, CDCl₃): δ 9.40 (s, 1H), 8.28-8.26 (m, 2H), 7.16 (dd, 1H), 6.88-6.85 (m, 2H), 6.20 (d, 1H), 4.39-4.31 (m, 2H), 4.18-4.16 (m, 1H), 4.09-4.06 (m, 1H), 3.69-3.66 (m, 1H), 2.63-2.58 (m, 1H), 2.21 (t, 1H), 2.11-2.07 (m, 1H), 1.68-1.63 (m, 4H), 1.20 (t, 1H). MS-ESI (m/z): 394 [M+1]⁺.

Example 25

(1³E,1⁴E,2¹R,2⁵S,5R)-3⁵-fluoro-5-methyl-4-oxa-2²,7-diaza-1(5,3)-pyrazolo[1,5-a]pyrimidina-(3,2)-pyridina-2(2,1)-bicyclo[3.1.0]hexanacyclooctaphan-8-one (25)

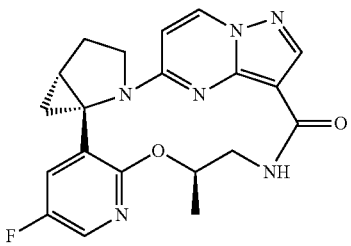

The title compound 25 was prepared according to the synthetic method of 21 by replacing ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H) with ethyl 5-((1R,5S)-1-(5-fluoro-2-hydroxypyridin-3-yl)-2-azabicyclo[3.1.0]hexan-2-yl)pyrazolo[1,5-a]pyrimidine-3-carboxylate (I). ¹H NMR (600 MHz, CDCl₃): δ 8.84 (d, 1H), 8.30-8.28 (m, 2H), 7.80 (d, 1H), 7.44 (dd, 1H), 6.22 (d, 1H), 4.71-4.70 (m, 1H), 4.26-4.22 (m, 1H), 4.01 (t, 1H), 3.90-3.86 (m, 1H), 3.49-3.44 (m, 1H), 2.67-2.65 (m, 1H), 2.29-2.26 (m, 1H), 2.21-2.19 (m, 1H), 1.82 (d, 3H), 1.74-1.71 (m, 1H), 1.21 (t, 1H). MS-ESI (m/z): 395 [M+1]⁺.

Example 26

(1³E,1⁴E,2¹R,2⁵S,5S)-3⁵-fluoro-5-methyl-4-oxa-2², 7-diaza-1(5,3)-pyrazolo[1,5-a]pyrimidina-3(3,2)-pyridina-2(2,1)-bicyclo[3.1.0]hexanacyclooctaphan-8-one (26)

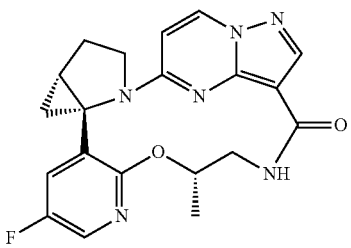

The title compound 26 was prepared according to the synthetic method of 21 by replacing ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H) and tert-butyl (S)-(2-hydroxypropyl)carbamate with ethyl 5-((1R,5S)-1-(5-fluoro-2-hydroxypyridin-3-yl)-2-azabicyclo[3.1.0]hexan-2-yl)pyrazolo[1,5-a]pyrimidine-3-carboxylate (I) and tert-butyl (R)-(2-hydroxypropyl)carbamate. ¹H NMR (600 MHz, CDCl₃): δ 9.38 (d, 1H), 8.28-8.27 (m, 2H), 7.85 (d, 1H), 7.48 (dd, 1H), 6.21 (d, 1H), 5.32-5.28 (m, 1H), 4.36-4.32 (m, 1H), 4.15-4.11 (m, 1H), 3.61-3.57 (m, 1H), 3.29-3.26 (m, 1H), 2.69-2.63 (m, 1H), 2.26-2.19 (m, 2H), 1.75-1.71 (m, 1H), 1.48 (d, 3H), 1.25 (t, 1H). MS-ESI (m/z): 395 [M+1]⁺.

Example 27

(1³E,1⁴E,2¹R,2⁵S,6R)-3⁵-fluoro-6-methyl-2²,7-diaza-1(5,3)-pyrazolo[1,5-a]pyrimidina-2(2,1)-bicyclo[3.1.0]hexana-3(1,2)-benzeneacyclooctaphan-8-one (27)

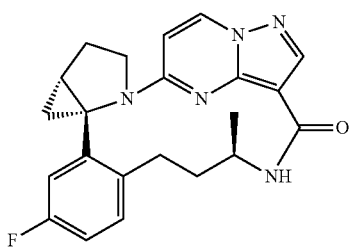

The title compound 27 was prepared according to the synthetic method of 10 by replacing ethyl 5-((1-(5-fluoro-2-hydroxypyridin-3-yl)cyclopropyl) amino)pyrazolo[1,5-a]pyrimidine-3-carboxylate (D) with ethyl 5-((1R,5S)-1-(5-fluoro-2-hydroxyphenyl)-2-azabicyclo[3.1.0]hexan-2-yl)pyrazolo[1,5-a]pyrimidine-3-carboxylate (H). $^1$H NMR (600 MHz, CDCl$_3$): δ 8.26-8.24 (m, 3H), 7.18 (t, 1H), 7.05 (dd, 1H), 6.88 (dt, 1H), 6.23 (d, 1H), 4.38-4.34 (m, 1H), 4.26-4.22 (m, 1H), 3.67-3.59 (m, 2H), 2.75-2.71 (m, 1H), 2.70-2.63 (m, 1H), 2.24-2.19 (m, 3H), 1.98-1.96 (m, 1H), 1.65-1.62 (m, 1H), 1.45-1.43 (m, 4H). MS-ESI (m/z): 392 [M+1]⁺.

Example 28

(1³E,1⁴E,2¹R,2⁵S,6S)-3⁵-fluoro-6-methyl-4-oxa-2²,7-diaza-1(5,3)-pyrazolo[1,5-a]pyrimidina-3(3,2)-pyridina-2(2,1)-bicyclo[3.1.0]hexanacyclooctaphan-8-one (28)

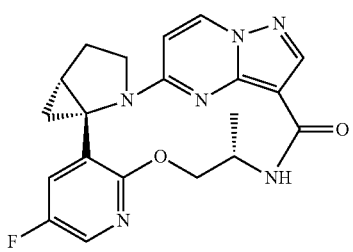

The title compound 28 was prepared according to the synthetic method of 15 by replacing ethyl 5-((1R,5S)-1-(5-fluoro-2-hydroxyphenyl)-2-azabicyclo[3.1.0]hexan-2-yl) pyrazolo[1,5-a]pyrimidine-3-carboxylate (H) and (R)-2-((tert-butoxycarbonyl)amino)propyl methanesulfonate with ethyl 5-((1R,5S)-1-(5-fluoro-2-hydroxypyridin-3-yl)-2-azabicyclo[3.1.0]-hexan-2-yl)pyrazolo[1,5-a]pyrimidine-3-carboxylate (I) and (S)-2-((tert-butoxycarbonyl)amino)propyl methanesulfonate. $^1$H NMR (600 MHz, CDCl$_3$): δ 9.09 (brs, 1H), 8.30-8.28 (m, 2H), 7.89 (d, 1H), 7.52 (dd, 1H), 6.21 (d, 1H), 5.08 (dd, 1H), 4.36-4.33 (m, 1H), 4.29-4.27 (m, 1H), 4.26-4.19 (m, 1H), 3.61-3.56 (m, 1H), 2.68-2.62 (m, 1H), 2.22-2.14 (m, 2H), 1.74-1.70 (m, 1H), 1.57 (d, 3H), 1.21 (t, 1H). MS-ESI (m/z): 395 [M+1]⁺.

Example 29

(2¹R,2⁵S,6R,E)-3⁵-fluoro-6-methyl-2²,7-diaza-1(6,3)-imidazo[1,2-b]pyridazina-3(3,2)-pyridina-2(2,1)-bicyclo[3.1.0]hexanacyclooctaphan-8-one (29)

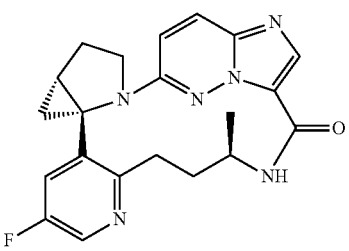

The title compound 29 was prepared according to the synthetic method of 10 by replacing ethyl 5-((1-(5-fluoro-2-hydroxypyridin-3-yl)cyclopropyl) amino)pyrazolo[1,5-a]pyrimidine-3-carboxylate (D) with ethyl 5-((1R,5S)-1-(5-fluoro-2-hydroxypyridin-3-yl)-2-azabicyclo[3.1.0]hexan-2-yl)pyrazolo[1,5-a]pyrimidine-3-carboxylate (I). $^1$H NMR (600 MHZ, CDCl$_3$): δ 8.65 (d, 1H), 8.30 (d, 1H), 8.13 (s, 1H), 7.77 (d, 1H), 7.49 (dd, 1H), 6.78 (d, 1H), 4.45-4.43 (m, 1H), 4.36-4.32 (m, 1H), 3.62-3.58 (m, 1H), 3.42 (q, 1H), 2.87-2.77 (m, 2H), 2.63-2.60 (m, 1H), 2.33-2.30 (m, 1H), 2.10-2.03 (m, 2H), 1.66-1.64 (m, 1H), 1.54 (t, 1H), 1.38 (d, 3H). MS-ESI (m/z): 393 [M+1]⁺.

Following essentially the same procedures described for Examples 1-29, Examples 30-100 listed in Table 1 were prepared from the appropriate starting materials which are commercially available or known in the literature. The structures and names of Examples 30-100 are given in Table 1.

TABLE 1

| EXAMPLE | STRUCTURE | NAME | DATA |
| --- | --- | --- | --- |
| 30 | 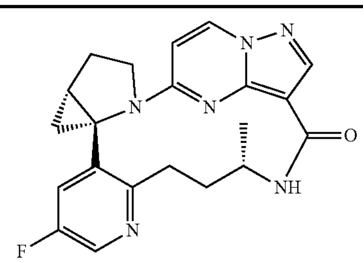 | (1³E,1⁴E,2¹R,2⁵S,6S)-35-fluoro-6-methyl-2²,7-diaza-1(5,3)-pyrazolo[1,5-a]pyrimidina-3(3,2)-pyridina-2(2,1)-bicyclo[3.1.0]hexana-cyclooctaphan-8-one | MS-ESI (m/z): 393 [M + 1]⁺ |

TABLE 1-continued

| EXAMPLE | STRUCTURE | NAME | DATA |
|---|---|---|---|
| 31 | 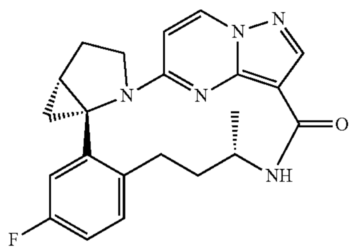 [SMILES: C[C@H]1CCc2ccc(F)cc2[C@@]23C[C@@H]2CCN3c2ccn3ncc(c3n2)C(=O)N1] | ($1^3$E,$1^4$E,$2^1$R,$2^5$S,6S)-$3^5$-fluoro-6-methyl-$2^2$,7-diaza-1(5,3)-pyrazolo[1,5-a]pyrimidina-2(2,1)-bicyclo[3.1.0]hexana-3(1,2)-benzenecyclooctaphan-8-one | MS-ESI (m/z): 392 [M + 1]$^+$ |
| 32 | 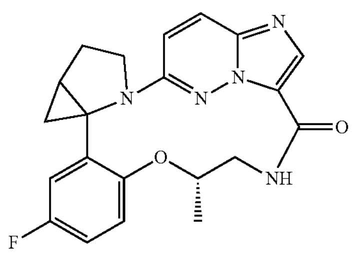 [SMILES: C[C@H]1CNC(=O)c2cnc3ccc(nn23)N2CCC3CC32c2cc(F)ccc2O1] | (5S,E)-$3^5$-fluoro-5-methyl-4-oxa-$2^2$,7-diaza-1(6,3)-imidazo[1,2-b]pyridazina-2(2,1)-bicyclo[3.1.0]hexana-3(1,2)-benzenacyclooctaphan-8-one | MS-ES (m/z): 394 [M + 1]$^+$ |
| 33A/33B | 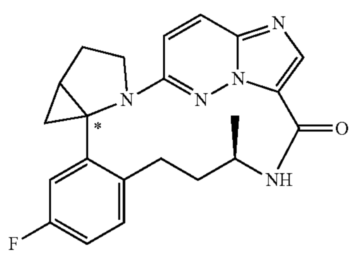 [SMILES: C[C@@H]1CCc2ccc(F)cc2C23CC2CCN3c2ccc3ncc(n3n2)C(=O)N1] | (6R,E)-$3^5$-fluoro-6-methyl-$2^2$,7-diaza-1(6,3)-imidazo[1,2-b]pyridazina-2(2,1)-bicyclo[3.1.0]hexana-3(1,2)-benzena-cyclooctaphan-8-one | MS-ESI (m/z): 392 [M + 1]$^+$ |
| 34 | 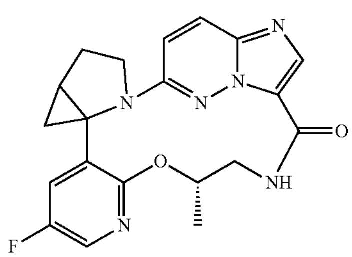 [SMILES: C[C@H]1CNC(=O)c2cnc3ccc(nn23)N2CCC3CC32c2cc(F)cnc2O1] | (5S,E)-$3^5$-fluoro-5-methyl-4-oxa-$2^2$,7-diaza-1(6,3)-imidazo[1,2-b]pyridazina-3(3,2)-pyridina-2(2,1)-bicyclo[3.1.0]-hexanacyclooctaphan-8-one | MS-ESI (m/z): 395 [M + 1]$^+$ |
| 35 | 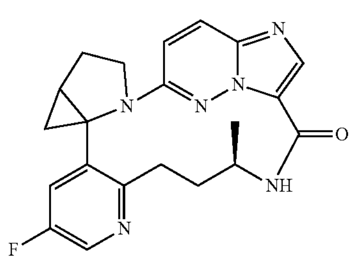 [SMILES: C[C@@H]1CCc2ncc(F)cc2C23CC2CCN3c2ccc3ncc(n3n2)C(=O)N1] | (6R,E)-$3^5$-fluoro-6-methyl-$2^2$,7-diaza-1(6,3)-imidazo[1,2-b]pyridazina-3(3,2)-pyridina-2(2,1)-bicyclo[3.1.0]hexanacyclooctaphan-8-one | MS-ESI (m/z): 393 [M + 1]$^+$ |
| 36 | 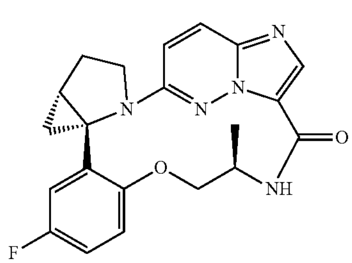 [SMILES: C[C@@H]1COc2ccc(F)cc2[C@@]23C[C@@H]2CCN3c2ccc3ncc(n3n2)C(=O)N1] | ($2^1$R,$2^5$S,6R,E)-$3^5$-fluoro-6-methyl-4-oxa-$2^2$,7-diaza-1(6,3)-imidazo[1,2-b]pyridazina-2(2,1)-bicyclo[3.1.0]hexana-3(1,2)-benzenacyclooctaphan-8-one | MS-ESI (m/z): 394 [M + 1]$^+$ |

TABLE 1-continued

| EXAMPLE | STRUCTURE | NAME | DATA |
|---|---|---|---|
| 37 | 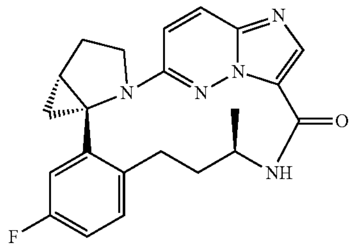 [SMILES: C[C@@H]1CCc2ccc(F)cc2[C@@]23C[C@@H]2CCN3c2ccc3ncc(n3n2)C(=O)N1] | (2$^1$R,2$^5$S,6R,E)-3$^5$-fluoro-6-methyl-2$^2$,7-diaza-1(6,3)-imidazo[1,2-b]pyridazina-2(2,1)-bicyclo[3.1.0]hexana-3(1,2)-benzena-cyclooctaphan-8-one | MS-ESI (m/z): 392 [M + 1]$^+$ |
| 38 | 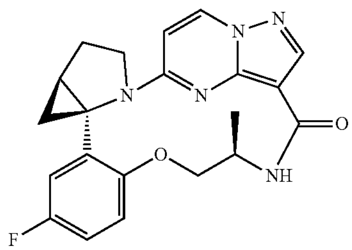 [SMILES: C[C@@H]1COc2ccc(F)cc2[C@]23C[C@H]2CCN3c2ccn3ncc(c3n2)C(=O)N1] | (1$^3$E,1$^4$E,2$^1$R,2$^5$S,6R)-3$^5$-fluoro-6-methyl-4-oxa-2$^4$,7-diaza-1(5,3)-pyrazolo[1,5-a]pyrimidina-2(4,5)-bicyclo[3.1.0]hexana-3(1,2)-benzenacyclooctaphan-8-one | MS-ESI (m/z): 394 [M + 1]$^+$ |
| 39 | 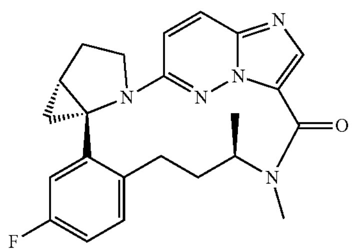 [SMILES: C[C@@H]1CCc2ccc(F)cc2[C@@]23C[C@@H]2CCN3c2ccc3ncc(n3n2)C(=O)N1C] | (1$^3$E,1$^4$E,2$^1$R,2$^5$S,6R)-3$^5$-fluoro-6,7-dimethyl-4-oxa-2$^2$,7-diaza-1(5,3)-pyrazolo[1,5-a]pyrimidina-2(2,1)-bicyclo[3.1.0]hexana-3(1,2)-benzenacyclooctaphan-8-one | MS-ESI (m/z): 408 [M + 1]$^+$ |
| 40 | 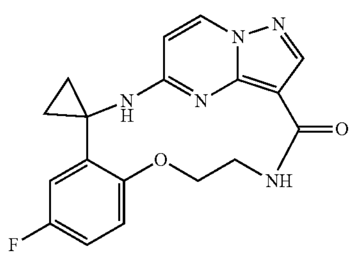 [SMILES: O=C1NCCOc2ccc(F)cc2C2(CC2)Nc2ccn3ncc1c3n2] | (3'E,4'E)-5'-fluorospiro[cyclopropane-1,3'-5-oxa-2,8-diaza-1(5,3)-pyrazolo[1,5-a]pyrimidina-4(1,2)-benzena-cyclononaphan]-9'-one | MS-ESI (m/z): 354 [M + 1]$^+$ |
| 41 | 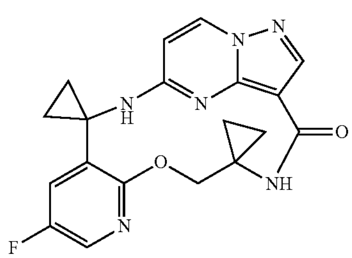 [SMILES: O=C1NC2(CC2)COc2ncc(F)cc2C2(CC2)Nc2ccn3ncc1c3n2] | (3'E,4'E)-5'-fluorodispiro[cyclopropane-1,3'-5-oxa-2,8-diaza-1(5,3)-pyrazolo[1,5-a]pyrimidina-4(3,2)-pyridina-cyclononaphane-7',1''-cyclopropan]-9'-one | MS-ESI (m/z): 381 [M + 1]$^+$ |
| 42 | 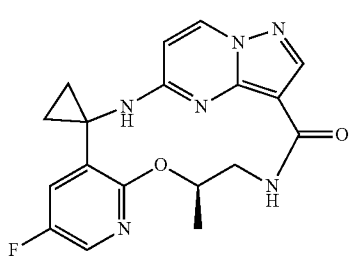 [SMILES: C[C@@H]1CNC(=O)c2cnn3ccc(nc23)NC2(CC2)c2cc(F)cnc2O1] | (R,3'E,4'E)-5'-fluoro-6'-methylspiro[cyclopropane-1,3'-5-oxa-2,8-diaza-1(5,3)-pyrazolo[1,5-a]pyrimidina-4(3,2)-pyridina-cyclononaphan]-9'-one | MS-ESI (m/z): 369 [M + 1]$^+$ |

TABLE 1-continued

| EXAMPLE | STRUCTURE | NAME | DATA |
|---|---|---|---|
| 43 | 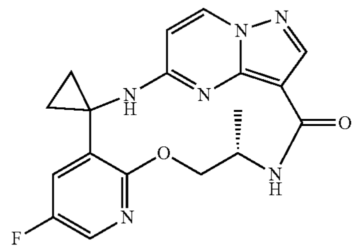 [SMILES: C[C@H]1COc2ncc(F)cc2C2(CC2)Nc2ccn3ncc(c3n2)C(=O)N1] | (S,3'E,4'E)-5'-fluoro-7'-methylspiro-[cyclopropane-1,3'-5-oxa-2,8-diaza-1(5,3)-pyrazolo[1,5-a]pyrimidina-4(3,2)-pyridina-cyclononaphan]-9'-one | MS-ESI (m/z): 369 [M + 1]⁺ |
| 44 | 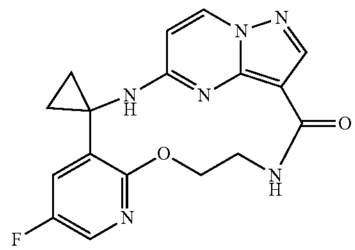 [SMILES: O=C1NCCOc2ncc(F)cc2C2(CC2)Nc2ccn3ncc1c3n2] | (3'E,4'E)-5'-fluorospiro[cyclopropane-1,3'-5-oxa-2,8-diaza-1(5,3)-pyrazolo[1,5-a]pyrimidina-4(3,2)-pyridinacyclononaphan]-9'-one | MS-ESI (m/z): 355 [M + 1]⁺ |
| 45 | 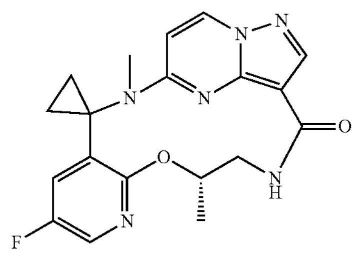 [SMILES: C[C@H]1CNC(=O)c2cnn3ccc(nc23)N(C)C2(CC2)c2cc(F)cnc2O1] | (S,3'E,4'E)-5'-fluoro-2',6'-dimethylspiro-[cyclopropane-1,3'-5-oxa-2,8-diaza-1(5,3)-pyrazolo[1,5-a]pyrimidina-4(3,2)-pyridina-cyclononaphan]-9'-one | MS-ESI (m/z): 383 [M + 1]⁺ |
| 46 | 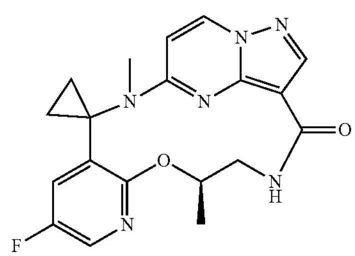 [SMILES: C[C@@H]1CNC(=O)c2cnn3ccc(nc23)N(C)C2(CC2)c2cc(F)cnc2O1] | (R,3'E,4'E)-5'-fluoro-2',6'-dimethylspiro-[cyclopropane-1,3'-5-oxa-2,8-diaza-1(5,3)-pyrazolo[1,5-a]pyrimidina-4(3,2)-pyridinacyclononaphan]-9'-one | MS-ESI (m/z): 383 [M + 1]⁺ |
| 47 | 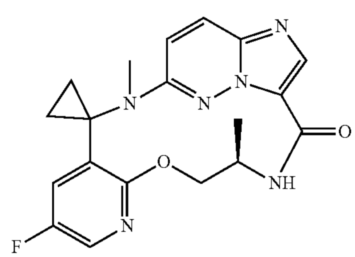 [SMILES: C[C@@H]1COc2ncc(F)cc2C2(CC2)N(C)c2ccc3ncc(n3n2)C(=O)N1] | (7'R,E)-5'-fluoro-2',7'-dimethylspiro-[cyclopropane-1,3'-5-oxa-2,8-diaza-1(6,3)-imidazo[1,2-b]pyridazina-4(3,2)-pyridina-cyclononaphan]-9'-one | MS-ESI (m/z): 383 [M + 1]⁺ |
| 48 | 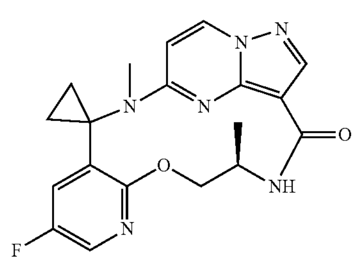 [SMILES: C[C@@H]1COc2ncc(F)cc2C2(CC2)N(C)c2ccn3ncc(c3n2)C(=O)N1] | (R,3'E,4'E)-5'-fluoro-2',7'-dimethylspiro-[cyclopropane-1,3'-5-oxa-2,8-diaza-1(5,3)-pyrazolo[1,5-a]pyrimidina-4(3,2)-pyridina-cyclononaphan]-9'-one | MS-ESI (m/z): 383 [M + 1]⁺ |

TABLE 1-continued

| EXAMPLE | STRUCTURE | NAME | DATA |
|---|---|---|---|
| 49 | 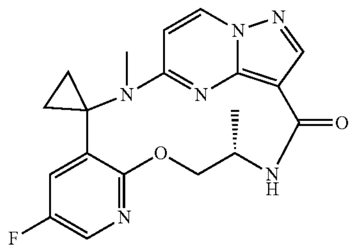 [SMILES: C[C@H]1COc2ncc(F)cc2C2(CC2)N(C)c2ccn3ncc(c3n2)C(=O)N1] | (S,3'E,4'E)-5'-fluoro-2',7'-dimethylspiro-[cyclopropane-1,3'-5-oxa-2,8-diaza-1(5,3)-pyrazolo[1,5-a]pyrimidina-4(3,2)-pyridinacyclononaphan]-9'-one | MS-ESI (m/z): 383 [M + 1]+ |
| 50 | 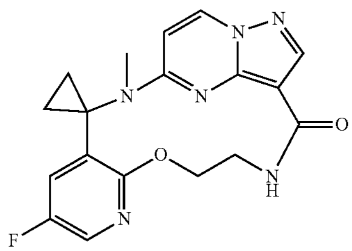 [SMILES: CN1c2ccn3ncc(c3n2)C(=O)NCCOc2ncc(F)cc2C12CC2] | (3'E,4'E)-5'-fluoro-2'-methylspiro-[cyclopropane-1,3'-5-oxa-2,8-diaza-1(5,3)-pyrazolo[1,5-a]pyrimidina-4(3,2)-pyridina-cyclononaphan]-9'-one | MS-ESI (m/z): 369 [M + 1]+ |
| 51 | 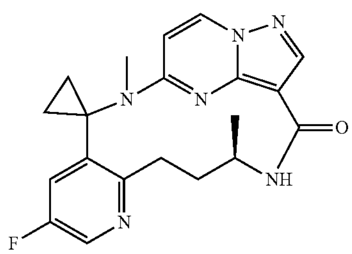 [SMILES: C[C@@H]1CCc2ncc(F)cc2C2(CC2)N(C)c2ccn3ncc(c3n2)C(=O)N1] | (R,3'E,4'E)-5'-fluoro-2',7'-dimethylspiro-[cyclopropane-1,3'-2,8-diaza-1(5,3)-pyrazolo[1,5-a]pyrimidina-4(3,2)-pyridina-cyclononaphan]-9'-one | MS-ESI (m/z): 381 [M + 1]+ |
| 52 | 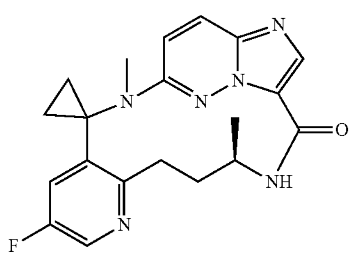 [SMILES: C[C@@H]1CCc2ncc(F)cc2C2(CC2)N(C)c2ccc3ncc(n3n2)C(=O)N1] | (7'R,E)-5'-fluoro-2',7'-dimethylspiro-[cyclopropane-1,3'-2,8-diaza-1(6,3)-imidazo[1,2-b]pyridazina-4(3,2)-pyridinacyclo-nonaphan]-9'-one | MS-ESI (m/z): 381 [M + 1]+ |
| 53 | 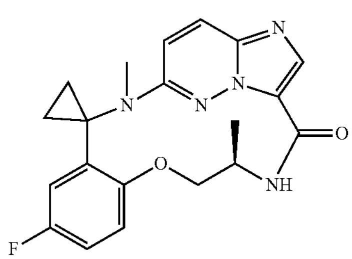 [SMILES: C[C@@H]1COc2ccc(F)cc2C2(CC2)N(C)c2ccc3ncc(n3n2)C(=O)N1] | (7'R,E)-5'-fluoro-2',7'-dimethylspiro-[cyclopropane-1,3'-5-oxa-2,8-diaza-1(6,3)-imidazo[1,2-b]pyridazina-4(1,2)-benzenacyclononaphan]-9'-one | MS-ESI (m/z): 382 [M + 1]+ |
| 54 | 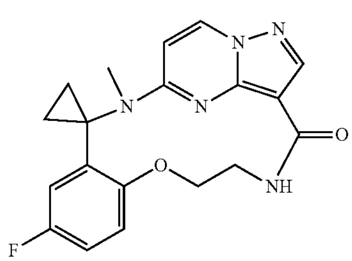 [SMILES: CN1c2ccn3ncc(c3n2)C(=O)NCCOc2ccc(F)cc2C12CC2] | (3'E,4'E)-5'-fluoro-2'-methylspiro-[cyclopropane-1,3'-5-oxa-2,8-diaza-1(5,3)-pyrazolo[1,5-a]pyrimidina-4(1,2)-benzenacyclononaphan]-9'-one | MS-ESI (m/z): 368 [M + 1]+ |

TABLE 1-continued

| EXAMPLE | NAME | DATA |
|---|---|---|
| 55 | (R,3'E,4'E)-5'-fluoro-2',7'-dimethylspiro[cyclopropane-1,3'-2,8-diaza-1(5,3)-pyrazolo[1,5-a]pyrimidina-4(1,2)-benzenecyclononaphan]-9'-one | MS-ESI (m/z): 380 [M + 1]⁺ |
| 56 | (7'R,E)-5'-fluoro-2',7'-dimethylspiro-[cyclopropane-1,3'-2,8-diaza-1(6,3)-imidazo[1,2-b]pyridazina-4(1,2)-benzenacyclononaphan]-9'-one | MS-ESI (m/z): 380 [M + 1]⁺ |
| 57 | (S,3'E,4'E)-2'-ethyl-5'-fluoro-6'-methyl-spiro[cyclopropane-1,3'-5-oxa-2,8-diaza-1(5,3)-pyrazolo[1,5-a]pyrimidina-4(1,2)-benzenacyclononaphan]-9'-one | MS-ESI (m/z): 396 [M + 1]⁺ |
| 58 | (R,3'E,4'E)-2'-ethyl-5'-fluoro-6'-methyl-spiro[cyclopropane-1,3'-5-oxa-2,8-diaza-1(5,3)-pyrazolo[1,5-a]pyrimidina-4(1,2)-benzenacyclononaphan]-9'-one | MS-ESI (m/z): 396 [M + 1]⁺ |
| 59 | (R,3'E,4'E)-2'-ethyl-5'-fluoro-7'-methyl-spiro[cyclopropane-1,3'-5-oxa-2,8-diaza-1(5,3)-pyrazolo[1,5-a]pyrimidina-4(1,2)-benzenacyclononaphan]-9'-one | MS-ESI (m/z): 396 [M + 1]⁺ |
| 60 | (S,3'E,4'E)-2'-ethyl-5'-fluoro-7'-methyl-spiro[cyclopropane-1,3'-5-oxa-2,8-diaza-1(5,3)-pyrazolo[1,5-a]pyrimidina-4(1,2)-benzenacyclononaphan]-9'-one | MS-ESI (m/z): 396 [M + 1]⁺ |

TABLE 1-continued

| EXAMPLE | NAME | DATA |
|---|---|---|
| 61 | (3'E,4'E)-2'-ethyl-5'-fluorospiro-[cyclopropane-1,3'-5-oxa-2,8-diaza-1(5,3)-pyrazolo[1,5-a]pyrimidina-4(1,2)-benzenacyclononaphan]-9'-one | MS-ESI (m/z): 382 [M + 1]+ |
| 62 | (S,3'E,4'E)-2'-ethyl-5'-fluoro-6'-methylspiro[cyclopropane-1,3'-5-oxa-2,8-diaza-1(5,3)-pyrazolo[1,5-a]pyrimidina-4(3,2)-pyridinacyclononphan]-9'-one | MS-ESI (m/z): 397 [M + 1]+ |
| 63 | (R,3'E,4'E)-2'-ethyl-5'-fluoro-6'-methyl-spiro[cyclopropane-1,3'-5-oxa-2,8-diaza-1(5,3)-pyrazolo[1,5-a]pyrimidina-4(3,2)-pyridinacyclononaphan]-9'-one | MS-ESI (m/z): 397 [M + 1]+ |
| 64 | (R,3'E,4'E)-2'-ethyl-5'-fluoro-7'-methylspiro[cyclopropane-1,3'-5-oxa-2,8-diaza-1(5,3)-pyrazolo[1,5-a]pyrimidina-4(3,2)-pyridinacyclononaphan]-9'-one | MS-ESI (m/z): 397 [M + 1]+ |
| 65 | (S,3'E,4'E)-2'-ethyl-5'-fluoro-7'-methylspiro[cyclopropane-1,3'-5-oxa-2,8-diaza-1(5,3)-pyrazolo[1,5-a]pyrimidina-4(3,2)-pyridinacyclononaphan]-9'-one | MS-ESI (m/z): 397 [M + 1]+ |
| 66 | (3'E,4'E)-2'-ethyl-5'-fluorospiro-[cyclopropane-1,3'-5-oxa-2,8-diaza-1(5,3)-pyrazolo[1,5-a]pyrimidina-4(3,2)-pyridinacyclononaphan]-9'-one | MS-ESI (m/z): 383 [M + 1]+ |

TABLE 1-continued

| EXAMPLE | NAME | DATA |
|---|---|---|
| 67 | (3'E,4'E)-5'-fluorospiro[cyclopropane-1,3'-5-oxa-2,9-diaza-1(5,3)-pyrazolo[1,5-a]pyrimidina-4(3,2)-pyridinacyclodecaphan]-10'-one | MS-ESI (m/z): 369 [M + 1]⁺ |
| 68 | (3'E,4'E)-5'-fluoro-2'-methylspiro-[cyclopropane-1,3'-5-oxa-2,9-diaza-1(5,3)-pyrazolo[1,5-a]pyrimidina-4(3,2)-pyridina-cyclodecaphan]-10'-one | MS-ESI (m/z): 383 [M + 1]⁺ |
| 69 | (3'E,4'E)-5'-fluoro-2'-methyldispiro-[cyclopropane-1,3'-5-oxa-2,8-diaza-1(5,3)-pyrazolo[1,5-a]pyrimidina-4(1,2)-benzenacyclononaphane-7',1''-cyclopropan]-9'-one | MS-ESI (m/z): 394 [M + 1]⁺ |
| 70 | (1'R,3'E,4'E,5'S)-5'-fluorospiro-[cyclopropane-1,6'-4-oxa-2²,7-diaza-1(5,3)-pyrazolo[1,5-a]pyrimidina-3(3,2)-pyridina-2(2,1)-bicyclo[3.1.0]hexanacyclo-octaphan]-8'-one | MS-ESI (m/z): 407 [M + 1]⁺ |
| 71 | (1³E,1⁴E,2¹R,2⁵S)-3⁵-fluoro-2²,7-diaza-1(5,3)-pyrazolo[1,5-a]pyrimidina-2(2,1)-bicyclo[3.1.0]hexana-3(1,2)-benzenacyclo-octaphan-8-one | MS-ESI (m/z): 378 [M + 1]⁺ |
| 72 | (2¹R,2⁵S,5S,E)-3⁵-fluoro-5-methyl-4-oxa-2²,7-diaza-1(6,3)-imidazo[1,2-b]pyridazina-3(3,2)-pyridina-2(2,1)-bicyclo[3.1.0]hexanacyclooctaphan-8-one | MS-ESI (m/z): 395 [M + 1]⁺ |

TABLE 1-continued

| EXAMPLE | NAME | DATA |
|---|---|---|
| 73 | (S,3'E,4'E)-4'-fluoro-8'-methylspiro-[cyclopropane-1,7'-5-oxa-8-aza-1(3,5)-pyrazolo[1,5-a]pyrimidina-3(1,2)-pyrrolidina-6(1,2)-benzenacyclooctaphan]-2'-one | MS-ESI (m/z): 408 [M + 1]+ |
| 74 | (R,3'E,4'E)-4'-fluoro-8'-methylspiro-[cyclopropane-1,7'-5-oxa-8-aza-1(3,5)-pyrazolo[1,5-a]pyrimidina-3(1,2)-pyrrolidina-6(1,2)-benzenacyclooctaphan]-2'-one | MS-ESI (m/z): 408 [M + 1]+ |
| 75 | (3'E,4'E)-5'-fluoro-2'-methyldispiro-[cyclobutane-1,7'-5-oxa-2,8-diaza-1(5,3)-pyrazolo[1,5-a]pyrimidina-4(3,2)-pyridinacyclononaphane-3',1'''-cyclopropan]-9'-one | MS-ESI (m/z): 409 [M + 1]+ |
| 76 | (1³E,1⁴E,2¹E,2¹R,2⁵S)-3⁵-fluoro-4-oxa-2²,8-diaza-1(5,3)-pyrazolo[1,5-a]pyrimidina-3(3,2)-pyridina-2(2,1)-bicyclo[3.1.0]hexana-cyclononaphan-9-one | MS-ESI (m/z): 395 [M + 1]+ |
| 77 | (1'R,3'E,4'E,5'S)-5'-fluorospiro-[cyclopropane-1,6'-2²,7-diaza-1(5,3)-pyrazolo[1,5-a]pyrimidina-3(3,2)-pyridina-2(2,1)-bicyclo[3.1.0]hexanacyclooctaphan]-8'-one | MS-ESI (m/z): 405 [M + 1]+ |
| 78 | (1'R,5'S,E)-5'fluorospiro[cyclopropane-1,6'-2²,7-diaza-1(6,3)-imidazo[1,2-b]pyridazina-3(3,2)-pyridina-2(2,1)-bicyclo[3.1.0]hexanacyclooctaphan]-8'-one | MS-ESI (m/z): 405 [M + 1]+ |

TABLE 1-continued

| EXAMPLE | STRUCTURE | NAME | DATA |
|---|---|---|---|
| 79 | 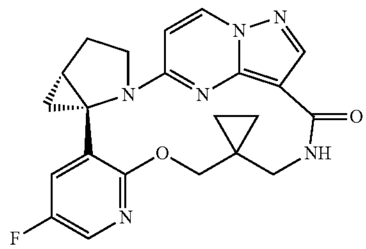 [SMILES: O=C1NCC2(CC2)COc2ncc(F)cc2[C@@]23C[C@@H]2CCN3c2ccn3ncc1c3n2] | (1'R,3'E,4'E,5'S)-5'-fluorospiro-[cyclopropane-1,6'-4-oxa-2²,8-diaza-1(5,3)-pyrazolo[1,5-a]pyrimidina-3(3,2)-pyridina-2(2,1)-bicyclo[3.1.0]hexana-cyclononaphan]-9'-one | MS-ESI (m/z): 421 [M + 1]⁺ |
| 80 | 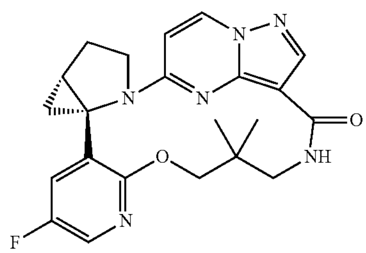 [SMILES: CC1(C)CNC(=O)c2cnn3ccc(nc23)N2CC[C@H]3C[C@]32c2cc(F)cnc2OC1] | (1³E,1⁴E,2¹R,2⁵S)-3⁵-fluoro-6,6-dimethyl-4-oxa-2²,8-diaza-1(5,3)-pyrazolo[1,5-a]pyrimidina-3(3,2)-pyridina-2(2,1)-bicyclo[3.1.0]hexanacyclononaphan-9-one | MS-ESI (m/z): 423 [M + 1]⁺ |
| 81 | 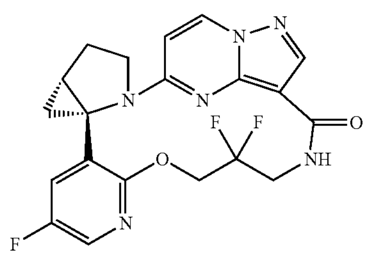 [SMILES: O=C1NCC(F)(F)COc2ncc(F)cc2[C@@]23C[C@@H]2CCN3c2ccn3ncc1c3n2] | (1³E,1⁴E,2¹R,2⁵S)-3⁵,6,6-trifluoro-4-oxa-2²,8-diaza-1(5,3)-pyrazolo[1,5-a]pyrimidina-3(3,2)-pyridina-2(2,1)-bicyclo[3.1.0]hexanacyclononaphan-9-one | MS-ESI (m/z): 431 [M + 1]⁺ |
| 82 | 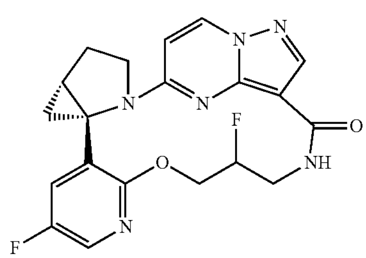 [SMILES: O=C1NCC(F)COc2ncc(F)cc2[C@@]23C[C@@H]2CCN3c2ccn3ncc1c3n2] | (1³E,1⁴E,2¹R,2⁵S)-3⁵,6-difluoro-4-oxa-2²,8-diaza-1(5,3)-pyrazolo[1,5-a]pyrimidina-3(3,2)-pyridina-2(2,1)-bicyclo[3.1.0]hexanacyclononaphan-9-one | MS-ESI (m/z): 413 [M + 1]⁺ |
| 83 | 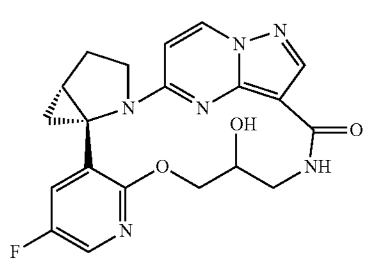 [SMILES: O=C1NCC(O)COc2ncc(F)cc2[C@@]23C[C@@H]2CCN3c2ccn3ncc1c3n2] | (1³E,1⁴E,2¹R,2⁵S)-3⁵-fluoro-6-hydroxy-4-oxa-2²,8-diaza-1(5,3)-pyrazolo[1,5-a]pyrimidina-3(3,2)-pyridina-2(2,1)-bicyclo[3.1.0]hexanacyclononaphan-9-one | MS-ESI (m/z): 411 [M + 1]⁺ |
| 84 | 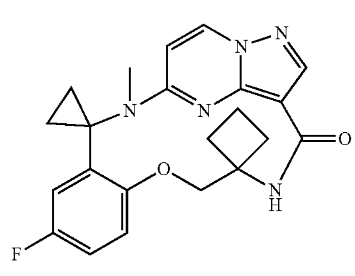 [SMILES: CN1c2ccn3ncc(c3n2)C(=O)NC2(CCC2)COc2ccc(F)cc2C12CC2] | (3'E,4'E)-5'-fluoro-2'-methyldispiro-[cyclobutane-1,7'-5-oxa-2,8-diaza-1(5,3)-pyrazolo[1,5-a]pyrimidina-4(1,2)-benzenacyclononaphane-3',1''-cyclopropan]-9'-one | MS-ES (m/z): 408 [M + 1]⁺ |

TABLE 1-continued

| EXAMPLE | NAME | DATA |
|---|---|---|
| 85 | (3'E,4'E)-5'-fluoro-2'-methyldispiro-[cyclopropane-1,3'-2,8-diaza-1(5,3)-pyrazolo[1,5-a]pyrimidina-4(3,2)-pyridinacyclononaphane-7',1''-cyclopropan]-9'-one | MS-ESI (m/z): 393 [M + 1]+ |
| 86 | (3'E,4'E)-5'-fluoro-2'-methyldispiro-[cyclopropane-1,3'-5-thia-2,8-diaza-1(5,3)-pyrazolo[1,5-a]pyrimidina-4(3,2)-pyridina-cyclononaphane-7',1''-cyclopropan]-9'-one | MS-ESI (m/z): 411 [M + 1]+ |
| 87 | (3'E,4'E)-5'-fluoro-2'-methylspiro-[cyclopropane-1,3'-2,5,8-triaza-1(5,3)-pyrazolo[1,5-a]pyrimidina-4(3,2)-pyridinacyclononaphan]-9'-one | MS-ESI (m/z): 368 [M + 1]+ |
| 88 | (3'E,4'E)-5'-fluoro-2'-methylspiro-[cyclopropane-1,3'-5,8-dioxa-2-aza-1(5,3)-pyrazolo[1,5-a]pyrimidina-4(1,2)-benzenacyclononaphan]-9'-one | MS-ESI (m/z): 369 [M + 1]+ |
| 89 | (3'E,4'E)-5'-fluoro-2'-(methyl-d$_3$)dispiro[cyclopropane-1,3'-5-oxa-2,8-diaza-1(5,3)-pyrazolo[1,5-a]pyrimidina-4(1,2)-benzena-cyclononaphan-7',1''-cyclopropan]-9'-one | MS-ESI (m/z): 397 [M + 1]+ |
| 90 | (3'E,4'E)-4'-fluoro-8'-methylspiro-[cyclopropane-1,7'-5-oxa-8-aza-1(3,5)-pyrazolo[1,5-a]pyrimidina-3(1,2)-azetidina-6(1,2)-benzenacyclooctaphan]-2'-one | MS-ESI (m/z): 394 [M + 1]+ |

TABLE 1-continued

| EXAMPLE | STRUCTURE | NAME | DATA |
| --- | --- | --- | --- |
| 91 | 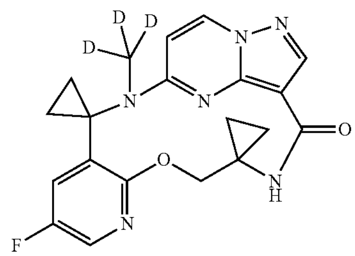 [SMILES: [2H]C([2H])([2H])N1c2ccn3ncc(c3n2)C(=O)NC2(CC2)COc2ncc(F)cc2C12CC2] | (3'E,4'E)-5'-fluoro-2'-(methyl-d₃)dispiro-[cyclopropane-1,3'-5-oxa-2,8-diaza-1(5,3)-pyrazolo[1,5-a]pyrimidina-4(3,2)-pyridina-cyclononaphane-7',1''-cyclopropan]-9'-one | MS-ESI (m/z): 398 [M + 1]⁺ |
| 92 | 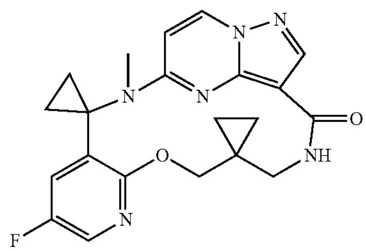 [SMILES: CN1c2ccn3ncc(c3n2)C(=O)NCC2(CC2)COc2ncc(F)cc2C12CC2] | (3'E,4'E)-5'-fluoro-2'-methyldispiro-[cyclopropane-1,3'-5-oxa-2,9-diaza-1(5,3)-pyrazolo[1,5-a]pyrimidina-4(3,2)-pyridina-cyclodecaphane-7',1''-cyclopropan]-10'-one | MS-ESI (m/z): 409 [M + 1]⁺ |
| 93 | 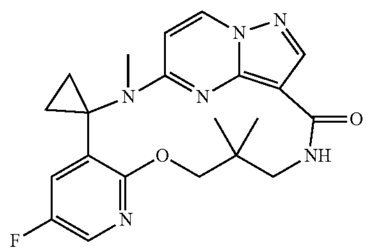 [SMILES: CN1c2ccn3ncc(c3n2)C(=O)NCC(C)(C)COc2ncc(F)cc2C12CC2] | (3'E,4'E)-5'-fluoro-2',7',7'-trimethylspiro-[cyclopropane-1,3'-5-oxa-2,9-diaza-1(5,3)-pyrazolo[1,5-a]pyrimidina-4(3,2)-pyridina-cyclodecaphan]-10'-one | MS-ESI (m/z): 411 [M + 1]⁺ |
| 94 | 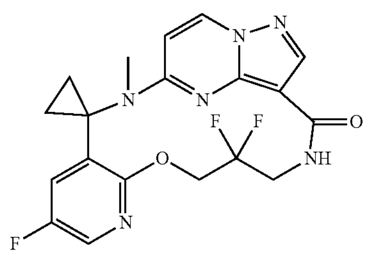 [SMILES: CN1c2ccn3ncc(c3n2)C(=O)NCC(F)(F)COc2ncc(F)cc2C12CC2] | (3'E,4'E)-5',7',7'-trifluoro-2'-methylspiro-[cyclopropane-1,3'-5-oxa-2,9-diaza-1(5,3)-pyrazolo[1,5-a]pyrimidina-4(4,3)-pyridina-cyclodecaphan]-10'-one | MS-ESI (m/z): 419 [M + 1]⁺ |
| 95 | 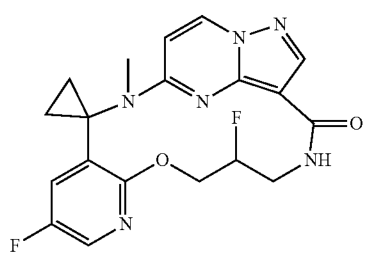 [SMILES: CN1c2ccn3ncc(c3n2)C(=O)NCC(F)COc2ncc(F)cc2C12CC2] | (3'E,4'E)-5',7'-difluoro-2'-methylspiro-[cyclopropane-1,3'-5-oxa-2,9-diaza-1(5,3)-pyrazolo[1,5-a]pyrimidina-4(3,2)-pyridina-cyclodecaphan]-10'-one | MS-ESI (m/z): 401 [M + 1]⁺ |
| 96 | 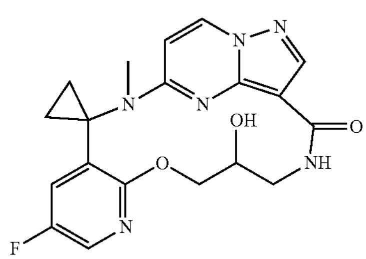 [SMILES: CN1c2ccn3ncc(c3n2)C(=O)NCC(O)COc2ncc(F)cc2C12CC2] | (3'E,4'E)-5'-fluoro-7'-hydroxy-2'-methyl-spiro[cyclopropane-1,3'-5-oxa-2,9-diaza-1(5,3)-pyrazolo[1,5-a]pyrimidina-4(3,2)-pyridinacyclodecaphan]-10'-one | MS-ESI (m/z): 399 [M + 1]⁺ |

TABLE 1-continued

| EXAMPLE | STRUCTURE | NAME | DATA |
|---|---|---|---|
| 97 | 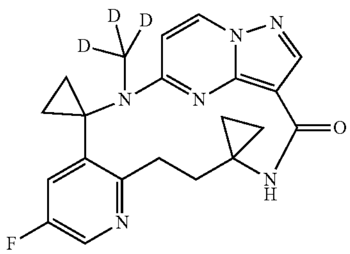 | (3'E,4'E)-5'-fluoro-2'-(methyl-d₃)-dispiro[cyclopropane-1,3'-2,8-diaza-1(5,3)-pyrazolo[1,5-a]pyrimidina-4(3,2)-pyridinacyclononaphane-7',1''-cyclopropan]-9'-one | MS-ESI (m/z): 396 [M + 1]⁺ |
| 98 | 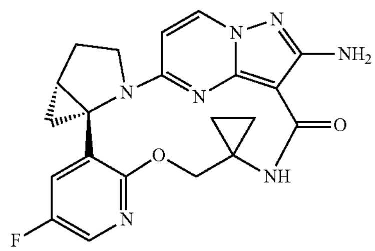 [SMILES: Nc1nn2ccc3nc2c1C(=O)NC1(CC1)COc1ncc(F)cc1[C@@]12C[C@@H]1CCN32] | (1'R,3'E,4'E,5'S)-2'-amino-5'-fluorospiro-[cyclopropane-1,6'-4-oxa-2²,7-diaza-1(5,3)-pyrazolo[1,5-a]pyrimidina-3(3,2)-pyridina-2(2,1)-bicyclo[3.1.0]-hexanacyclooctaphan]-8'-one | MS-ESI (m/z): 422 [M + 1]⁺ |
| 99 | 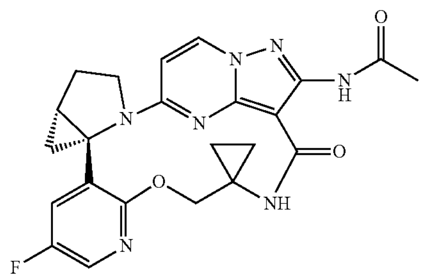 [SMILES: CC(=O)Nc1nn2ccc3nc2c1C(=O)NC1(CC1)COc1ncc(F)cc1[C@@]12C[C@@H]1CCN32] | N-((1'R,3'E,4'E,5'S)-5'-fluoro-8'-oxospiro[cyclopropane-1,6'-4-oxa-2²,7-diaza-1(5,3)-pyrazolo[1,5-a]pyrimidina-3(3,2)-pyridina-2(2,1)-bicyclo[3.1.0]hexanacyclooctaphan]-2'-yl)acetamide | MS-ESI (m/z): 464 [M + 1]⁺ |
| 100 | 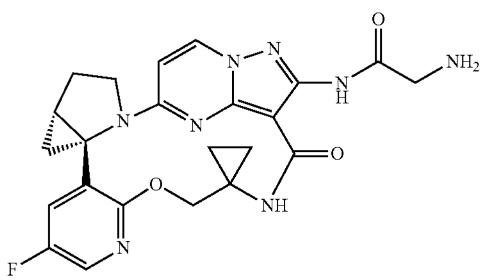 [SMILES: NCC(=O)Nc1nn2ccc3nc2c1C(=O)NC1(CC1)COc1ncc(F)cc1[C@@]12C[C@@H]1CCN32] | 2-amino-N-((1'R,3'E,4'E,5'S)-5'-fluoro-8'-oxospiro[cyclopropane-1,6'-4-oxa-2²,7-diaza-1(5,3)-pyrazolo[1,5-a]pyrimidina-3(3,2)-pyridina-2(2,1)-bicyclo[3.1.0]hexana-cyclooctaphan]-2'-yl)acetamide | MS-ESI (m/z): 479 [M + 1]⁺ |

Biological Activity

MTS testing kit was purchased from Promega (Madison, Wis., USA). The RPMI-1640, Fetal bovine serum and Penicillin-Streptomycin were purchased from Gibco (San Francisco, Calif., USA). Dimethyl sulfoxide (DMSO) and Puromycin were purchased from Sigma (St. Louis., Mo., USA). Mouse interleukin-3 (IL-3) was purchased from Cell signaling Technology (Boston, Mass., USA).

To investigate whether a compound is able to inhibit the activity of TRK in cells, a mechanism-based assay using KM12 cells was developed. In this assay, inhibition of TRK was detected by the inhibition of KM12 cells proliferation. KM12 cells were cultured in culture flasks to 40-80% confluence in RPMI-1640 plus 10% fetal bovine serum. Cells were collected and plated onto 96-well plates at 1000 cells/well. Plates were incubated at 37° C., with 5% $CO_2$ for 4 h. Compounds were added to the plates, the final compound concentrations were 10000, 3333.3, 1111.1, 270.4, 123.5, 41.2, 13.7, 4.6 and 1.5 nM. Place plates at 37° C., with 5% $CO_2$ for KM12 cells 72 h. 20 μl MTS/100 μl medium mixture solution were added to each well and incubate the plates for exactly 2 h. Stop the reaction by adding 25 μl 10% SDS per well. Measure absorbance at 490 nm and 650 nm (reference wavelength). $IC_{50}$ was calculated using GraphPad Prism 5.0.

To investigate whether a compound is able to inhibit the activity of TRK fusion mutation in cells, a mechanism-based assay using engineered Ba/F3 cell lines stably overexpressing oncogenic rearrangement or gene mutation of TRK (TPM3-TRKA, TPM3-TRKA-G595R, AFAP1-TRKB, ETV6-TRKC and ETV6-TRKC-G623R) were developed. In this assay, inhibition of TRK fusion mutation was detected by the cell proliferation inhibition of engineered Ba/F3 cells. Engineered Ba/F3 cells were cultured in culture flasks to 40-80% confluence in RPMI-1640 supplemented with 10% fetal bovine serum, 2 ug/mL puromycin. Cells were collected and plated onto 96-well plates at desired cell density (Ba/F3-TPM3-TRKA: 3×10⁴/mL, Ba/F3-TPM3-TRKA-G595R: 1×10⁵/mL, Ba/F3-AFAP1-TRKB: 1×10⁵/mL, Ba/F3-ETV6-TRKC: 3×10⁴/mL, Ba/F3-ETV6-TRKC- G623R: 3×10⁴/mL). Plates were incubated at 37° C., with 5% $CO_2$ for 4 h. Compounds were then added to the plates with the final compound concentrations of 10000, 3333, 1111, 270, 123, 41.2, 13.7, 4.6 and 1.5 nM. Plates were incubated at 37° C., with 5% $CO_2$ for 72 h. A mixture of 20 μl MTS/100 μl medium were added to each well and the plates were incubated at 37° C., with 5% $CO_2$ for exactly 2 h. The reaction was stopped by adding 25 μl of 10% SDS per well. The absorbance was measured at 490 nm and 650 nm (reference wavelength). $IC_{50}$ was calculated using GraphPad Prism 5.0 software.

Select compounds prepared as described above were assayed according to the biological procedures described herein. The results are given in Table 2.

TABLE 2

| Example | KM12 $IC_{50}$ (nM) | TPM3-TRKA $IC_{50}$ (nM) | TPM3-TRKA-G595R $IC_{50}$ (nM) | ETV6-TRKC $IC_{50}$ (nM) | ETV6-TRKC-G623R $IC_{50}$ (nM) |
|---|---|---|---|---|---|
| 1 | 1 | / | / | / | / |
| 2 | 1 | / | / | / | / |
| 3 | 1 | / | / | 1 | / |
| 4 | 1 | / | / | / | / |
| 5 | 1 | / | / | / | / |
| 6 | 1 | / | / | / | / |
| 7 | 1 | / | / | / | / |
| 8 | 4 | 3 | 67 | 1 | 39 |
| 9 | 7 | / | / | / | / |
| 10 | 1 | / | / | / | / |
| 11 | 1 | / | 36 | / | 41 |
| 12A | 1 | / | / | / | / |
| 12B | 2 | / | / | / | / |
| 13 | 1 | / | / | / | / |
| 14 | 1 | / | / | / | / |
| 15 | 1 | 1 | 1 | 1 | 1 |
| 16 | 1 | 1 | 1 | 1 | 2 |
| 17 | 1 | 1 | 5 | / | 1 |
| 18 | 1 | 1 | 1 | 1 | 2 |
| 19 | 1 | 1 | 1 | 1 | 1 |
| 20 | 1 | 1 | 1 | 1 | 1 |
| 21 | 1 | 1 | / | / | 1 |
| 22 | 1 | 1 | 1 | 1 | 1 |
| 23 | 1 | 1 | 4 | / | 5 |
| 24 | 1 | 1 | 1 | 1 | 4 |
| 25 | 2 | / | / | / | 7 |
| 26 | 1 | / | / | / | 1 |
| 27 | 1 | 1 | 1 | 1 | 1 |
| 28 | 1 | 1 | / | / | 6 |
| 29 | 1 | 1 | 1 | 1 | 1 |
| 30 | 1 | 1 | / | / | 2 |
| 31 | 1 | 1 | 1 | 1 | 3 |
| 32 | 1 | / | / | / | / |
| 33A | 1 | / | / | / | / |
| 33B | 1 | / | / | / | / |
| 34 | 1 | / | / | / | / |
| 35 | 1 | / | / | / | / |
| 36 | 6 | 2 | 17 | 3 | 13 |
| 37 | 9 | 1 | 10 | 3 | 8 |
| 38 | 3 | 1 | 1 | 2 | 23 |
| 39 | 1 | 1 | 1 | 1 | 17 |
| 41 | 1 | 1 | 30 | / | 26 |
| 42 | 3 | / | / | / | / |
| 44 | 35 | 18 | / | 26 | / |
| 45 | 2 | 3 | 25 | 1 | 15 |
| 47 | 2 | / | 26 | / | 23 |
| 48 | 2 | / | 14 | / | 12 |
| 50 | 10 | 11 | / | 2 | 68 |
| 51 | 3 | / | 72 | / | 44 |
| 53 | 30 | / | / | / | / |
| 54 | 9 | 13 | / | / | 62 |
| 55 | 5 | / | / | / | 87 |
| 56 | 3 | / | / | / | / |
| 59 | 1 | 17 | / | / | / |
| 62 | 13 | 46 | / | / | / |
| 64 | 2 | 6 | / | / | 68 |
| 66 | 34 | 60 | / | 15 | / |
| 67 | 10 | 23 | / | / | / |
| 68 | 10 | 8 | 53 | / | 33 |
| 69 | 1 | / | 1 | / | 4 |
| 70 | / | / | 1 | / | 1 |
| 71 | 1 | / | 1 | / | 1 |
| 72 | / | / | 3 | / | 5 |
| 75 | / | / | 25 | / | 19 |
| 76 | / | / | / | / | 1 |
| 77 | 1 | / | 1 | / | 1 |
| 78 | 1 | / | 3 | / | 1 |

TABLE 2-continued

| Example | KM12 IC$_{50}$ (nM) | TPM3-TRKA IC$_{50}$ (nM) | TPM3-TRKA-G595R IC$_{50}$ (nM) | ETV6-TRKC IC$_{50}$ (nM) | ETV6-TRKC-G623R IC$_{50}$ (nM) |
|---|---|---|---|---|---|
| 79 | / | / | / | / | 1 |
| 80 | / | / | / | / | 4 |
| 81 | / | / | / | / | 1 |
| 82 | / | / | / | / | 1 |
| 83 | / | / | / | / | 1 |
| 84 | / | / | 46 | / | 29 |
| 85 | / | / | 15 | / | 45 |
| 86 | 1 | / | 1 | / | 1 |
| 89 | / | / | / | / | 1 |
| 91 | / | / | / | / | 2 |
| 92 | / | / | / | / | 5 |
| 93 | / | / | / | / | 32 |
| 94 | / | / | / | / | 25 |
| 95 | / | / | / | / | 1 |
| 96 | / | / | / | / | 4 |
| 97 | / | / | / | / | 25 |
| 98 | / | / | / | / | 1 |

What is claimed is:

1. A compound of formula (I):

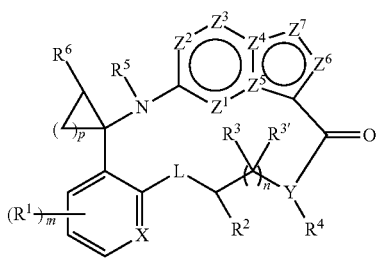

(I)

or a pharmaceutically acceptable salt thereof, wherein

X is selected from $CR^X$ and N;

Y is selected from O and N, wherein when Y is O, $R^4$ is absent;

$Z^1, Z^2, Z^3, Z^6$ and $Z^7$ are independently selected from $CR^X$ and N;

$Z^4$ and $Z^5$ are independently selected from C and N, wherein when one of $Z^4$ and $Z^5$ is N, then the other of $Z^4$ and $Z^5$ is C;

L is selected from —(CR$^C$R$^D$)$_u$—, —(CR$^C$R$^D$)$_u$O(CR$^C$R$^D$)$_t$—, —(CR$^C$R$^D$)$_u$NR$^A$(CR$^C$R$^D$)$_t$— and —(CR$^C$R$^D$)$_u$S(CR$^C$R$^D$)$_t$—;

each $R^1$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, NO$_2$, —NR$^{A1}$R$^{B1}$, —OR$^{A1}$, —C(O)R$^{A1}$, —C(=NR$^{E1}$)R$^{A1}$, —C(=N—OR$^{B1}$)R$^{A1}$, —C(O)OR$^{A1}$, —OC(O)R$^{A1}$, —C(O)NR$^{A1}$R$^{B1}$, —NR$^{A1}$C(O)R$^{B1}$, —C(=NR$^{E1}$)NR$^{A1}$R$^{B1}$, —NR$^{A1}$C(=NR$^{E1}$)R$^{B1}$, —OC(O)NR$^{A1}$R$^{B1}$, —NR$^{A1}$C(O)OR$^{B1}$, —NR$^{A1}$C(O)NR$^{A1}$R$^{B1}$, —NR$^{A1}$C(S)NR$^{A1}$R$^{B1}$, —NR$^{A1}$C(=NR$^{E1}$)NR$^{A1}$R$^{B1}$, —S(O)$_r$R$^{A1}$, —S(O)(=NR$^{E1}$)R$^{B1}$, —N=S(O)R$^{A1}$R$^{B1}$, —S(O)$_2$OR$^{A1}$, —OS(O)$_2$R$^{A1}$, —NR$^{A1}$S(O)$_r$R$^{B1}$, —NR$^{A1}$S(O)(=NR$^{E1}$)R$^{B1}$, —S(O)$_r$NR$^{A1}$R$^{B1}$, —S(O)(=NR$^{E1}$)NR$^{A1}$R$^{B1}$, —NR$^{A1}$S(O)$_2$NR$^{A1}$R$^{B1}$, —NR$^{A1}$S(O)(=NR$^{E1}$)NR$^{A1}$R$^{B1}$, —P(O)R$^{A1}$R$^{B1}$, and —P(O)(OR$^{A1}$)(OR$^{B1}$), wherein alkyl, alkenyl, alkynyl, cycloalkyl, heterocyclyl, aryl and heteroaryl are each unsubstituted or substituted with at least one substituent, independently selected from $R^X$;

$R^2$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, —NR$^{A2}$R$^{B2}$, —OR$^{A2}$, —C(O)R$^{A2}$, —C(O)OR$^{A2}$, —OC(O)R$^{A2}$, —C(O)NR$^{A2}$R$^{B2}$, —NR$^{A2}$C(O)R$^{B2}$ and —S(O)$_r$R$^{A2}$, wherein alkyl, alkenyl, alkynyl, cycloalkyl, heterocyclyl, aryl and heteroaryl are each unsubstituted or substituted with at least one substituent, independently selected from $R^X$;

each $R^3$ and $R^{3'}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, —NR$^{A3}$R$^{B3}$, —OR$^{A3}$, —C(O)R$^{A3}$, —C(O)OR$^{A3}$, —OC(O)R$^{A3}$, —C(O)NR$^{A3}$R$^{B3}$, —NR$^{A3}$C(O)R$^{B3}$, and —S(O)$_r$R$^{A3}$, wherein alkyl, alkenyl, alkynyl, cycloalkyl, heterocyclyl, aryl and heteroaryl are each unsubstituted or substituted with at least one substituent, independently selected from $R^X$; or "$R^2$ and $R^3$," or "$R^2$ and $R^{3'}$" together with the carbon atoms to which they are attached form a $C_{5-7}$ cycloalkyl or heterocyclic ring of 3 to 7 members containing 1, 2 or 3 heteroatoms independently selected from oxygen, sulfur, nitrogen and phosphorus, and optionally substituted with 1, 2 or 3 $R^X$ groups;

or $R^3$ and $R^{3'}$ together with the carbon atoms to which they are attached form a $C_{3-7}$ cycloalkyl or heterocyclic ring of 4 to 7 members containing 1, 2 or 3 heteroatoms independently selected from oxygen, sulfur, nitrogen and phosphorus, and optionally substituted with 1, 2 or 3 $R^X$ groups;

$R^4$ is selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, wherein alkyl, alkenyl, alkynyl, and cycloalkyl are each unsubstituted or substituted with at least one substituent, independently selected from $R^X$;

or $R^3$ and $R^4$ together with the atoms to which they are attached form a heterocyclic ring of 4 to 7 members containing 0, 1 or 2 additional heteroatoms independently selected from oxygen, sulfur, nitrogen and phosphorus, and optionally substituted with 1, 2 or 3 $R^X$ groups;

$R^5$ is selected from hydrogen, $C_{1-10}$ alkyl, $C_{2-10}$ alkenyl, $C_{2-10}$ alkynyl, $C_{3-10}$ cycloalkyl and $C_{3-10}$ cycloalkyl-$C_{1-4}$ alkyl, wherein alkyl, alkenyl, alkynyl and cycloalkyl are each unsubstituted or substituted with at least one substituent, independently selected from $R^X$;

$R^6$ is selected from hydrogen, halogen, $C_{1-10}$ alkyl, $C_{2-10}$ alkenyl, $C_{2-10}$ alkynyl, $C_{3-10}$ cycloalkyl and $C_{3-10}$ cycloalkyl-$C_{1-4}$ alkyl, wherein alkyl, alkenyl, alkynyl and cycloalkyl are each unsubstituted or substituted with at least one substituent, independently selected from $R^X$;

or $R^5$ and $R^6$ together with the atoms to which they are attached form a heterocyclic ring of 5 to 7 members containing 0, 1 or 2 additional heteroatoms independently selected from oxygen, sulfur, nitrogen and phosphorus, and optionally substituted with 1, 2 or 3 $R^X$ groups;

each $R^A$, $R^{A1}$, $R^{A2}$, $R^{A3}$, $R^{B1}$, $R^{B2}$ and $R^{B3}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^X$;

or each "$R^{A1}$ and $R^{B1}$", "$R^{A2}$ and $R^{B2}$" and "$R^{A3}$ and $R^{B3}$", together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2 or 3 $R^X$ groups;

$R^C$ and $R^D$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^X$;

or $R^C$ and $R^D$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^X$ groups;

$R^{E1}$ is selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $OR^{a1}$, $SR^{a1}$, —$S(O)_rR^{a1}$, —$C(O)R^{a1}$, $C(O)OR^{a1}$, —$C(O)NR^{a1}R^{b1}$ and —$S(O)_rNR^{a1}R^{b1}$, wherein alkyl, alkenyl, alkynyl, cycloalkyl, heterocyclyl, aryl and heteroaryl are each unsubstituted or substituted with at least one substituent, independently selected from $R^Y$;

each $R^X$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, —$(CR^{c1}R^{d1})_tNR^{a1}R^{b1}$, —$(CR^{c1}R^{d1})_tOR^{b1}$, —$(CR^{c1}R^{d1})_tC(O)R^{a1}$, —$(CR^{c1}R^{d1})_tC(=NR^{e1})R^{a1}$, —$(CR^{c1}R^{d1})_tC(=N-OR^{b1})R^{a1}$, —$(CR^{c1}R^{d1})_tC(O)OR^{b1}$, —$(CR^{c1}R^{d1})_tOC(O)R^{b1}$, —$(CR^{c1}R^{d1})_tC(O)NR^{a1}R^{b1}$, —$(CR^{c1}R^{d1})_tNR^{a1}C(O)R^{b1}$, —$(CR^{c1}R^{d1})_tC(=NR^{e1})NR^{a1}R^{b1}$, —$(CR^{c1}R^{d1})_tNR^{a1}C(=NR^{e1})R^{b1}$, —$(CR^{c1}R^{d1})_tOC(O)NR^{a1}R^{b1}$, —$(CR^{c1}R^{d1})_tNR^{a1}C(O)OR^{b1}$, —$(CR^{c1}R^{d1})_tNR^{a1}C(O)NR^{a1}R^{b1}$, —$(CR^{c1}R^{d1})_tNR^{a1}C(S)NR^{a1}R^{b1}$, —$(CR^{c1}R^{d1})_tR^{a1}C(=NR^{e1})NR^{a1}R^{b1}$, —$(CR^{c1}R^{d1})_tS(O)_rR^{b1}$, —$(CR^{c1}R^{d1})_tS(O)(=NR^{e1})R^{b1}$, —$(CR^{c1}R^{d1})_tN=S(O)R^{a1}R^{b1}$, —$(CR^{c1}R^{d1})_tS(O)_2OR^{b1}$, —$(CR^{c1}R^{d1})_tOS(O)_2R^{b1}$, —$(CR^{c1}R^{d1})NR^{a1}S(O)_rR^{b1}$, —$(CR^{c1}R^{d1})R^{a1}S(O)(=NR^{e1})R^{b1}$, —$(CR^{c1}R^{d1})_tS(O)_rNR^{a1}R^{b1}$, —$(CR^{c1}R^{d1})_tS(O)(=NR^{e1})NR^{a1}R^{b1}$, —$(CR^{c1}R^{d1})_tNR^{a1}S(O)_2NR^{a1}R^{b1}$, —$(CR^{c1}R^{d1})_tNR^{a1}S(O)(=NR^{e1})NR^{a1}R^{b1}$, —$(CR^{c1}R^{d1})_tP(O)R^{a1}R^{b1}$ and —$(CR^{c1}R^{d1})_tP(O)(OR^{a1})(OR^{b1})$ wherein alkyl, alkenyl, alkynyl, cycloalkyl, heterocyclyl, aryl and heteroaryl are each unsubstituted or substituted with at least one substituent, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^Y$;

or $R^{a1}$ and $R^{b1}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, independently selected from $R^Y$;

or $R^{c1}$ and $R^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, CN, $NO_2$, —$OR^{a2}$, —$SR^{a2}$, —$S(O)_rR^{a2}$, —$C(O)R^{a2}$, —$C(O)OR^{a2}$, —$S(O)_rNR^{a2}R^{b2}$ and —$C(O)NR^{a2}R^{b2}$;

each $R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, —$(CR^{c2}R^{d2})_tNR^{a2}R^{b2}$, —$(CR^{c2}R^{d2})_tOR^{b2}$, —$(CR^{c2}R^{d2})_tC(O)R^{a2}$, —$(CR^{c2}R^{d2})_tC(=NR^{e2})R^{a2}$, —$(CR^{c2}R^{d2})_tC(=N-OR^{b2})R^{a2}$, —$(CR^{c2}R^{d2})_tC(O)OR^{b2}$, —$(CR^{c2}R^{d2})_tOC(O)R^{b2}$, —$(CR^{c2}R^{d2})_tC(O)NR^{a2}R^{b2}$, —$(CR^{c2}R^{d2})_tNR^{a2}C(O)R^{b2}$, —$(CR^{c2}R^{d2})_tC(=NR^{e2})NR^{a2}R^{b2}$, —$(CR^{c2}R^{d2})_tNR^{a2}C(=NR^{e2})R^{b2}$, —$(CR^{c2}R^{d2})_tOC(O)NR^{a2}R^{b2}$, —$(CR^{c2}R^{d2})_tNR^{a2}C(O)OR^{b2}$, —$(CR^{c2}R^{d2})_tNR^{a2}C(O)NR^{a2}R^{b2}$, —$(CR^{c2}R^{d2})_tNR^{a2}C(S)NR^{a2}R^{b2}$, —$(CR^{c2}R^{d2})_tNR^{a2}C(=NR^{e2})NR^{a2}R^{b2}$, —$(CR^{c2}R^{d2})_tS(O)_rR^{b2}$, —$(CR^{c2}R^{d2})_tS(O)(=NR^{e2})R^{b2}$, —$(CR^{c2}R^{d2})_tN=S(O)R^{a2}R^{b2}$, —$(CR^{c2}R^{d2})_tS(O)_2OR^{b2}$, —$(CR^{c2}R^{d2})_tOS(O)_2R^{b2}$, —$(CR^{c2}R^{d2})_tNR^{a2}S(O)_rR^{b2}$, —$(CR^{c2}R^{d2})_tNR^{a2}S(O)(=NR^{e2})R^{b2}$, —$(CR^{c2}R^{d2})_tS(O)_rNR^{a2}R^{b2}$, —$(CR^{c2}R^{d2})_tS(O)(=NR^{e2})NR^{a2}R^{b2}$, —$(CR^{c2}R^{d2})_tNR^{a2}S(O)_2NR^{a2}R^{b2}$, —$(CR^{c2}R^{d2})_tNR^{a2}S(O)(=NR^{e2})NR^{a2}R^{b2}$, —$(CR^{c2}R^{d2})_tP(O)R^{a2}R^{b2}$ and —$(CR^{c2}R^{d2})_tP(O)$ (OR$^{a2}$)(OR$^{b2}$), wherein alkyl, alkenyl, alkynyl, cycloalkyl, heterocyclyl, aryl and heteroaryl are each unsubstituted or substituted with at least one substituent, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)N($C_{1-4}$ alkyl)$_2$, —C(O)N($C_{3-10}$ cycloalkyl)$_2$, —S(O)$_2C_{1-4}$ alkyl, —S(O)$_2C_{3-10}$ cycloalkyl, —S(O)$_2$N($C_{1-4}$ alkyl)$_2$ and —S(O)$_2$N($C_{3-10}$ cycloalkyl)$_2$;

m is selected from 0, 1, 2, 3 and 4;
n is selected from 1, 2, 3 and 4;
p is selected from 1, 2, 3 and 4;
each r is independently selected from 0, 1 and 2;
each t is independently selected from 0, 1, 2, 3 and 4;
each u is independently selected from 0, 1, 2, 3 and 4.

2. The compound of claim 1 or the pharmaceutically acceptable salt thereof, wherein n is 1 or 2 and $R^3$ and $R^{3'}$ are independently selected from hydrogen, halogen, $C_{1-10}$ alkyl, —OR$^{A3}$ and $C_{3-10}$ cycloalkyl, wherein alkyl and cycloalkyl are unsubstituted or substituted with at least one substituent independently selected from $R^X$.

3. The compound of claim 2 or the pharmaceutically acceptable salt thereof, wherein n is 1 or 2 and $R^3$ and $R^{3'}$ are independently selected from hydrogen, fluorine, methyl and OH.

4. The compound of claim 1 or the pharmaceutically acceptable salt thereof, wherein n is 1 or 2 and $R^{3'}$ is hydrogen, shown as formula (II):

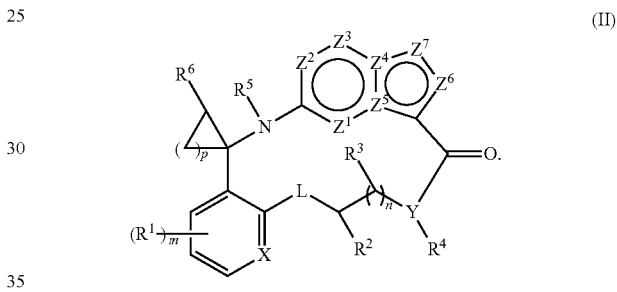

(II)

5. The compound of claim 1 or the pharmaceutically acceptable salt thereof, wherein $R^3$ and $R^{3'}$ together with the carbon atoms to which they are attached form a $C_{3-7}$ cycloalkyl or heterocyclic ring of 4 to 7 members containing 1, 2 or 3 heteroatoms independently selected from oxygen, sulfur, nitrogen and phosphorus, and optionally substituted with 1, 2 or 3 $R^X$ groups.

6. The compound of claim 5 or the pharmaceutically acceptable salt thereof, wherein $R^3$ and $R^{3'}$ together with the carbon atoms to which they are attached form cyclopropyl or cyclobutyl.

7. The compound of claim 1 or the pharmaceutically acceptable salt thereof, wherein
X is CH; or
X is N.

8. The compound of claim 1 or the pharmaceutically acceptable salt thereof, wherein $R^1$ is selected from $C_{1-10}$ alkyl, $C_{3-10}$ cycloalkyl, halogen and CN, wherein alkyl and cycloalkyl are unsubstituted or substituted with at least one substituent independently selected from $R^X$.

9. The compound of claim 8 or the pharmaceutically acceptable salt thereof, wherein $R^1$ is fluorine and m is 1.

10. The compound of claim 1 or the pharmaceutically acceptable salt thereof, wherein L is selected from —(CR$^C$R$^D$)$_u$O(CR$^C$R$^D$)$_t$—, —CR$^C$R$^D$—, —NR$^A$— and —(CR$^C$R$^D$)$_u$S(CR$^C$R$^D$)$_t$—.

11. The compound of claim 10 or the pharmaceutically acceptable salt thereof, wherein L is selected from —O—, —CH$_2$—, —NH— and —S—.

12. The compound of claim 1 or the pharmaceutically acceptable salt thereof, wherein $R^2$ is independently selected from hydrogen, $C_{1-10}$ alkyl and $C_{3-10}$ cycloalkyl, wherein alkyl and cycloalkyl are unsubstituted or substituted with at least one substituent independently selected from $R^X$.

13. The compound of claim 12 or the pharmaceutically acceptable salt thereof, wherein $R^2$ is selected from hydrogen and methyl.

14. The compound of claim 1 or the pharmaceutically acceptable salt thereof, wherein Y is O and $R^4$ is absent.

15. The compound of claim 1 or the pharmaceutically acceptable salt thereof, wherein Y is N.

16. The compound of claim 15 or the pharmaceutically acceptable salt thereof, wherein $R^4$ is selected from hydrogen, $C_{1-10}$ alkyl and $C_{3-10}$ cycloalkyl, wherein alkyl and cycloalkyl are unsubstituted or substituted with at least one substituent independently selected from $R^X$.

17. The compound of claim 16 or the pharmaceutically acceptable salt thereof, wherein $R^4$ is selected from hydrogen and methyl.

18. The compound of claim 1 or the pharmaceutically acceptable salt thereof, wherein $R^3$ and $R^4$ together with the atoms to which they are attached form a heterocyclic ring of 4 to 7 members containing 0, 1 or 2 additional heteroatoms independently selected from oxygen, sulfur, nitrogen and phosphorus, and optionally substituted with $R^X$.

19. The compound of claim 18 or the pharmaceutically acceptable salt thereof, wherein $R^3$ and $R^4$ together with the atoms to which they are attached form

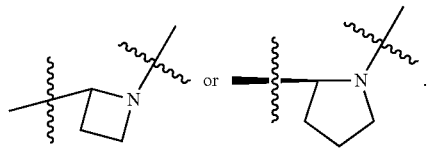

20. The compound of claim 1 or the pharmaceutically acceptable salt thereof, wherein $R^5$ and $R^6$ are independently selected from hydrogen, $C_{1-10}$ alkyl, $C_{3-10}$ cycloalkyl and heterocyclyl, wherein alkyl, cycloalkyl and heterocyclyl are each unsubstituted or substituted with at least one substituent independently selected from $R^X$.

21. The compound of claim 20 or the pharmaceutically acceptable salt thereof, wherein $R^5$ and $R^6$ are independently selected from hydrogen, methyl, $CD_3$ and ethyl.

22. The compound of claim 1 or the pharmaceutically acceptable salt thereof, wherein $R^5$ and $R^6$ together with the atoms to which they are attached form a heterocyclic ring of 5 to 7 members containing 0, 1 or 2 additional heteroatoms independently selected from oxygen, sulfur, nitrogen and phosphorus, and optionally substituted with $R^X$.

23. The compound of claim 22 or the pharmaceutically acceptable salt thereof, wherein $R^5$ and $R^6$ together with the atoms to which they are attached form a 5-6 membered heterocyclic ring without additional heteroatom.

24. The compound of claim 23 or the pharmaceutically acceptable salt thereof, wherein the substructure of Formula (III)

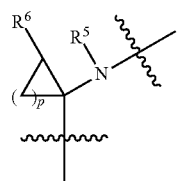

in Formula (I) is

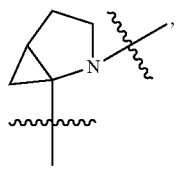 [SMILES: *N1CCC2CC21*]

wherein the ∿ symbol indicates the point of attachment to the rest of the molecule.

25. The compound of claim 1 or the pharmaceutically acceptable salt thereof, wherein p is 1.

26. The compound of claim 1 or the pharmaceutically acceptable salt thereof, wherein
$Z^4$ is N and $Z^5$ is C; or
$Z^4$ is C and $Z^5$ is N.

27. The compound of claim 1 or the pharmaceutically acceptable salt thereof, wherein $Z^1$ and $Z^7$ are N, and $Z^2$, $Z^3$ and $Z^6$ are $CR^X$, $R^X$ is selected from hydrogen, halogen, OH, CN, $NO_2$, $C_{1-10}$ alkyl, $C_{3-10}$ cycloalkyl, $C_{3-10}$ cycloalkyl-$C_{1-4}$ alkyl, heterocyclyl, heteroaryl-$C_{1-4}$ alkyl, $-(CR^{c1}R^{d1})_rNR^{a1}R^{b1}$ and $-(CR^{c1}R^{d1})_rNR^{a1}C(O)R^{b1}$.

28. The compound of claim 27 or the pharmaceutically acceptable salt thereof, wherein $R^X$ is selected from hydrogen, $NH_2$,

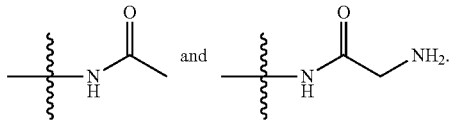

29. The compound of claim 1, selected from

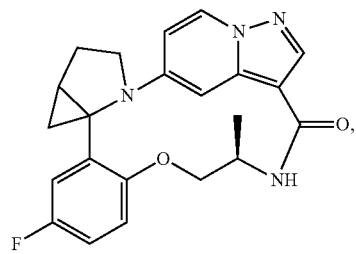

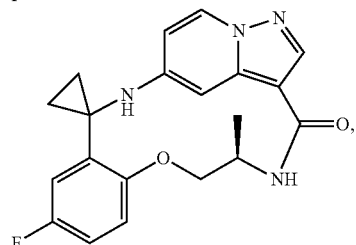

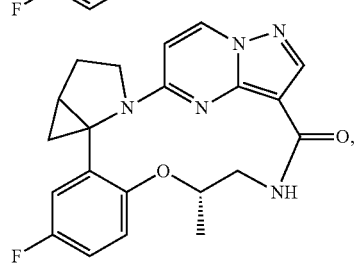

127
-continued
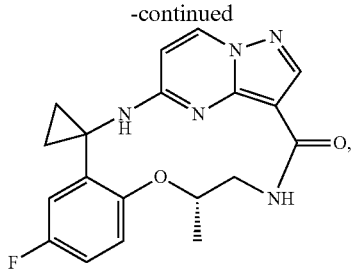
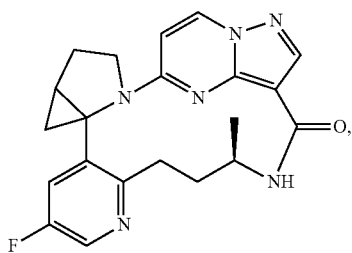
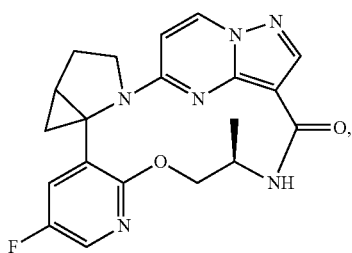
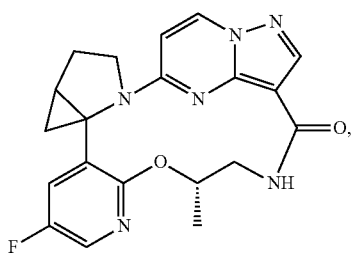
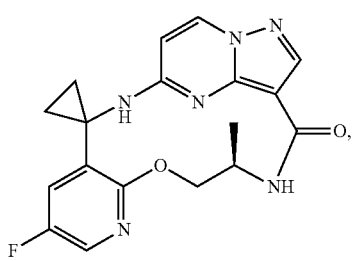
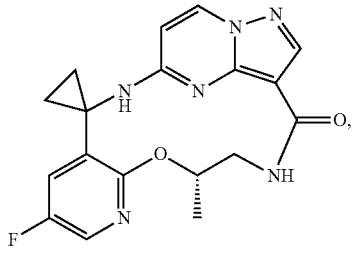
128
-continued
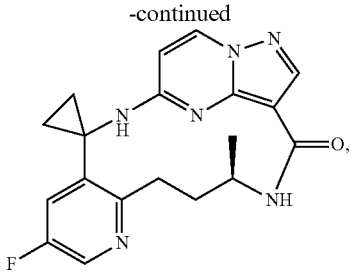
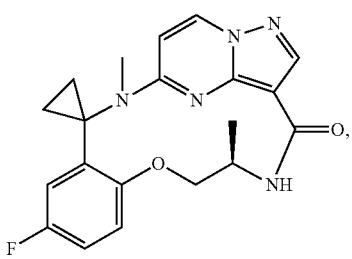
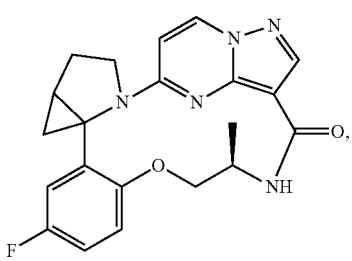
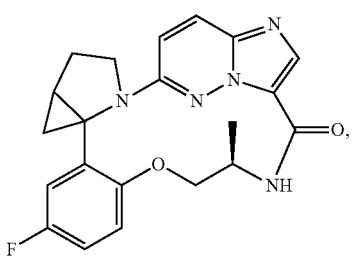
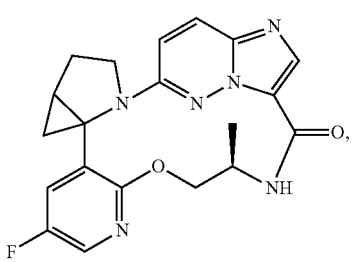
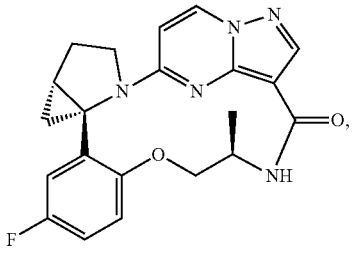

129
-continued
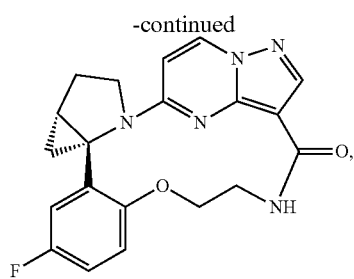
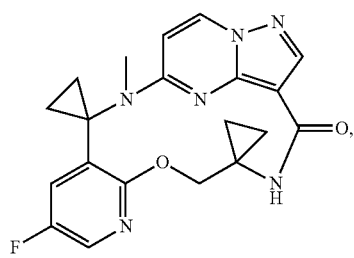
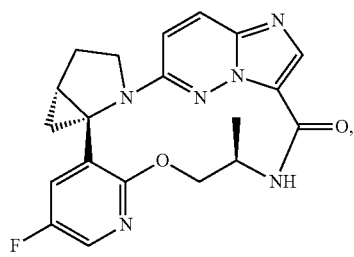
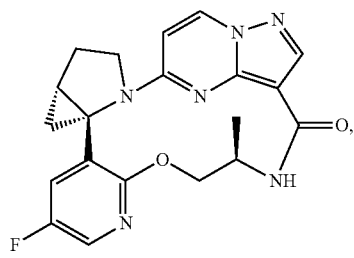
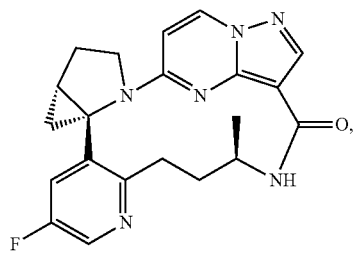
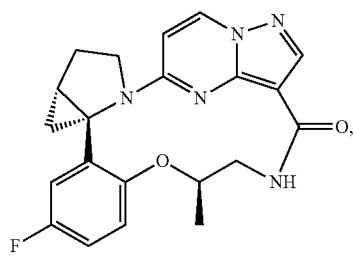
130
-continued
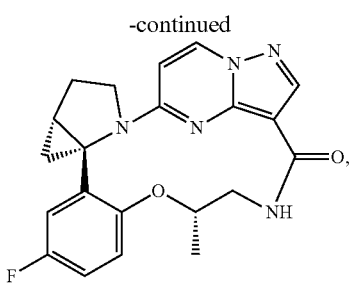
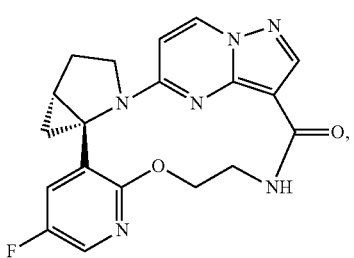
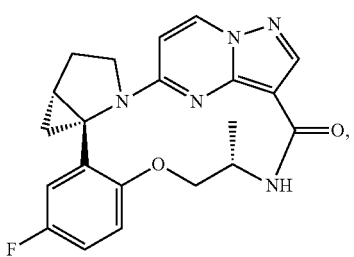
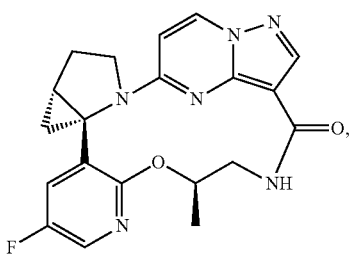
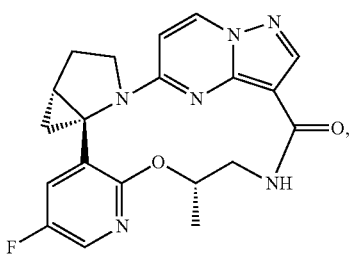
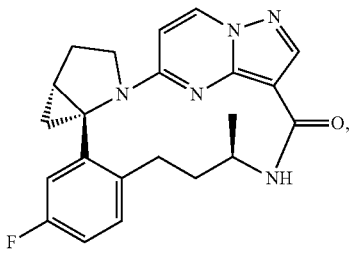

131
-continued
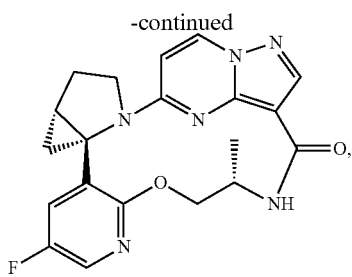
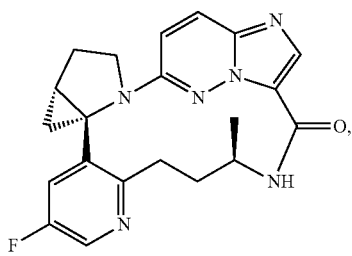
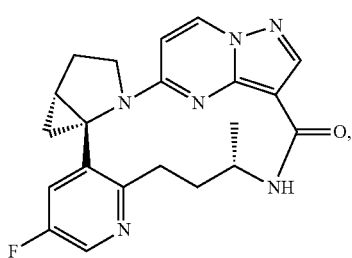
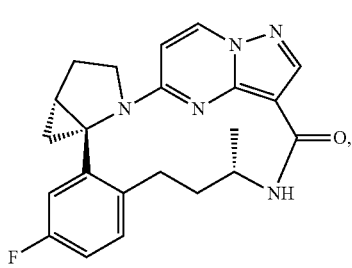
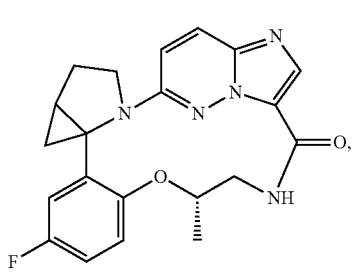
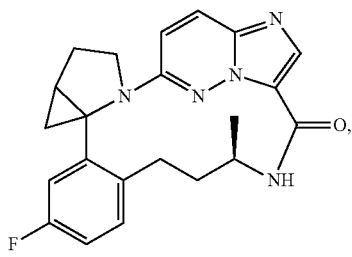
132
-continued
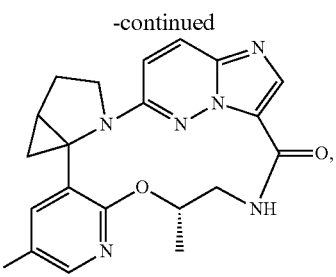
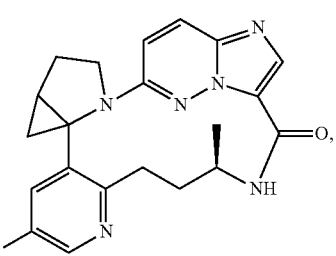
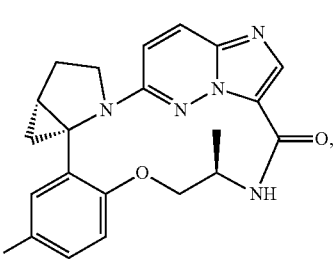
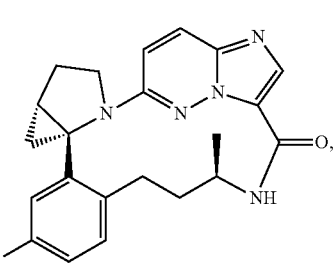
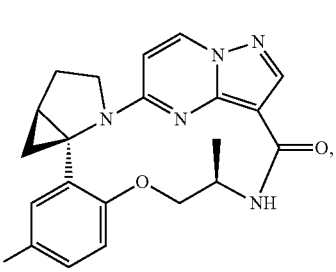
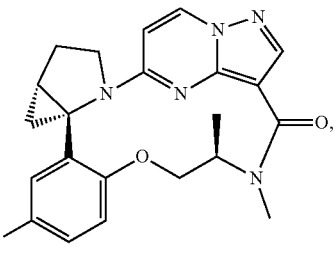

133
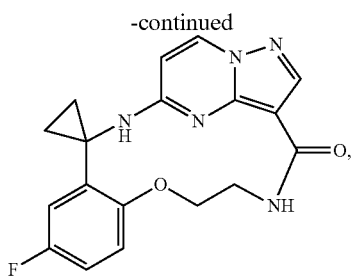
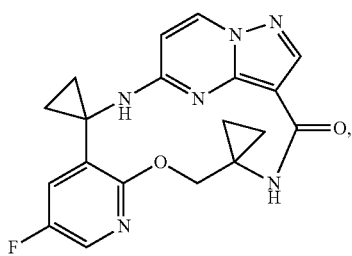
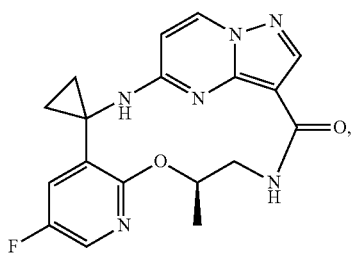
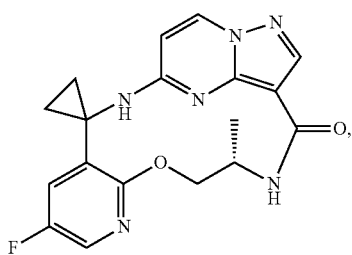
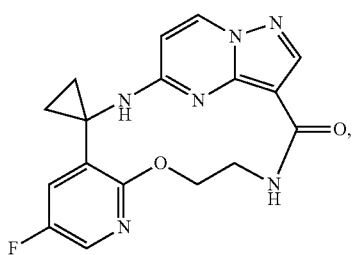
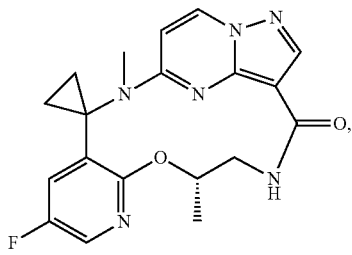
134
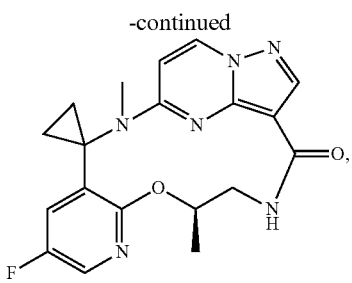
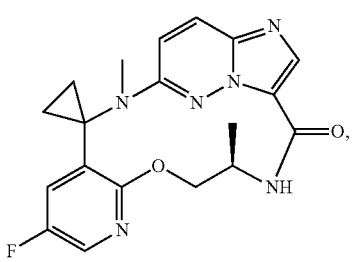
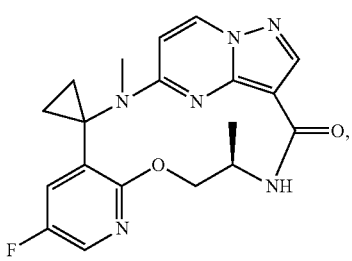
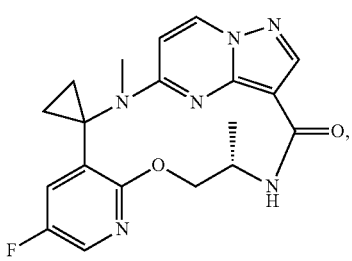
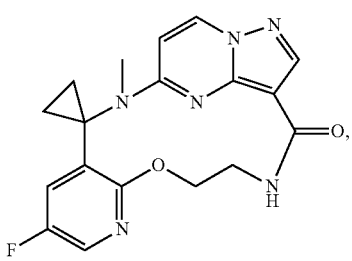
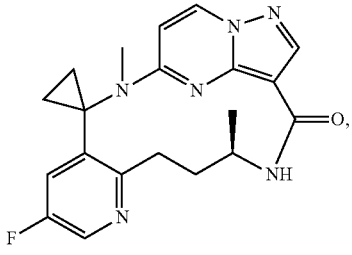

135
-continued
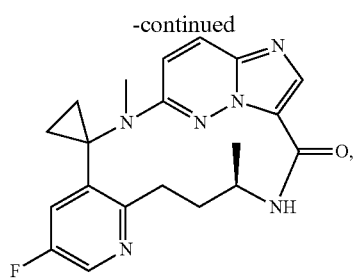
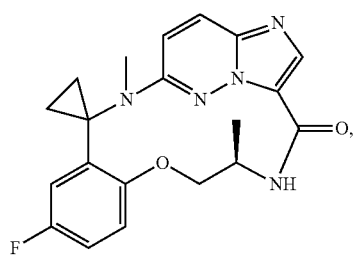
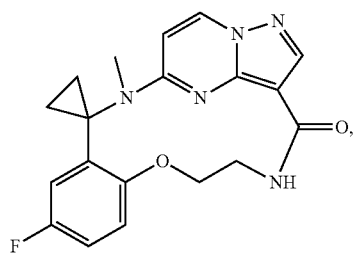
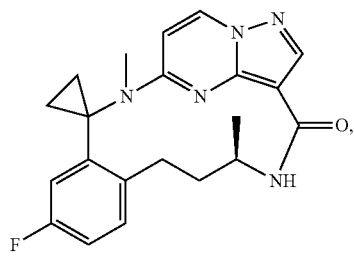
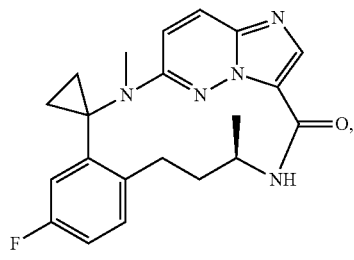
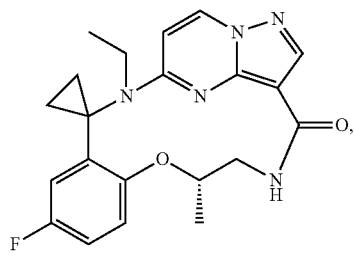
136
-continued
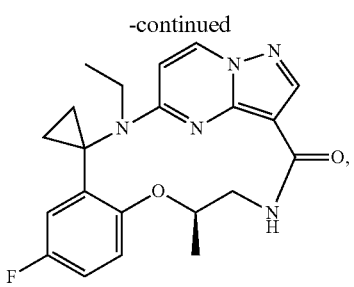
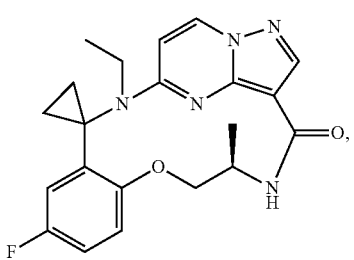
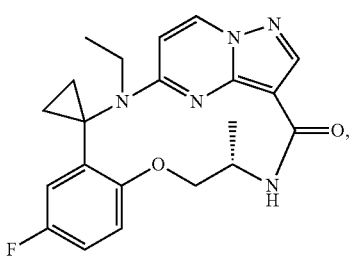
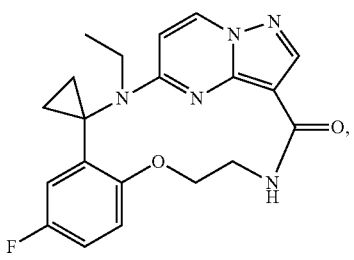
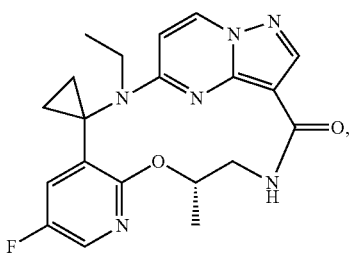
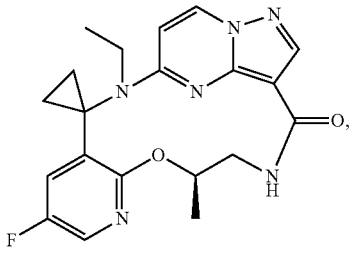

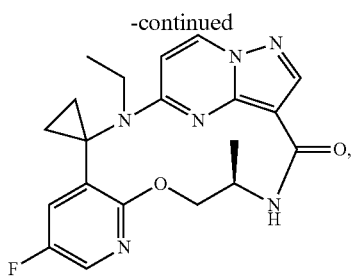
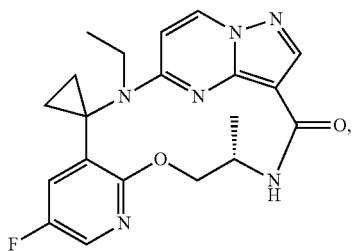
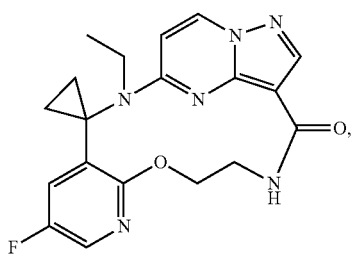
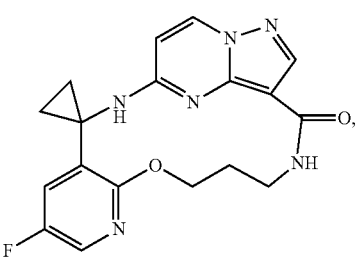
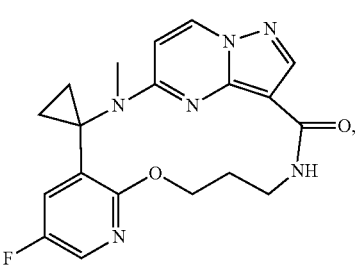
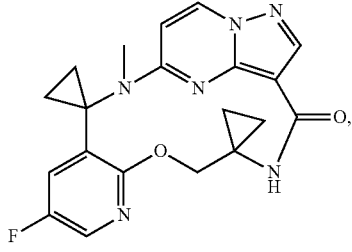
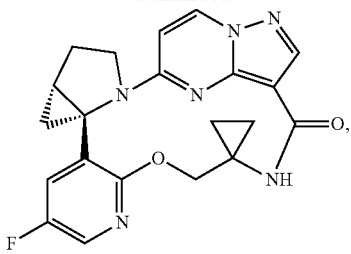
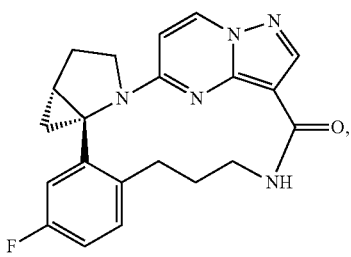
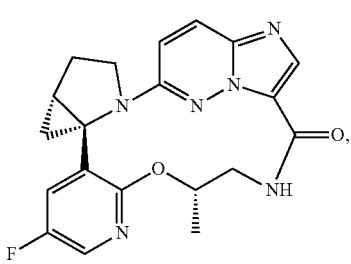
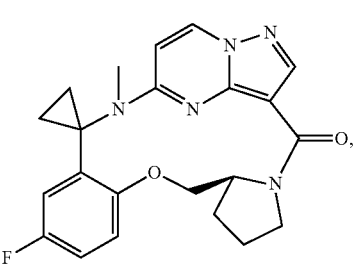
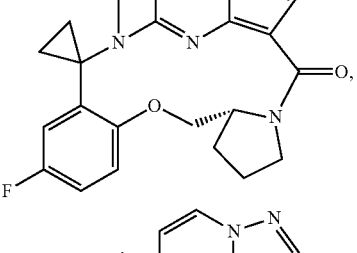
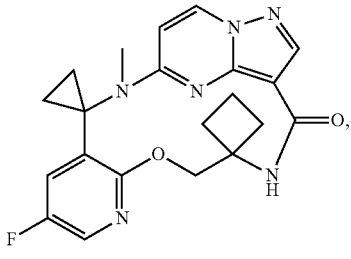

139
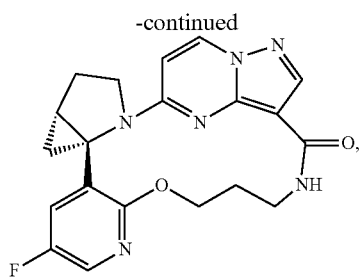
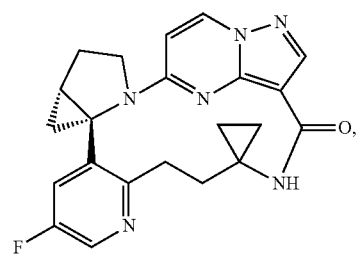
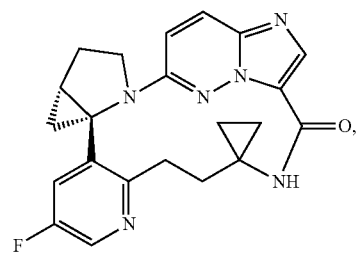
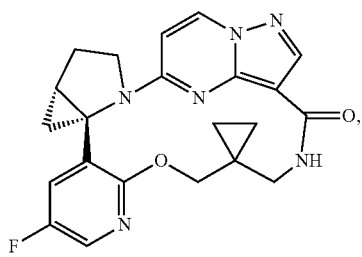
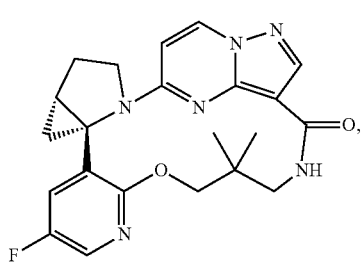
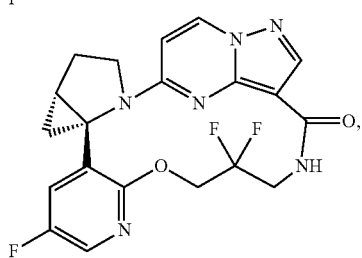
140
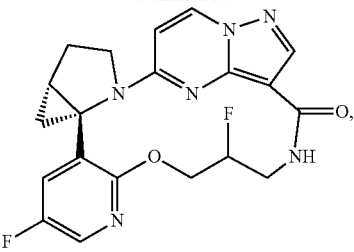
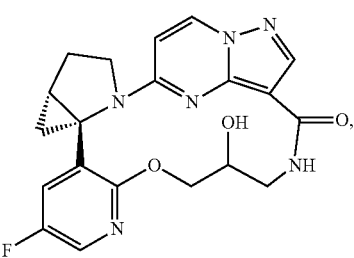
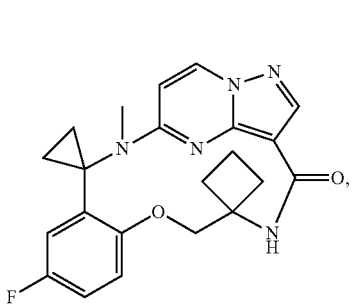
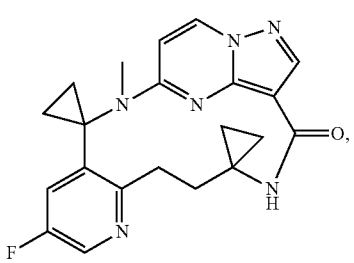
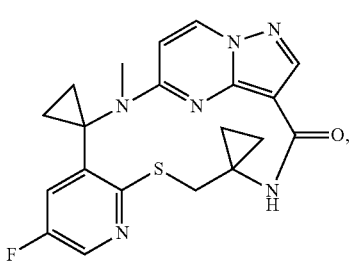
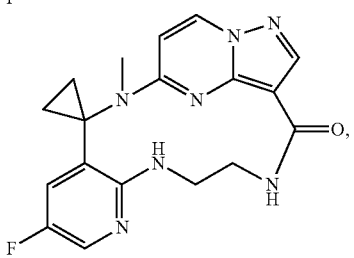

141
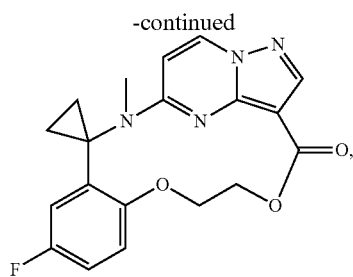
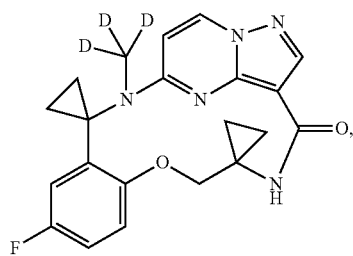
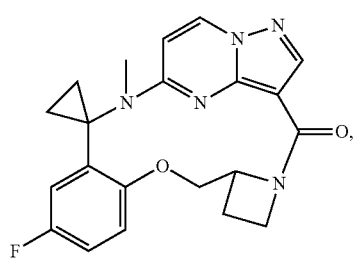
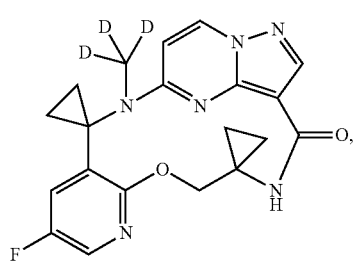
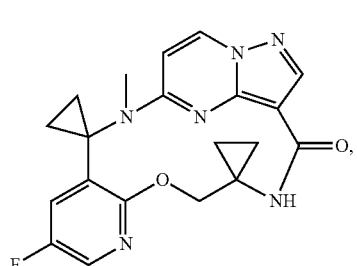
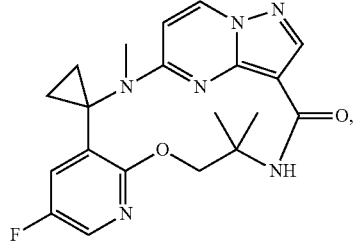
142
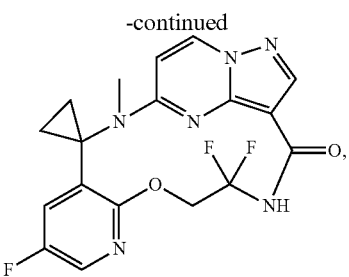
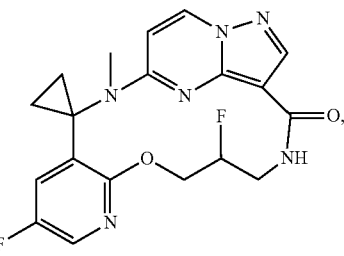
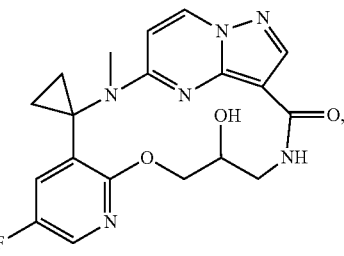
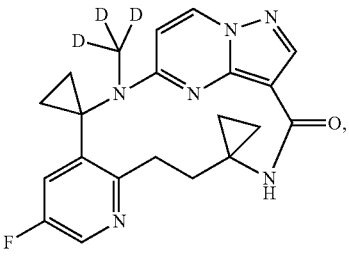
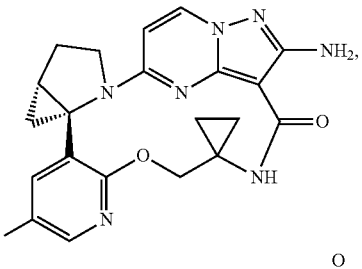
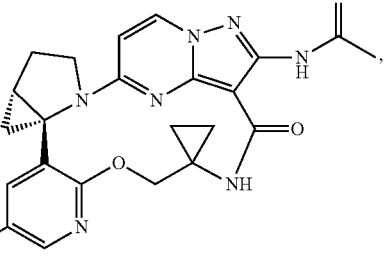

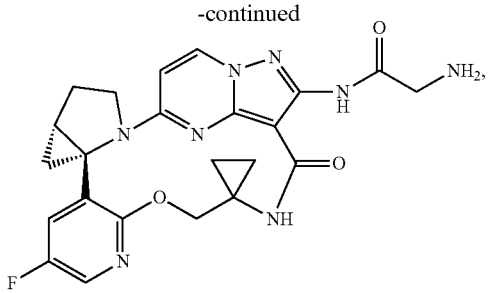

and pharmaceutically acceptable salts thereof.

30. A pharmaceutical composition, comprising the compound of claim 1 or the pharmaceutically acceptable salt thereof and at least one pharmaceutically acceptable carrier.

31. A method of treating a cell-proliferative disorder, comprising administering to a subject in need of such treatment an effective amount of the compound of claim 1 or the pharmaceutically acceptable salt, wherein the cell-proliferative disorder is selected from the group consisting of lung, pancreatic, breast, ovarian, colorectal, thyroid cancer, glioma, melanoma, and epidermoid cancer.

* * * * *